(12) United States Patent
Buckland et al.

(10) Patent No.: US 7,545,504 B2
(45) Date of Patent: Jun. 9, 2009

(54) IMAGING SYSTEMS USING UNPOLARIZED LIGHT AND RELATED METHODS AND CONTROLLERS

(75) Inventors: Eric L. Buckland, Hickory, NC (US);
John R. Marciante, Webster, NY (US);
Joseph A. Izatt, Raleigh, NC (US);
William J. Brown, Durham, NC (US)

(73) Assignee: Biotigen, Inc., Durham, NC (US)

( * ) Notice: Subject to any disclaimer, the term of this patent is extended or adjusted under 35 U.S.C. 154(b) by 127 days.

(21) Appl. No.: 11/539,275

(22) Filed: Oct. 6, 2006

(65) Prior Publication Data

US 2007/0086017 A1 Apr. 19, 2007

Related U.S. Application Data

(60) Provisional application No. 60/725,087, filed on Oct. 7, 2005.

(51) Int. Cl.
*G01B 9/02* (2006.01)
*G01J 4/00* (2006.01)
*G02B 5/30* (2006.01)
*G02B 27/28* (2006.01)

(52) U.S. Cl. .................................. 356/495; 356/479

(58) Field of Classification Search ................ 356/477, 356/479, 497, 495; 250/227.19, 227.27; 385/12
See application file for complete search history.

(56) References Cited

U.S. PATENT DOCUMENTS 4,905,169 A 2/1990 Buican et al.
5,104,222 A 4/1992 Kersey et al.
6,195,162 B1 2/2001 Varnham et al.
6,421,131 B1 7/2002 Miller
6,801,319 B2 10/2004 Szafraniec et al.
6,847,744 B2 1/2005 Azami et al.
6,870,973 B2 3/2005 Fidric et al.
6,891,998 B2 5/2005 Jones
6,946,990 B2 9/2005 Monk (Continued)

FOREIGN PATENT DOCUMENTS

GB 2 267 752 A 12/1993

(Continued)

OTHER PUBLICATIONS

U.S. Appl. No. 11/495,226, filed Jul. 28, 2006, Izatt et al.

(Continued)

*Primary Examiner*—Michael A Lyons
(74) *Attorney, Agent, or Firm*—Myers Bigel Sibley & Sajovec

(57) ABSTRACT

Optical imaging systems are provided including a light source and a depolarizer. The light source is provided in a source arm of the optical imaging system. A depolarizer is coupled to the light source in the source arm of the optical imaging system and is configured to substantially depolarize the light from the light source. Related methods and controllers are also provided.

30 Claims, 44 Drawing Sheets

U.S. PATENT DOCUMENTS

| | | |
|---|---|---|
| 6,992,777 B2 | 1/2006 | Han et al. |
| 7,039,262 B2 | 5/2006 | Li et al. |
| 7,050,222 B2 | 5/2006 | Yu et al. |
| 7,072,369 B2 | 7/2006 | Matsushita et al. |
| 7,075,644 B2 | 7/2006 | Yamamoto et al. |
| 7,085,441 B1 | 8/2006 | Kozlov |
| 7,088,878 B2 | 8/2006 | Waagaard et al. |
| 7,099,081 B2 | 8/2006 | Norton et al. |
| 7,301,644 B2 | 11/2007 | Knighton et al. |
| 2003/0020920 A1 | 1/2003 | Dave et al. |
| 2005/0018201 A1 | 1/2005 | de Boer et al. |
| 2007/0002327 A1 | 1/2007 | Zhou et al. |
| 2007/0291277 A1 | 12/2007 | Everett et al. |

FOREIGN PATENT DOCUMENTS

| | | | |
|---|---|---|---|
| WO | WO 99/19693 A1 | 4/1999 | |

OTHER PUBLICATIONS

Burns et al., "Fiber-Optic Gyroscopes with Broad-Band Sources," *Journal of Lightwave Technology*, vol. LT-1, No. 1, Mar. 1983, 98-105.

Burns et al., "Fiber-Optic Gyroscopes with Depolarized Light," *Journal of Lightwave Technology*, vol. 10, No. 7, Jul. 1992, 992-999.

Szafraniec et al., "Theory of Polarization Evolution in Interferometric Fiber-Optic Depolarized Gyros," *Journal of Lightwave Technology*, vol. 17, No. 4, Apr. 1999, 579-590.

Burns et al. "Depolarized source for fiber-optic applications" *Optics Letters* 16(6):381-383 (1991).

International Search Report an Written Opinion for PCT/US2006/039301; date of mailing May 25, 2007.

International Search Report and Written Opinion for PCT/US2006/039301; date of mailing Feb. 15, 2007.

Senthilkumaran, Paramasivam, "Berry's phase fiber loop mirror characteristics," J. Opt. Soc. Am. B, vol. 22, No. 2, Feb. 2005, pp. 505-511.

Depolarizer (Polarization Scrambler)

IMAGING SYSTEMS USING UNPOLARIZED LIGHT AND RELATED METHODS AND CONTROLLERS

CLAIM OF PRIORITY

The present application claims priority from U.S. Provisional Application No. 60/725,087, filed Oct. 7, 2005, the disclosure of which is hereby incorporated herein by reference as if set forth in its entirety.

FIELD OF THE INVENTION

The present invention relates to imaging and, more particularly, to imaging systems and related methods and controllers.

BACKGROUND OF THE INVENTION

There are a variety of approaches to imaging in general. One approach is optical coherence tomography (OCT). OCT systems include Fourier domain OCT (FD-OCT) and time domain OCT (TD-OCT). FD-OCT generally includes swept source (SS) and spectral domain (SD), where SD systems generally use spectrometers rather than a swept source. TD systems generally rely on movement of a mirror or reference source over time to control imaging depth. In contrast, for FD-OCT, the imaging depth may be determined by Fourier transform relationships between the acquired spectrum, rather than by the range of a physically scanned mirror. Specifically, in FD-OCT, the number of samples of the spectrum may be used to control the imaging depth, with a greater number of samples of spectrum providing a deeper imaging capability.

In general, TD-OCT and FD-OCT are implementations of Low-Coherence Interferometry (LCI), a signal processing technique that relies on the mixing of two correlated broadband, or low coherence, optical signals that travel differential paths. Non-imaging implementations include Optical Low Coherence Reflectometry (OLCR), optical coherence-domain reflectometry (OCDR), and optical frequency domain reflectometry (OFDR).

Low coherence interferometry is a specific class of the more general concept of optical interferometry. There are many implementations of optical interferometers, including, for example, Michelson interferometers, Mach-Zehnder interferometers, and Fabry-Perot cavity interferometers. Michelson and Mach-Zehnder interferometers are commonly used for sensing, metrology, and imaging applications. Low coherence implementations rely on the concept of coherence gating. An interferometric signal whose modulation amplitude is proportional to the product of the two mixed signals is generated when the difference between optical path lengths is within the coherence length of the signal. The coherence length is inversely proportional to the source bandwidth.

Optical signals may be described by their state and degree of polarization. Typically, any optical signal may be decomposed into two orthogonal polarizations. The state of polarization (SOP) describes the relative amplitudes and phases of the two orthogonal components of polarization. The degree of polarization (DOP) describes the ratio of polarized light to the total irradiance. Unpolarized light is described by light that has energy distributed uniformly among the orthogonal polarization states, regardless of the basis set used to decompose the light field. Incandescent light tends to be highly unpolarized. In contrast, a laser tends to produce highly polarized light fields. A field may be described by the sum of its polarized component and its unpolarized component. A DOP of 1.0 describes a fully polarized field, and a DOP of zero describes an unpolarized field. Superluminescent light emitting diodes (SLED) used in OCT tend to have a DOP from about 50% to about 80%.

Light fields may be polarized by passing through a polarizer. Furthermore, light fields may be depolarized by a number of methods known to those having skill in the art.

Interferometric efficiency follows a cosine-squared law for the mixing of polarized signals. The signal strength of interfering polarized signals falls as the cosine-squared of the angle between the two polarizations. Orthogonal signals do not typically interfere. The reduction of interferometric efficiency caused by unmatched SOP can be referred to as polarization fading. Under certain conditions, unpolarized light interferes with a static reduction in polarization efficiency of about 50%.

Referring now to FIG. 1A, a conventional Michelson interferometer will be discussed. As illustrated therein, the interferometer includes an optical source 150, a beam splitter/combiner 101, first and second birefringent optical paths A 106 and B 107 and corresponding reflectors A 103 and B 104, and a detector 105. The optical source 150 may have an arbitrary coherence length and arbitrary DOP is incident on the beam splitter/combiner 101. A fraction of the signal travels the birefringent optical path A 106 towards the Reflector A 103. The remaining signal, ignoring some unavoidable losses, travels the second birefringent path B 107 to the second reflector B 104. The reflected signals from the Reflector A 103 and the Reflector B 104 reverse paths and recombine at the beam splitter/combiner 105, where the subsequent mixed signals interfere, and the interference signal is captured on the detector 105. In this configuration, no means for minimizing or controlling polarization fading is provided.

Referring now to FIG. 1B, a conventional Michelson interferometer using state-of-polarization (SOP) control to possibly reduce polarization fading will be discussed. As illustrated in FIG. 1B, the interferometer includes a polarized optical source 160, a beam splitter/combiner 101, first and second birefringent optical paths A 106 and B 107 and corresponding first and second reflectors A 103 and B 104, SOP control 102, and a detector 105. SOP control 102 may be used in one or both of the birefringent optical paths A 106 and path B 107. The use of SOP control 102 in this configuration may increase the likelihood that the polarization in one path may be aligned to the polarization in the other path, so that polarization fading may be reduced or possibly eliminated.

Referring now to FIG. 2A, a conventional Mach-Zehnder interferometer will be discussed. As illustrated in FIG. 2A, the interferometer includes an optical source 250, a beam splitter 208, first and second birefringent optical paths A 206 and 207, a beam combiner 209 and a detector 205. The optical source 250 may have arbitrary coherence length and arbitrary DOP is incident on the beam splitter 208. A fraction of the signal travels the birefringent path A 206 towards the beam combiner 209. The remaining signal, ignoring some unavoidable losses, travels the second birefringent path B 207 to the same beam combiner 209. The signals from path A 206 and path B 207 mix at the beam combiner 209 and the interference signal is captured on the detector 205. In this configuration, no means for minimizing or controlling polarization fading is provided.

Referring now to FIG. 2B, a conventional Mach-Zehnder interferometer using state-of-polarization (SOP) control to possibly reduce polarization fading will be discussed. As illustrated in FIG. 2B, the interferometer includes an polarized optical source 260, a beam splitter 208, first and second birefringent optical paths A 206 and 207, SOP control 202, a beam combiner 209 and a detector 205. SOP control 202 may be used in one or both of the path A 206 and path B 207. The use of SOP control 202 in this configuration may increase the likelihood that the polarization in one path may be aligned to the polarization in the other path, so that polarization fading may be reduced or possibly eliminated.

Referring now to FIG. 3, a conventional OCT system will be discussed. As illustrated in FIG. 3, the OCT includes a low-coherence or broadband source 300, polarization controllers 302, an isolator 305, a splitter/combiner 301 and a spectrometer. The low-coherence or broadband light source 300 is coupled to a splitter/coupler 301 by a source arm 308, a spectrometer 304 is coupled to the splitter/coupler 301 by a detector arm 303, a reference arm 306 extends from the splitter/coupler 301 to a reference, such as a mirror, and a sample arm 307 extends from the splitter/coupler 301 to a sample, schematically illustrated as a human eye in FIG. 3. In compensating for polarization effect in the OCT system of FIG. 3, it is known to install one or more polarization controllers 302 in the OCT system as illustrated in FIG. 3. These polarization controllers 302 may be used to increase the likelihood that the light returning from the reference arm 306 and the sample arm 307 are aligned relative to each other and potentially aligned with a dispersive element in the spectrometer 304.

The polarization controller 302 between the source 300 and an isolator 305 can be used to align the source polarization with the isolator 305, which may be polarization sensitive. Polarization insensitive isolators may also be used, in which case that polarization controller 302 between the source 300 and the isolator 305 may not be present. These polarization controllers 302 are typically "tweaked" or adjusted on an hourly or daily time scale in order to maintain optimal system performance. Such systems are typically sensitive to disturbances of any connections, but particularly those of reference/sample arms 306 and 307, the optical connections to the reference and the sample. System performance may also be sensitive to the performance of the broadband (Low-coherence) light source 300, the coupler 301 and the spectrometer 304.

SUMMARY OF EMBODIMENTS OF THE PRESENT INVENTION

Some embodiments of the present invention provide optical imaging systems including a light source and a depolarizer. The light source is provided in a source arm of the optical imaging system. A depolarizer is coupled to the light source in the source arm of the optical imaging system and is configured to substantially depolarize the light from the light source.

In further embodiments of the present invention, a birefringence controller may be provided in a first path or a second path of the system and may be configured to modify a polarization-dependent optical path length in the at least one of the first and second paths. In certain embodiments of the present invention, control settings of the birefringence controller may be set during manufacture and configured to be adjusted infrequently. In further embodiments of the present invention, control settings of the birefringence controller may be dynamic and may be configured to be set based on a metric of a measured or imaged signal and/or a rate of active control associated with demands of an application.

In still further embodiments of the present invention, the system may further include a power coupler coupled to the depolarizer and the first and second paths. The power coupler may be configured to provide light to and combine light from the first and second paths.

In some embodiments of the present invention, the system further includes an isolator coupled between the light source and the depolarizer. The isolator may be configured to inhibit light from reentering the light source.

In further embodiments of the present invention, the system further includes a spectrometer in a detector arm of the optical imaging system. The spectrometer may be configured to receive light from the light source and disperse the received light onto at least one detector. The detector may include a detector array including a plurality of detectors. Ones of the plurality of detectors may be configured to measure a power in a frequency band that is a subset of a total spectrum of the light source. The depolarizer may be further configured to substantially depolarize over the frequency band viewed by a single detector.

In still further embodiments of the present invention, the system may further include a photodiode in a detector arm of the optical imaging system. The photodiode may be configured to measure incident power over a time interval.

In some embodiments of the present invention, the depolarizer may include a Lyot depolarizer, a multi-path depolarizer or a polarization scrambler.

In further embodiments of the present invention, the optical imaging system may be a spectral domain optical coherence tomography (OCT) imaging system and the light source may be a broadband light source.

In still further embodiments of the present invention, the optical imaging system may be a frequency domain optical coherence tomography (OCT) imaging system and the light source may be a narrowband light source having an optical frequency that varies with time.

In some embodiments of the present invention, the optical imaging system may be a time domain optical coherence tomography (OCT) imaging system and the light source may be a broadband light source.

Further embodiments of the present invention provide optical imaging systems including a substantially unpolarized light source in a source arm of the optical imaging system. The unpolarized light source is configured to provide substantially unpolarized light to first and second paths of the system.

Still further embodiments of the present invention provide optical imaging systems including a light source and a depolarizer. The light source is provided in a source arm of the optical imaging system. The depolarizer is provided in a reference arm of the optical imaging system and is configured to substantially depolarize light returning from the reference arm.

Some embodiments of the present invention provide optical interferometry systems including a light source and a birefringence controller. The light source is configured to provide substantially unpolarized light to first and second paths. The birefringence controller is provided in at least one of the first and second paths and is configured to modify a polarization-dependent optical path length in the at least one of the first and second paths.

In further embodiments of the present invention, the system may further include a depolarizer in the at least one of the first and second paths including the birefringence controller. The depolarizer may be configured to compensate for polarizing elements present in the at least one of the first and second paths.

In still further embodiments of the present invention, the system may further include a power coupler coupled to the unpolarized light source and the first and second paths. The power coupler may be configured to provide a portion of light produced by the unpolarized light source to the first path and a remaining portion of the light produced by the unpolarized source to the second path.

In some embodiments of the present invention, the system may further include first and second reflectors. The first reflector may be provided in the first path that reflects at least a portion of the light provided to the first path. The second reflector may be provided in the second path that reflects at least a portion of the light provided to the second path.

In further embodiments of the present invention, the power coupler may be further configured to combine the reflected light from the first and second paths. The system may further include a detector configured to receive the combined reflected light.

In still further embodiments of the present invention, the system may further include a power splitter coupled to the unpolarized light source and the first and second paths. The power splitter may be configured to provide a portion of light produced by the unpolarized source to the first path and a remaining portion of the light produced by the unpolarized source to the second path. The system may further include a power coupler coupled to the first and second paths. The power coupler may be configured to combine at least a portion of the light provided to the first path and at least some portion of the light provided to the second path. The system may further include a detector configured to receive the combined light from the first and second paths.

Some embodiments of the present invention provide optical imaging systems including at least two light sources and a polarization beam combiner. The at least two light sources are provided in a source arm of the system. The polarization beam combiner is coupled to the at least two light sources and configured to output a substantially unpolarized signal having a power in each orthogonal polarization.

In further embodiments of the present invention, the system may further include at least one variable optical attenuator between at least one of the at least two light sources and the polarization beam combiner. The at least one variable optical attenuator may be configured to control a power level from the at least one of the at least two light sources.

In still further embodiments of the present invention, the system may further include at least one filter between at least one of the at least two light sources and the polarization beam combiner. The at least one filter may be configured to provide equalized power across a spectrum. In certain embodiments of the present invention, the system may be an optical coherence tomography imaging system.

Some embodiments of the present invention provide variable optical path length birefringence controllers including a polarization beam splitter. The polarization beam splitter is configured to receive light and split the light into first and second polarized components. The first and second polarized components travel respective first and second paths and at least one of the first and second paths includes a path length adjustment mechanism.

In further embodiments of the present invention, the path length adjustment mechanism may include a path delay.

In still further embodiments of the present invention, the path length adjustment mechanism may include a nonlinear optical fiber that is configured to control an optical phase delay of the at least one of the first and second paths.

In some embodiments of the present invention, the path length adjustment mechanism may include an electro optic phase modulator configured to control an optical phase delay of the at least one of the first and second paths.

In further embodiments of the present invention, the path length adjustment mechanism may include a polarization-maintaining optical fiber configured to control an optical phase delay of the at least one of the first and second paths.

Still further embodiments of the present invention provide a birefringence controller including an electro optic modulator configured to control a relative phase delay between first and second polarization states.

Some embodiments of the present invention provide birefringence controllers including a birefringent optical fiber configured to control a relative phase delay between first and second polarization states.

Further embodiments of the present invention provide, birefringence controllers including a birefringent optical crystal configured to control a relative phase delay between first and second polarization states.

Still further embodiments of the present invention provide birefringence controllers in at least one of a first path and a second path of an optical imaging system. The birefringence controller is configured to modify a polarization-dependent optical path length in the at least one of the first and second paths.

In some embodiments of the present invention, the optical imaging system operates using substantially unpolarized light. The birefringence controller may be further configured to have a single degree of freedom and wherein the single degree of freedom modifies a differential birefringence between the first path and the second path.

In further embodiments of the present invention, the controller may be configured to control the $\cos(\Delta a + \Delta b)$ term of the following spectral intensity equation:

$$S = 2[1 + \cos(\Delta a + \Delta b)\cos(k\Delta L)]$$

where S is the spectral intensity, $\cos(k\Delta L)$ is an interference term and $\cos(\Delta a + \Delta b)$ is a signal fading term.

Still further embodiments of the present invention provide methods of imaging. Substantially unpolarized light is provided to first and second optical paths of an optical imaging system.

In some embodiments of the present invention, a polarization-dependent optical path length is modified in at least one of the first and second paths of the optical imaging system.

In further embodiments of the present invention, an optical power in a frequency band that is a subset of a total spectrum of the light source may be measured. In certain embodiments of the present invention, incident power may be measured over a time interval.

In still further embodiments of the present invention, substantially unpolarized light may be received from a substantially unpolarized light source to provide the substantially unpolarized light.

In some embodiments of the present invention, polarized light may be received from a polarized light source. The received polarized light may be substantially depolarized to provide the substantially unpolarized light.

In further embodiments of the present invention, the light may be depolarized by substantially depolarizing the light for all wavelengths and times, depolarizing the light using a wavelength-average and/or depolarizing the light using a time-average.

DETAILED DESCRIPTION OF THE INVENTION

Figure 1A:
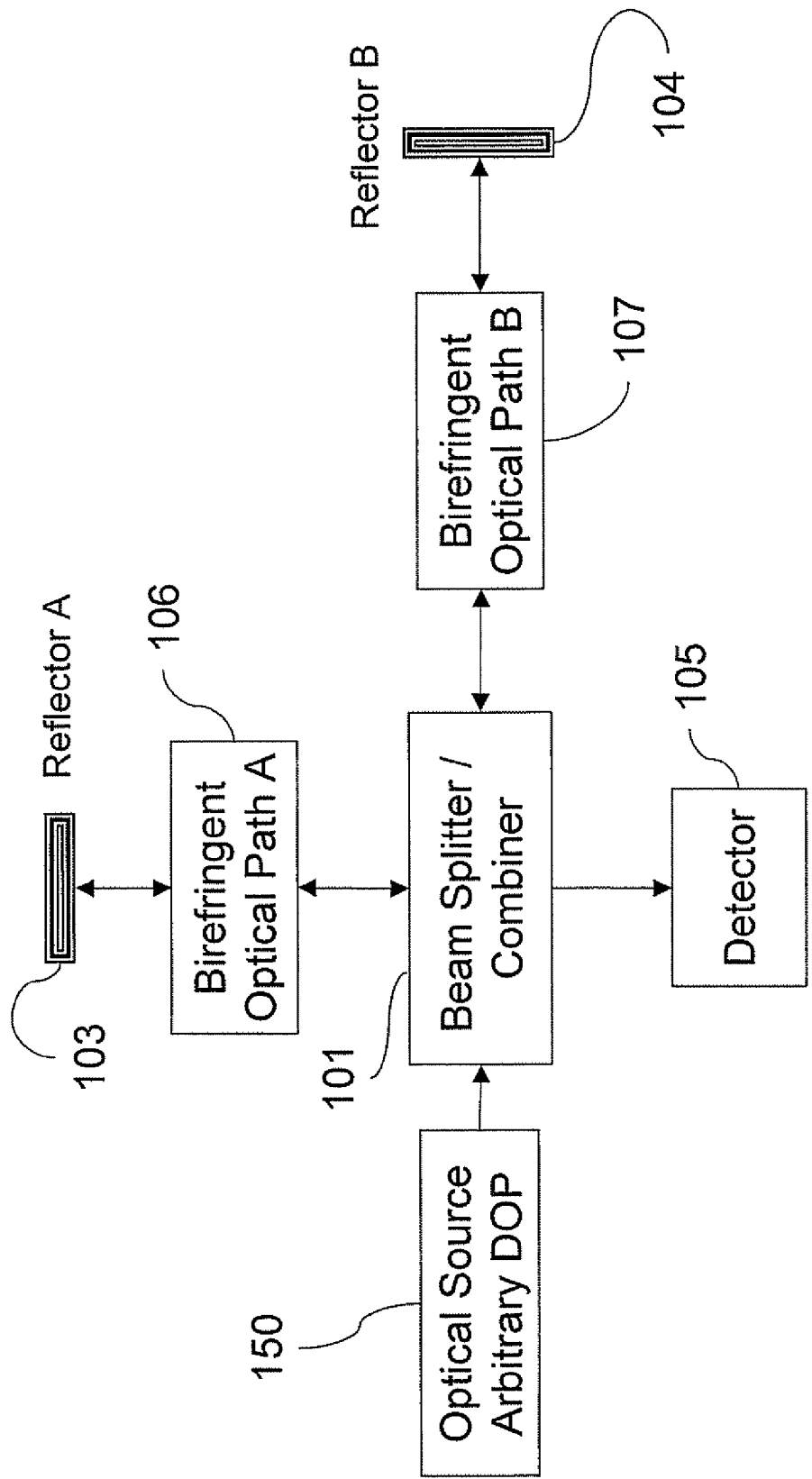
FIG. 1A is a schematic block diagram illustrating a conventional Michelson interferometer having birefringent optical paths.

Specific exemplary embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the particular exemplary embodiments illustrated in the accompanying drawings is not intended to be limiting of the invention. In the drawings, like numbers refer to like elements.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items. Dotted lines used in the figures depict optional elements therein.

It will be understood that although the terms first and second are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Figure 2A:
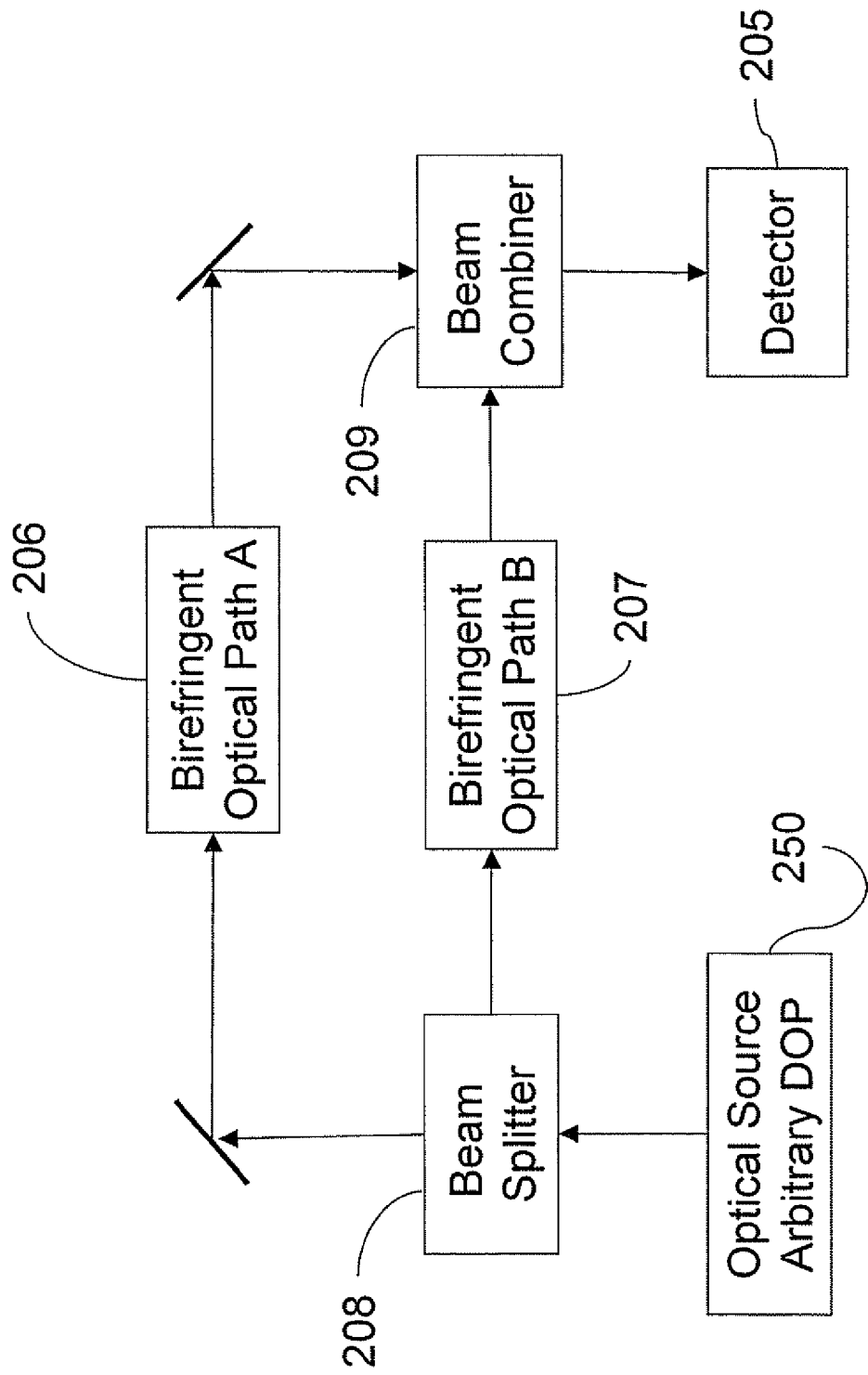
FIG. 2A is a schematic block diagram illustrating a conventional Mach-Zehnder interferometer having birefringent optical paths.

As discussed further herein with respect to FIGS. 4 through 26, some embodiments of the present invention provide optical interferometry systems that include birefringence in one or both of two interfering paths, as illustrated in FIG. 1A for a Michelson configuration and in FIG. 2A for a Mach-Zehnder configuration. These birefringent optical interferometry configurations are among common configurations for waveguide-based, including optical fiber waveguide-based, interferometers.

Figure 1B:
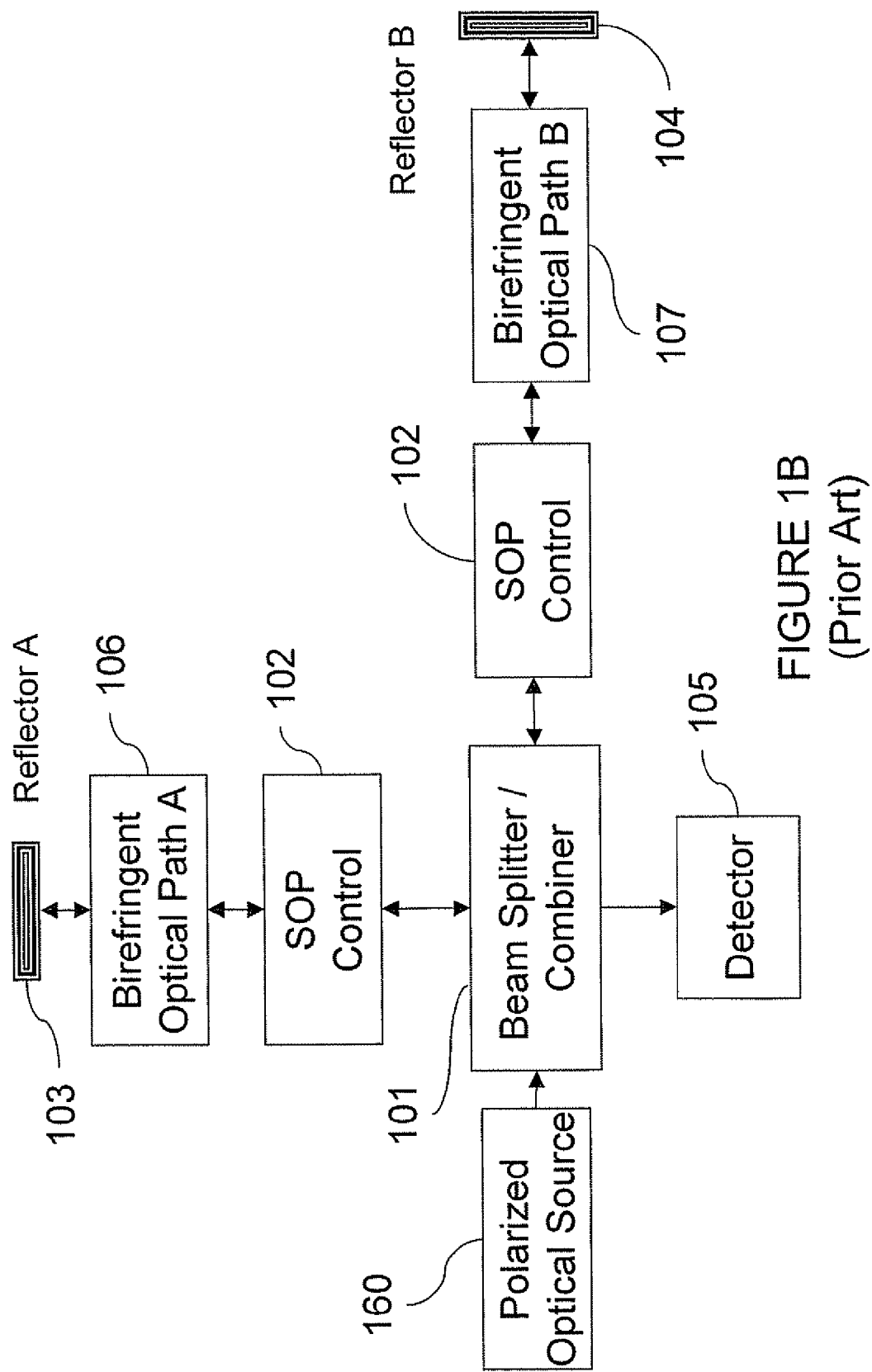
FIG. 1B is a schematic block diagram illustrating a conventional Michelson interferometer having birefringent optical paths and polarization control.
Figure 2B:
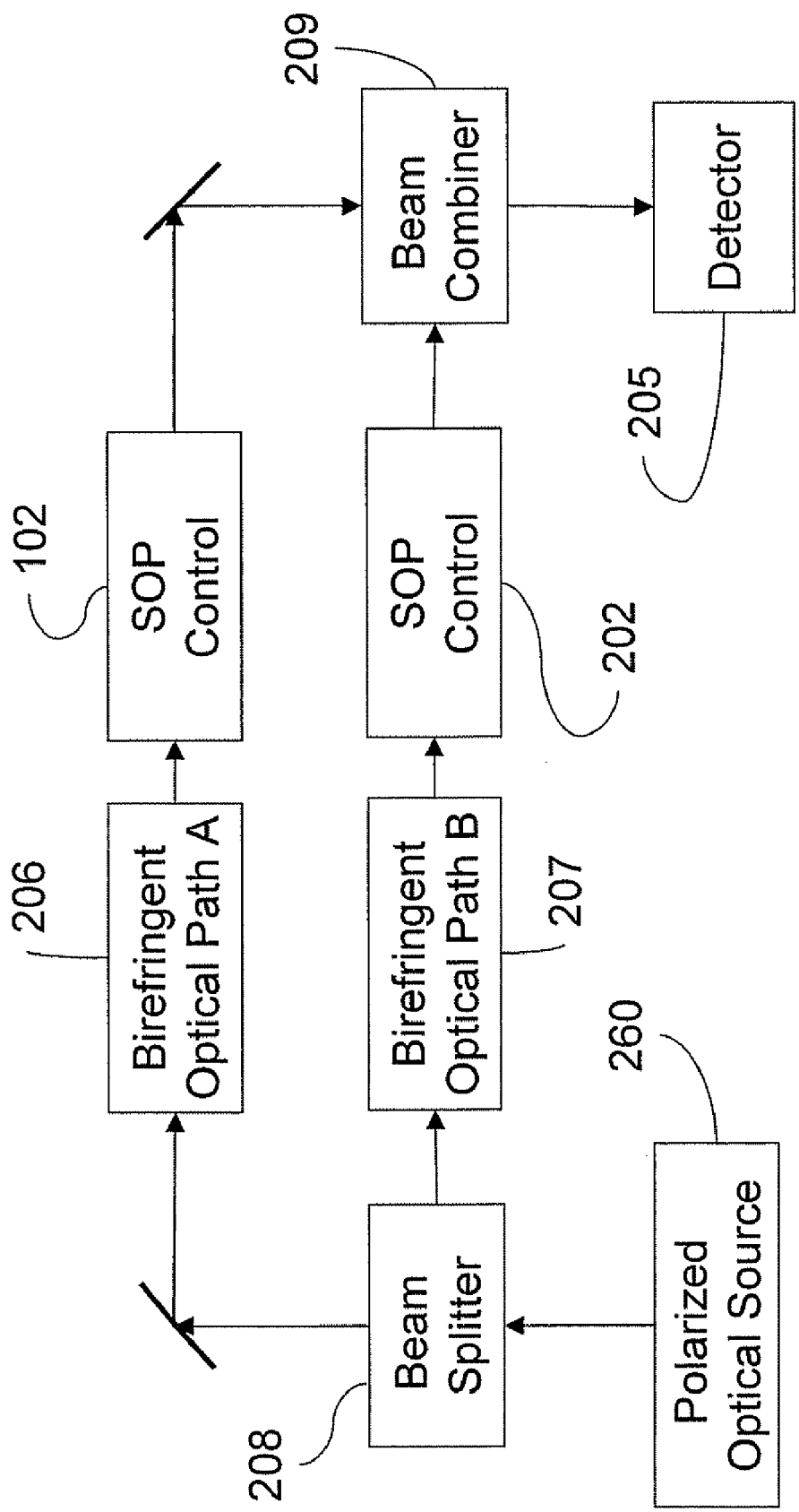
FIG. 2B is a schematic block diagram illustrating a conventional Mach-Zehnder interferometer having birefringent optical paths and polarization control.

Some embodiments of the present invention provide birefringent optical interferometry systems that include unpolarized light sources to reduce or eliminate the polarization fading effects due to differential polarization evolution in the interfering paths, or to polarization dependent reflection of a sample being measured/imaged. The use of a depolarizer may replace all of the polarization controllers illustrated in FIGS. 1B and 2B with an unpolarized source, or a partially polarized or polarized source that may be followed with one or more depolarizer(s), which may be adjusted once (or not at all) at time of manufacture and may result in a system that is much less sensitive to thermal variations or mechanical disturbances of the optical system, or polarization dependences of references or samples.

Some embodiments of the present invention provide for birefringence controllers to further reduce static or time-dependent polarization fading. Birefringence controllers have fewer degrees of freedom than state-of-polarization (SOP) controllers, and therefore may provide for simpler optimization of interferometric sensitivity in birefringent interferometers than in possible with polarization controllers as will be discussed further below.

Some embodiments of the present inventions provide for nominally single-frequency birefringent optical interferometers that utilize nominally unpolarized light sources. Such interferometers are typically applied to the measurement of path length differences or changes at a fraction of a wavelength of the light source.

Some embodiments of the present inventions provide for broadband, low-coherence, or white-light birefringent optical interferometers that utilize nominally unpolarized light sources. Such interferometers are typically applied to the measurement of path length differences or changes at a fraction of the coherence-length of the light source.

Some embodiments of the present inventions provide for broadband, low-coherence, or white-light birefringent optical interferometers that utilize nominally unpolarized light sources for the purposes of measurements or for imaging or for combinations of measurement and imaging.

Some embodiments of the present inventions provide for Optical Coherence Tomography (OCT) systems that utilize substantially unpolarized light. OCT embodiments may include, for example, time-domain or Fourier-domain, swept-source, spectral-domain or spectral radar.

OCT embodiments of the present invention may be applied to monochomatic or broadband interferometers in Michelson or Mach-Zehnder configurations, among others, for imaging or measurements.

Figure 3:
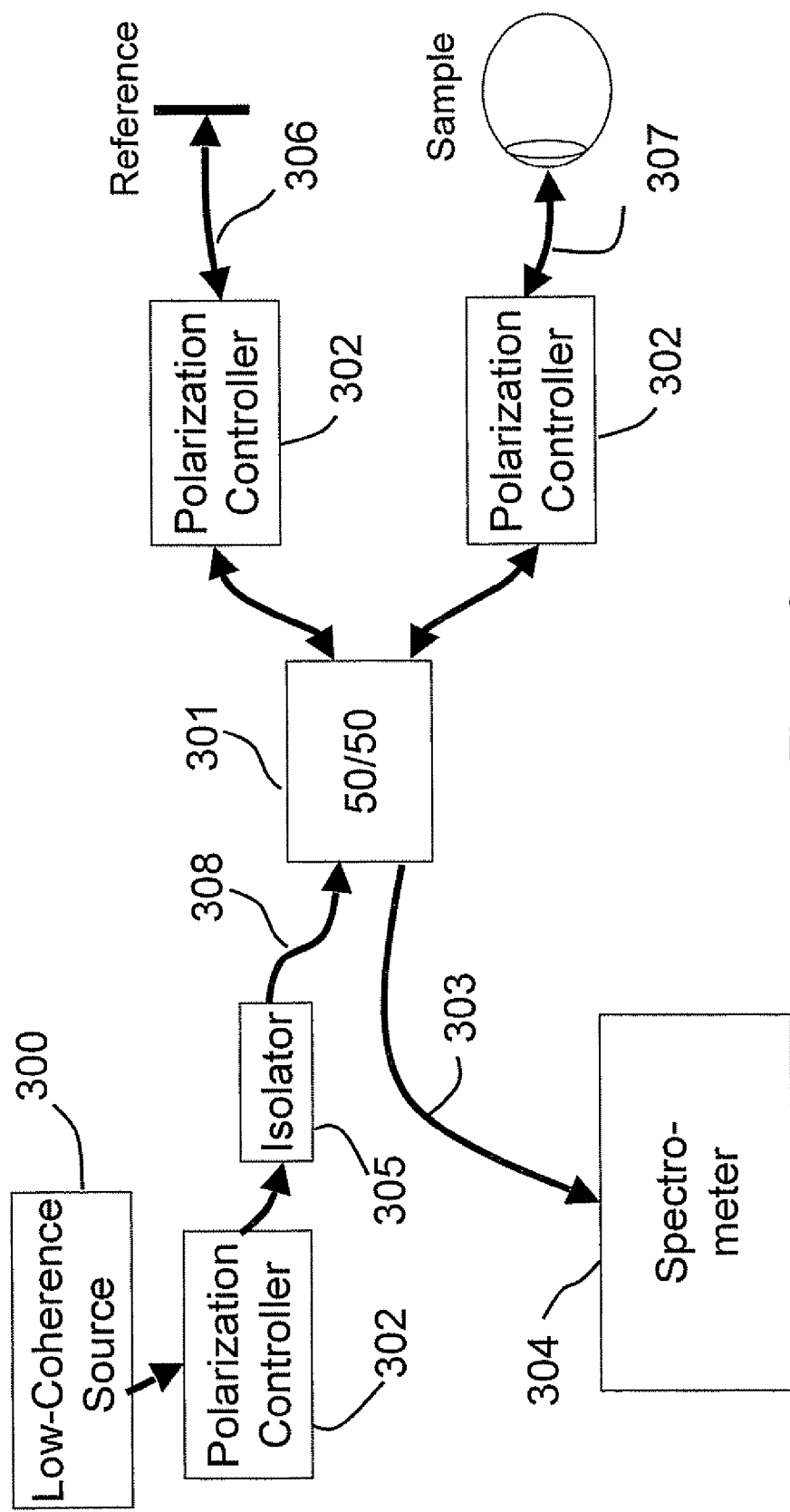
FIG. 3 is a schematic block diagram illustrating a conventional optical engine (system).

Some embodiments of the present invention provide optical systems (engines) for OCT that include unpolarized light sources and/or depolarizers to reduce or even eliminate the polarization effects of optical components in the system or the polarization dependent reflection of a sample being measured/imaged. The use of a depolarizer may replace all of the polarization controllers illustrated in, for example, FIG. 3, with a depolarizer(s), which may be adjusted once (or not at all) at time of manufacture and may result in a system that is much less sensitive to thermal variations or mechanical disturbances of the optical system.

In some embodiments of the present invention, the OCT engine may include a light source, an interferometer with a source arm, a detector arm, a reference arm and a sample arm, and a detector apparatus. The depolarizer may be placed in the source arm between the source and the interferometric coupler. The OCT engine systems may include light sources, such as superluminescent light-emitting diodes (SLED's) that typically produce light that is partially polarized, and/or tunable lasers, which produce light that is typically highly polarized. The addition of a depolarizer according to some embodiments of the present invention reduces the degree of polarization of the source light by increasing the likelihood that the light radiation is distributed across polarization states.

The performance of a depolarizer can be measured by the degree of polarization (DOP) where 100% indicates light with a single state of polarization (SOP) and 0% indicates perfectly unpolarized light, i.e., where all polarizations are present in equal amounts. DOP is defined as the ratio of the power of the polarized light to the total power. For example, passing light through an ideal polarizer would typically produce light with 100% DOP. Conversely, an ideal depolarizer would typically produce light with 0% DOP. However, for some embodiments of the present invention, perfect depolarization is not required.

The maximum system optical-signal-to-noise ratio (OSNR) will generally occur when the light returning from the sample arm and the light returning from the reference arm have the same state of polarization (SOP). This can be achieved in several ways. Current systems typically use substantially polarized light and one or more polarization controllers in the reference and/or sample arms to increase the likelihood that that the polarizations are aligned (or have the same SOP) where the interferometric mixing occurs. The interferometric signal power will generally be proportional to the electric field strength from the reference arm, the electric field strength from the signal arm and the square of the cosine of the angle between the two SOPs as seen in the following equation:

$$\text{Signal\_strength} = E_{sample} * E^*_{reference} * \cos^2\theta \quad (1)$$

This generally can vary from 1, for perfectly aligned SOPs, to 0, for SOPs that are at right angles. Thus, when the two SOPs are most nearly aligned the maximum signal strength may be provided.

Furthermore, the light from the source can be largely depolarized before it is sent down the reference and sample arms. In these embodiments, polarization effects in the two arms may be less important as any polarization effects in the two arms will be averaged over all of the available polarization states. As long as there is a high degree of depolarization (low DOP) it will be expected that there will be minimal impact to the system signal strength as illustrated in the approximate form of the following equation:

$$\text{Signal\_strength} = E_{sample} * E^*_{reference} * [1 + DOP^2 * (\cos^2\theta - 1)] \quad (2)$$

Equation 2 assumes the same DOP for the sample power and the reference power.

Figure 4:
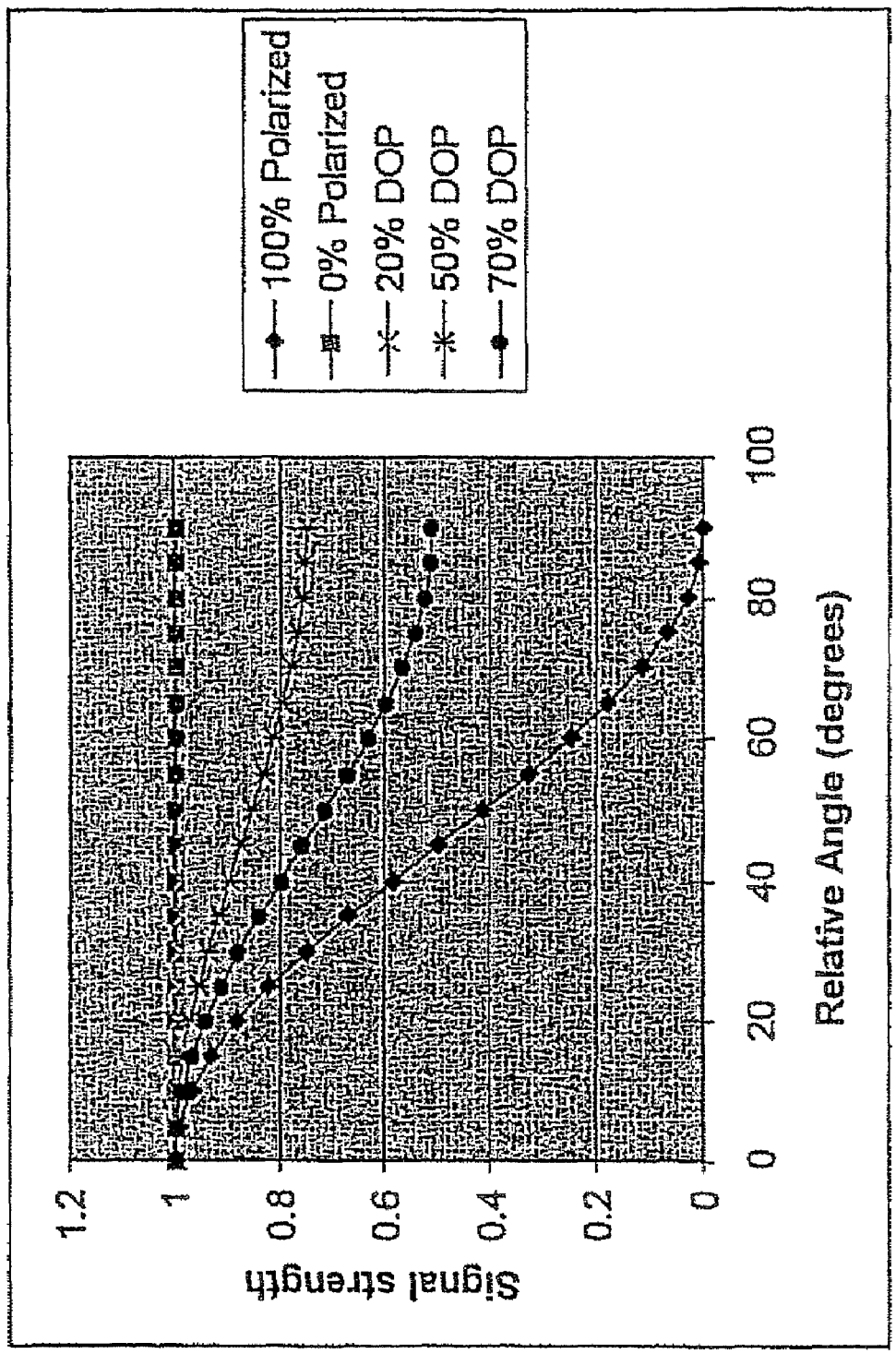
FIG. 4 is a graphical illustration of signal strength versus relative angle for different polarizations according to some embodiments of the present invention.

Illustrative curves for these equations are illustrate in FIG. 4. As illustrated in FIG. 4, for highly polarized light (100% Polarized), the signal strength falls off rapidly with the angle between the polarization of the reference and signal light. For highly unpolarized light (0% Polarized), the angle has no effect on the signal strength as expected. However, even if the light is only partially depolarized, the impact of the relative angle is substantially reduced. For 20% polarized light, the worst-case signal loss is only 4% and, even for light that is 50% polarized, the signal loss is 25%.

As discussed above, Equation 2 is an approximate form that is informative, but may have limited validity in real world systems where differential birefringence between two interfering paths may lead to polarization fading even with unpolarized light.

A complete theory of interference has been derived for two optical signals of arbitrary coherence and polarization state, each traveling a distinctly different path with arbitrary birefringence, polarization dependent loss and optical path length. The correlation functions are calculated for a complete set of polarization states in terms of the coherence of the source fields. The model is validated against simple and known cases. Furthermore, the impact of differential birefringence is analyzed. Fading of fringe visibility is readily visible from the resultant equations. Regardless of input polarization state, visibility fading can be controlled and eliminated using an active control system to manage the differential birefringence between the two paths.

A system model of propagation will now be discussed. Consider two different monochromatic sources (same wavelength) of arbitrary degree and state of polarization, and arbitrary self and mutual coherence. Each source travels down a separate path each with different length, birefringence, and polarization-dependent loss. There is no polarization mode mixing in the fiber as discussed in W. K. Burns, JLT 10, 992, 1992. In some embodiments of the present invention, effects induced by OCT sample scattering, such as change of polarization, coherence, or signal power may also be addressed without departing from the scope of the present invention.

Each path in the system is described by a series of matrices as set out in the following equation:

$$\vec{E}_j = \vec{L}(L_j)\vec{B}_b(\delta_{bj})\vec{P}(\theta_j,\epsilon_j)\vec{B}_a(\delta_{aj})\vec{E}_{sj} \quad (3)$$

where the vectors $\vec{E}_{sj}$ and $\vec{E}_j$ are the input (source) and output fields of path j as $$\vec{E}_{sj} = \begin{bmatrix} E_{sj}^x \\ E_{sj}^y \end{bmatrix} \qquad (4A, B)$$

$$\vec{E}_j = \begin{bmatrix} E_j^x \\ E_j^y \end{bmatrix}$$

The unitary matrix $\vec{L}$ describes average phase accumulation along the path of length $L_j$ as illustrated by the following equation:

$$\vec{L}(L_j) = e^{ikL_j} \begin{bmatrix} 1 & 0 \\ 0 & 1 \end{bmatrix} \qquad (5)$$

Two matrices $\vec{B}$ describe the total birefringence $\delta_{aj}+\delta_{bj}$ of the path as:

$$\vec{B}_a(\delta_{aj}) = \begin{bmatrix} e^{i\delta_{aj}/2} & 0 \\ 0 & e^{i\delta_{aj}/2} \end{bmatrix} \qquad (6A, B)$$

$$\vec{B}_b(\delta_{bj}) = \begin{bmatrix} e^{i\delta_{bj}/2} & 0 \\ 0 & e^{i\delta_{bj}/2} \end{bmatrix}$$

In order to account for polarization dependent loss (PDL, a polarizing effect), a polarizer of arbitrary strength lies in between these two sections of birefringence at angle $\theta_j$ and extinction $\delta_j$, given by the following equation:

$$\vec{P}(\theta_j, \varepsilon_j) = \qquad (7)$$
$$\begin{bmatrix} \cos^2(\theta_j) + \varepsilon_j\sin^2(\theta_j) & (1-\varepsilon_j)\cos(\theta_j)\sin(\theta_j) \\ (1-\varepsilon_j)\cos(\theta_j)\sin(\theta_j) & \varepsilon_j\cos^2(\theta_j) + \sin^2(\theta_j) \end{bmatrix}$$

Note that the case of no polarizer is obtained by setting $\varepsilon=1$, in which case $\vec{P}$ becomes a simple unitary matrix.

Evaluating Equation (3) with the help of Equations (4A)-(7) yields the field at the output path references to the input fields as:

$$\vec{E}_j = e^{ikL_j} e^{i(\delta_{aj}+\delta_{bj})/2} \qquad (8)$$
$$\begin{bmatrix} \cos^2(\theta_j) + \varepsilon_j\sin^2(\theta_j) & e^{-i\delta_{aj}}(1-\varepsilon_j)\cos(\theta_j)\sin(\theta_j) \\ e^{-i\delta_{bj}}(1-\varepsilon_j)\cos(\theta_j)\sin(\theta_j) & e^{-i(\delta_{aj}+\delta_{bj})}\varepsilon_j\cos^2(\theta_j) + \sin^2(\theta_j) \end{bmatrix} \vec{E}_{sj}$$

The power contained in this field can be derived as:

$$|\vec{E}_j|^2 = \{[\cos^2(\theta_j) + \varepsilon_j\sin^2(\theta_j)]^2 + (1-\varepsilon_j)^2\cos^2(\theta_j)\sin^2(\theta_j)\}|E_s^x|^2 + \qquad (9)$$
$$\{[\varepsilon_j\cos^2(\theta_j) + \sin^2(\theta_j)]^2 + (1-\varepsilon_j)^2\cos^2(\theta_j)\sin^2(\theta_j)\}|E_s^y|^2 +$$
$$2(1-\varepsilon_j^2)\cos(\theta_j)\sin(\theta_j)\text{Re}\{e^{i\delta_{aj}}E_s^x E_s^{y*}\}$$

The first and second terms are the intensity of the x- and y-polarized components, respectively, while the third term represents the interference between the polarizations due to polarization mixing in the path via polarizer. Note that in the absence of any polarizer ($\varepsilon=1$), the intensity simplifies to the sum of the intensities of each polarization component. For a perfect polarizer ($\varepsilon=0$), the resultant intensity reduces to Malus' law (cosine-squared dependence on the polarizer angle).

The interference of two independent paths will now be discussed. Applying this formulation to two separate arms, the outputs are mixed through the spectral density as:

$$S = \langle \vec{E} * \vec{E} \rangle \qquad (10)$$

where the vector $\vec{E}$ is the sum of the two fields that propagate through different paths 1 and 2, and the brackets denote ensemble averaging. Straightforward application of Equation (8) into Equation (10) leads to a spectral density of the form:

$$S = (S_{11}^{xx} + S_{11}^{yy} + S_{11}^{xy}) + (S_{22}^{xx} + S_{22}^{yy} + S_{22}^{xy}) + (S_{12}^{xx} + S_{12}^{yy} + S_{12}^{xy} + S_{12}^{yx}) \qquad (11)$$

The first two bracketed terms in Equation (11) are the background terms involving the coherence of each source with itself, including coherence across orthogonal polarizations, and are given by the following equations:

$$S_{jj}^{xx} = (P_j^{x2} + P_j^{c2})W_{jj}^{xx} \quad S_{jj}^{yy} = (P_j^{y2} + P_j^{c2})W_{jj}^{yy} \qquad (12A,B)$$

$$S_{jj}^{xx} = 2(P_j^x + P_j^y)P_j^c \text{Re}\{e^{i\delta_{aj}}W_{jj}^{xy}\} \qquad (13)$$

The final bracketed terms in Equation (11) give rise to interference between the two arms of the interferometer and are given by the following equations:

$$S_{12}^{xx} = 2\text{Re}\{e^{ik\Delta L}e^{i(\Delta_a+\Delta_b)}(P_1^x P_2^x + e^{-2i\Delta_b}P_1^c P_2^c)W_{12}^{xx}\} \qquad (14)$$

$$S_{12}^{yy} = 2\text{Re}\{e^{ik\Delta L}e^{-i(\Delta_a+\Delta_b)}(P_1^y P_2^y + e^{2i\Delta_b}P_1^c P_2^c)W_{12}^{yy}\} \qquad (15)$$

$$S_{12}^{xy} = 2\text{Re}\{e^{ik\Delta L}e^{-i\Sigma_a}(e^{i\Delta_b}P_1^x P_2^c + e^{-i\Delta_b}P_2^y P_1^c)W_{12}^{xy}\} \qquad (16)$$

$$S_{12}^{yx} = 2\text{Re}\{e^{ik\Delta L}e^{i\Sigma_a}(e^{i\Delta_b}P_2^x P_1^c + e^{-i\Delta_b}P_1^y P_2^c)W_{12}^{yx}\} \qquad (17)$$

In Equations (12)-(17), the polarizer terms are defined by the following equations:

$$P_j^x = \cos^2(\theta_j) + \varepsilon_j\sin^2(\theta_j) \quad P_j^y = \varepsilon_j\cos^2(\theta_j) + \sin^2(\theta_j) \qquad (18A,B)$$

$$P_j^c = (1-\varepsilon_j)\cos(\theta_j)\sin(\theta_j) \qquad (19)$$

while the birefringence terms are defined by the following equations:

$$\Delta_a = (\delta_{a2}-\delta_{a1})/2 \quad \Delta_b = (\delta_{b2}-\delta_{b1})/2 \qquad (20A,B)$$

$$\Sigma_a = (\delta_{a2}+\delta_{a1})/2 \quad \Delta L = (L_2-L_1) \qquad (21A,B)$$

The field correlations are the ensemble averages of the source fields, given by the following equation:

$$W_{ij}^{kl} = \langle E_{si}^{k*} E_{sj}^l \rangle \qquad (22)$$

Incident fields and correlations will now be discussed. Incident fields of various polarization states and their respective self-correlations are given in Table 1 set out below. As illustrated in Table 1, the x correlation is defined as $\langle |\hat{x} \cdot \vec{E}|^2 \rangle$, where $\hat{x}$ is the direction unit vector. The y correlation has a similar definition, and the cross correlation is defined as $\langle (\hat{x} \cdot \vec{E})(\hat{y} \cdot \vec{E}^*) \rangle$. These electrical fields relate to the fields given in Equation (4A,B) by simple dot product with the appropriate unit vector.

TABLE 2

Polarizer terms for simple cases.

| Polarizer term | x-polarization ($\epsilon_j = 0$) | y-polarization ($\epsilon_j = 0$) | no polarizer ($\epsilon_j = 1$) |
|---|---|---|---|
| $P_j^x$ | 1 | 0 | 1 |
| $P_j^y$ | 0 | 1 | 1 |
| $P_j^c$ | 0 | 0 | 0 |

TABLE 1

Electric field representations for various cases of polarized light.

| Type | Electric field | x-correlation | y-correlation | cross correlation |
|---|---|---|---|---|
| Unpolarized | $\vec{E} = \frac{1}{\sqrt{2}}(\hat{x}E_x + \hat{y}E_y)$ | $\frac{1}{2}\Gamma_{xx}$ | $\frac{1}{2}\Gamma_{yy}$ | 0 |
| Linear x | $\vec{E} = \hat{x}E_x$ | $\Gamma_{xx}$ | 0 | 0 |
| Linear y | $\vec{E} = \hat{y}E_y$ | 0 | $\Gamma_{yy}$ | 0 |
| Linear 45° | $\vec{E} = \frac{1}{\sqrt{2}}(\hat{x}E_x + \hat{y}E_y)$ | $\frac{1}{2}\Gamma_{xx}$ | $\frac{1}{2}\Gamma_{yy}$ | $\frac{1}{2}\Gamma_{xy}$ |
| Arbitrary Linear | $E = \hat{x}\cos(\theta_p)E_x + \hat{y}\sin(\theta_p)E_y$ | $\cos^2(\theta_p)\Gamma_{xx}$ | $\sin^2(\theta_p)\Gamma_{yy}$ | $\sin(\theta_p)\cos(\theta_p)\Gamma_{xy}$ |
| Circular | $E = \frac{1}{\sqrt{2}}(\hat{x}E_x + i\hat{y}E_y)$ | $\frac{1}{2}\Gamma_{xx}$ | $\frac{1}{2}\Gamma_{yy}$ | $\frac{1}{2}\Gamma_{xy}$ |
| Elliptical | $E = \hat{x}\cos(\theta_p)E_x + i\hat{y}\sin(\theta_p)E_y$ | $\cos^2(\theta_p)\Gamma_{xx}$ | $\sin^2(\theta_p)\Gamma_{yy}$ | $i\sin(\theta_p)\cos(\theta_p)\Gamma_{xy}$ |

In Table 1, $\theta_P$ is the angle of linear polarization or major axis of elliptical polarization. The coherence terms are given by the following equation:

$$\Gamma_{ij} = \frac{\langle E_i E_j^* \rangle}{\sqrt{|E_i|^2 |E_j|^2}} \quad (23)$$

and represent the self or mutual coherence of the relative field components. Therefore, Table 1 relates the $W_{ij}^{kl}$ terms directly to the coherence terms for a given polarization state. Cross correlation terms can be simply derived by using two distinct polarization terms in Table 1.

Mixed states of polarization can be obtained by a normalized superposition of the elements in Table 1, for example, partially-polarized can be a combination of linear polarized light and unpolarized light.

Validation of the model will now be discussed. In the analysis that follows, each path is assumed to have equal intensity at the input. Table 2 set out below summarizes Equations (18) and (19) for relatively simple polarizer cases, which will be useful in the following analysis.

First consider the simple case, analyzing orthogonal components in each path. Regardless of birefringence in the paths, the spectral density of Equation (11) reduces to a constant given by the following equation:

$$S = W_{11}^{xx} + W_{22}^{yy} \quad (24)$$

the value of which is dependent on the polarization of the incident field. The orthogonal components do not interfere, and no fringes are formed.

For the case where there are no polarizers (no PDL) and the birefringence in each path is identical, the spectral density of Equation (11) becomes:

$$S = (W_{11}^{xx} + E_{11}^{yy} + W_{22}^{xx} + W_{22}^{yy}) + 2(W_{12}^{xx} + W_{12}^{yy})\cos(k\Delta L) \quad (25)$$

Now under the assumption that the light in both paths originates from the same source of coherent ($\Gamma = 1$) linearly-polarized light, then the spectral density reduces to the familiar form given by the following equation:

$$S = 2[1 + \cos(k\Delta L)] \quad (26)$$

where the peak intensity is four times the intensity of a single beam and the fringes have unity visibility. Equation (26) also applies to the case of coherent but unpolarized light, provided $\Delta L$ is much shorter than the coherence length of the light. This result differs from that discussed in W. K. Burns (JLT 10, 992, 1992), which predicted and measured a visibility of 0.5 in a fiber gyroscope geometry. This discrepancy can be accounted for in that they assumed polarization mixing in the fiber, which is not present in our model. Adding this component may reduce the visibility by half, since the polarization mixing splits an equal amount of light from each uncorrelated polarization component of the source into each of the output polarizations of each path.

Differential birefringence will now be discussed. Now consider the case of an unpolarized, but coherent, source that is equally split down paths with different birefringence but no PDL. The resultant spectral intensity is given by:

$$S = 2[1 + \cos(\Delta a + \Delta b)\cos(k\Delta L)] \quad (27)$$

Equation (27) shows that differential birefringence in the paths will lead to fading of the interference fringes via the term $\cos(\Delta a + \Delta b)$. For a differential birefringence of $\pi/2$ between the two paths, the fringes vanish. Assuming that the birefringence varies on a time scale much shorter than the acquisition time of the system measuring the fringes, then the time-averaged spectral intensity is simply S=2 (the sum of the intensities of the individual paths), and all fringes have vanished.

It may be desirable to mitigate the fading effects of differential birefringence. Consider the use of linearly-polarized light with a polarization angle that differs from the axis of birefringence. In this case, the spectral density takes on the form:

$$S = 2[1 + \cos(k\Delta L + \Delta a + \Delta b)] + 4\sin^2(\theta_p)\sin(\Delta a + \Delta b)\sin(k\Delta L) \quad (28)$$

Figure 5:
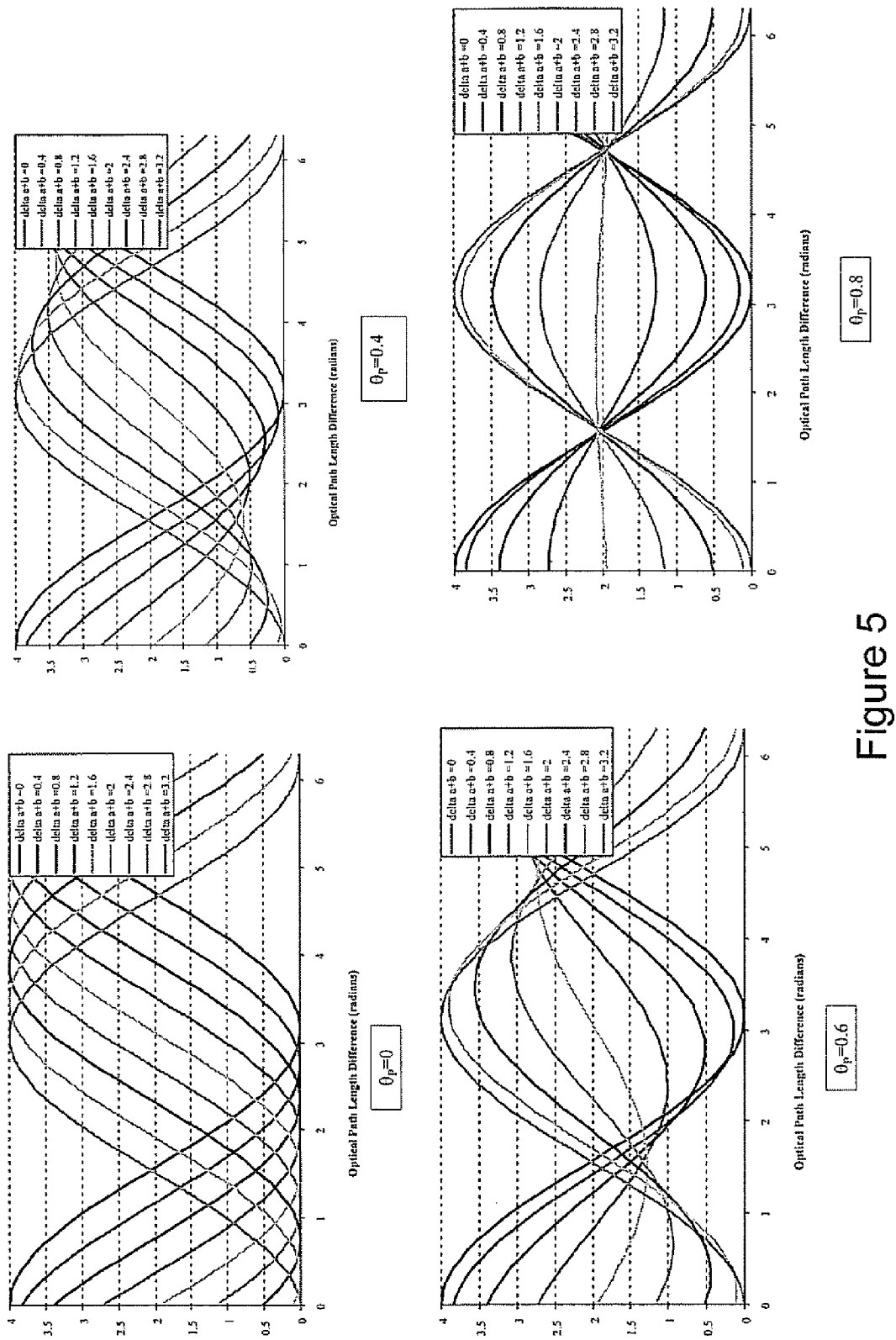
FIG. 5 is a plurality of graphs illustrating spectral density vs. optical path length difference for various differential birefringence and polarization angles according to some embodiments of the present invention.

In the first term, the differential birefringence adds an offset to the fringes, but does not contribute to fading. There is a second interference term that has fading associated with it whose strength is dependent on the relative angle between the source polarization angle and the birefringent axis. Although as written it looks like a separate term that might be sifted away from the signal, it is in fact deterministically coupled via the same arguments. This term in fact serves to reduce the fringe visibility as illustrated in FIG. 5. In the four plots illustrated in FIG. 5, the curves represent spectral density as a function of optical path length difference. The different curves represent different values of differential birefringence, while the four plots are different value of the polarization angle. From these plots, it is clear that drifting birefringence and relative polarization angle (with respect of the birefringent axis) will lead to complete signal fading.

If the polarization of the incoming light could be actively aligned to the birefringent axis, then the second interference term in Equation (28) would vanish, as is evidenced in the upper left plot of FIG. 5. Alternatively, the polarization (or birefringent axis) could be swept more rapidly than the acquisition time of the measurement system in order to reduce the effect of this term. This concept gives rise to behavior that is qualitatively similar to the lower right plot in FIG. 5, since the impact of the sin-squared term yields one-half (effectively unpolarized light). Mathematically, the spectral density in this case reduces to unity (i.e. the fringes vanish) for a differential birefringence of $\pi/4$.

Thus, in summary, a complete theory of interference has been derived for two optical signals of arbitrary coherence and polarization state, each traveling a distinctly different path with arbitrary birefringence, polarization dependent loss, and optical path length. The correlation functions were calculated for a complete set of polarization states in terms of the coherence of the source fields. The model was validated against simple and known cases. Further, the impact of differential birefringence was analyzed. Fading of fringe visibility was readily visible from the resultant equations. With polarized light, two degrees of freedom are required to eliminate polarization fading; in the terminology of this analysis, the two degrees of freedom are the angle that polarized light makes with respect to a birefringence axis, and the differential birefringence between the two paths. With unpolarized, or equivalently unpolarized light, the number of degrees of freedom required to minimize polarization fading reduces to one: the differential birefringence between the two paths as will be discussed further herein.

Depolarization can be achieved in at least three different ways according to some embodiments of the present. In some embodiments of the present invention, the light may be fully depolarized for all wavelengths and times.

In further embodiments of the present invention, the light may be effectively depolarized in a wavelength-averaged sense, taking advantage of the fact that any photodiode typically integrates over a bandwidth of light and not just a single wavelength. Thus, if a distribution of polarization states exists within the optical bandwidth of a detector, the light may appear effectively depolarized to that detector.

Wavelength-averaged depolarization can be accomplished by, for example, using a Lyot depolarizer, where wavelength-dependent birefringence in an optical path is used to create a well-distributed wavelength-dependence of polarization.

In still further embodiments of the present invention, the light may be effectively depolarized in a time-averaged sense taking advantage of the fact that any photodiode integrates over a finite period of time. Thus, if a distribution of polarization states exists within the electrical bandwidth of a detector, the light may appear effectively depolarized to that detector.

Time-averaged depolarization can be accomplished by, for example, using a polarization scrambler where the time to cycle through the various polarization states is on the same order or less than the integration time of the photodiode.

Depolarizers can be built in a variety of ways and various such depolarizer designs may be utilized in embodiments of the present invention. In some embodiments of the present invention, a depolarizer design is used that provides a high enough level of depolarization of the light seen by any single detector in the system. In general, unpolarized light is characterized by a light field that may be decomposed into two orthogonal polarizations, where the fields of the orthogonal polarizations are phase un-correlated, and where the intensities of the two orthogonal polarizations are equal, and where these conditions hold independent of basis set chosen for the polarization decomposition. In general, a device for depolarizing a substantially polarized light source may include: a) a device for splitting an incident light source into two paths, b) a path length difference greater than the coherence length of the light source with respect to the detection bandwidth (optical or electrical), c) a polarization controller to orient the polarizations at the output of the two paths such that the two resultant light fields are substantially orthogonal to each other and d) a variable optical attenuator (VOA) to match the power levels of the two resultant light fields.

Figure 6:
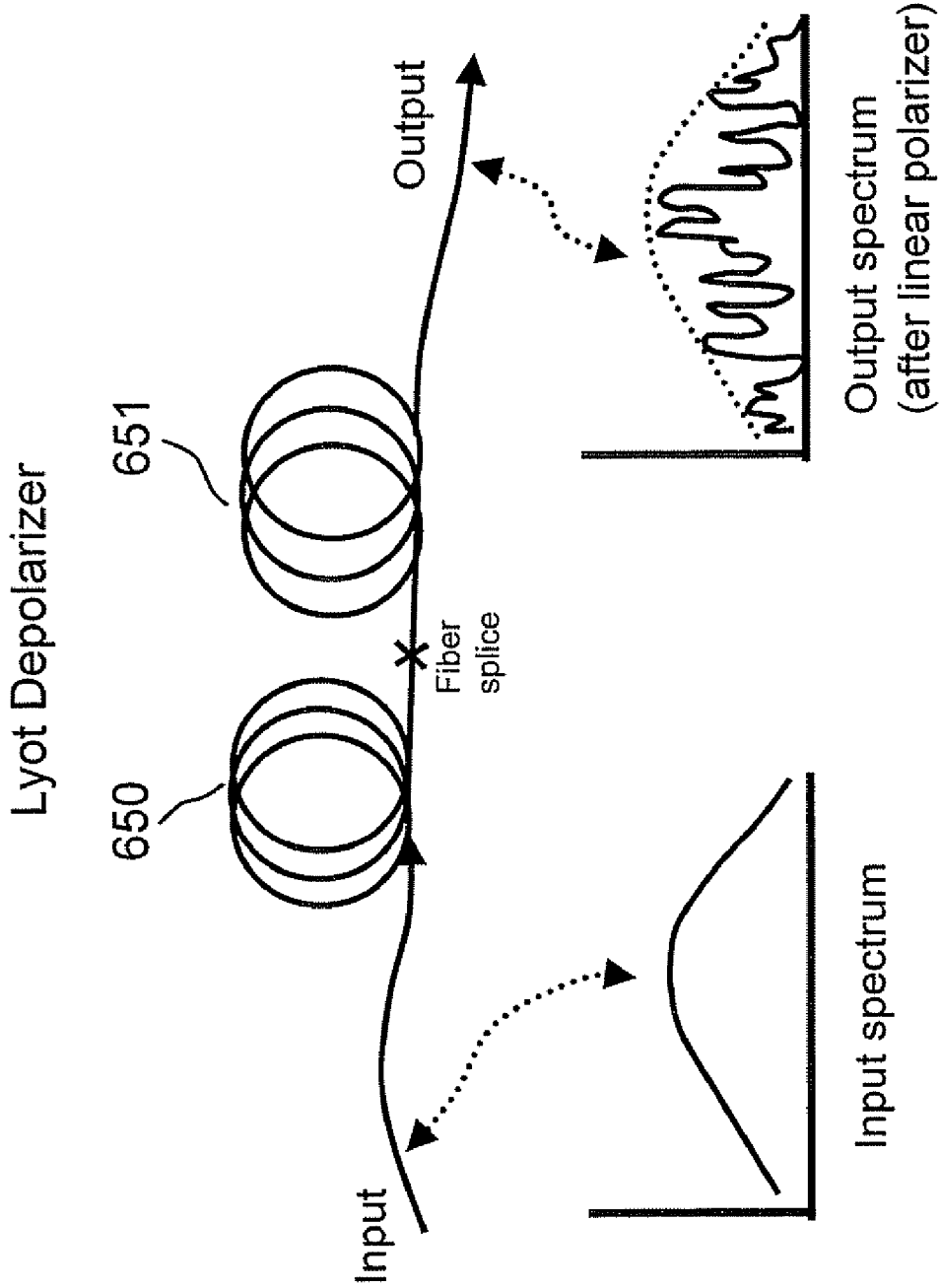
FIG. 6 is a schematic block diagram of a Lyot-type optical depolarizer according to some embodiments of the present invention.

One type of depolarizer is a fiber Lyot depolarizer, which consists of two sections of birefringent fiber spliced together. A Lyot depolarizer generally does not depolarize the light at a single wavelength, but rather produces different polarizations at different wavelengths. As long as the detector integrates over a sufficient optical bandwidth, the light will on average behave as depolarized. A characteristic of a Lyot depolarizer is the size of the bandwidth required for the light to appear depolarized. In general the longer the fiber in the Lyot depolarizer, the narrower the bandwidth required for the light to appear depolarized. In some embodiments of the present invention, the relevant bandwidth is the range of wavelengths detected by a single photodiode. A Lyot depolarizer is illustrated in FIG. 6.

Figure 7:
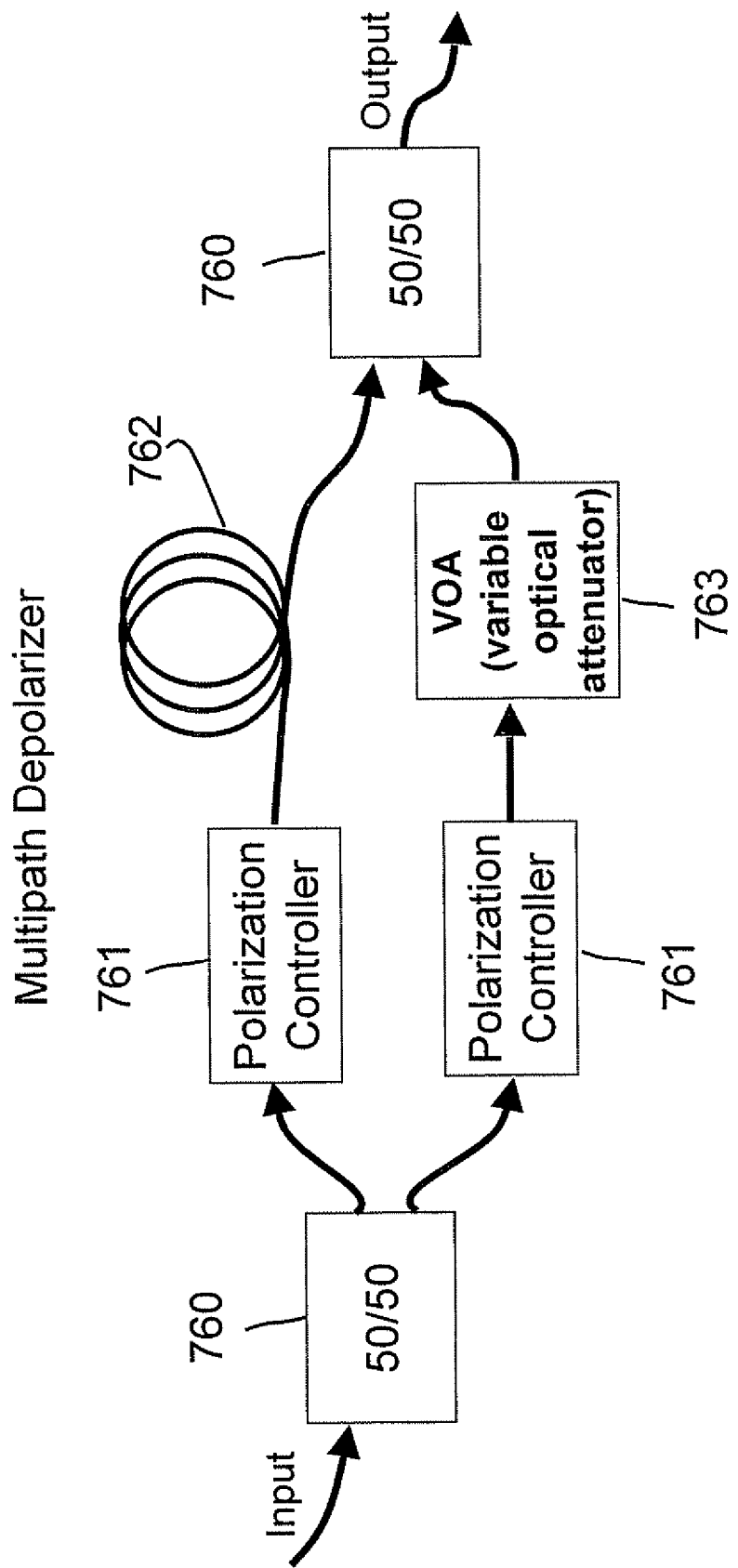
FIG. 7 is a schematic block diagram of a multipath optical depolarizer according to some embodiments of the present invention using polarization control, variable optical attenuators, and fixed coupler.

A second general architecture/design for a depolarizer is illustrated in FIG. 7. Here the optical power is split by a 50%/50% power coupler. One leg of a first 50%/50% power coupler 760 is connected to a polarization controller 761, then to a length of fiber 762 and finally to a second 50%/50% power coupler 760. The other leg is connected to a second polarization controller 761, then to a variable optical attenuator (VOA) 763 and finally to the other leg of the second 50%/50% power coupler 760. The polarization controllers are set so that the light passing through each leg is rotated 90 degrees with respect to the light in the other leg. The fiber coil in the first leg should be longer than the coherence length observed by any individual detector in the system and may ensure that the light coming from each of the two legs is incoherent with respect to the other leg. Finally the VOA on the second leg may be used to ensure that the power out of each leg is equal. Note that, in some embodiments, this configuration is provided with just one polarization controller and also may be provided with a VOA in each path (two VOAs instead of one) to accurately match the power levels on each leg. This configuration in some embodiments may produce highly unpolarized light (low DOP).

Figure 8:
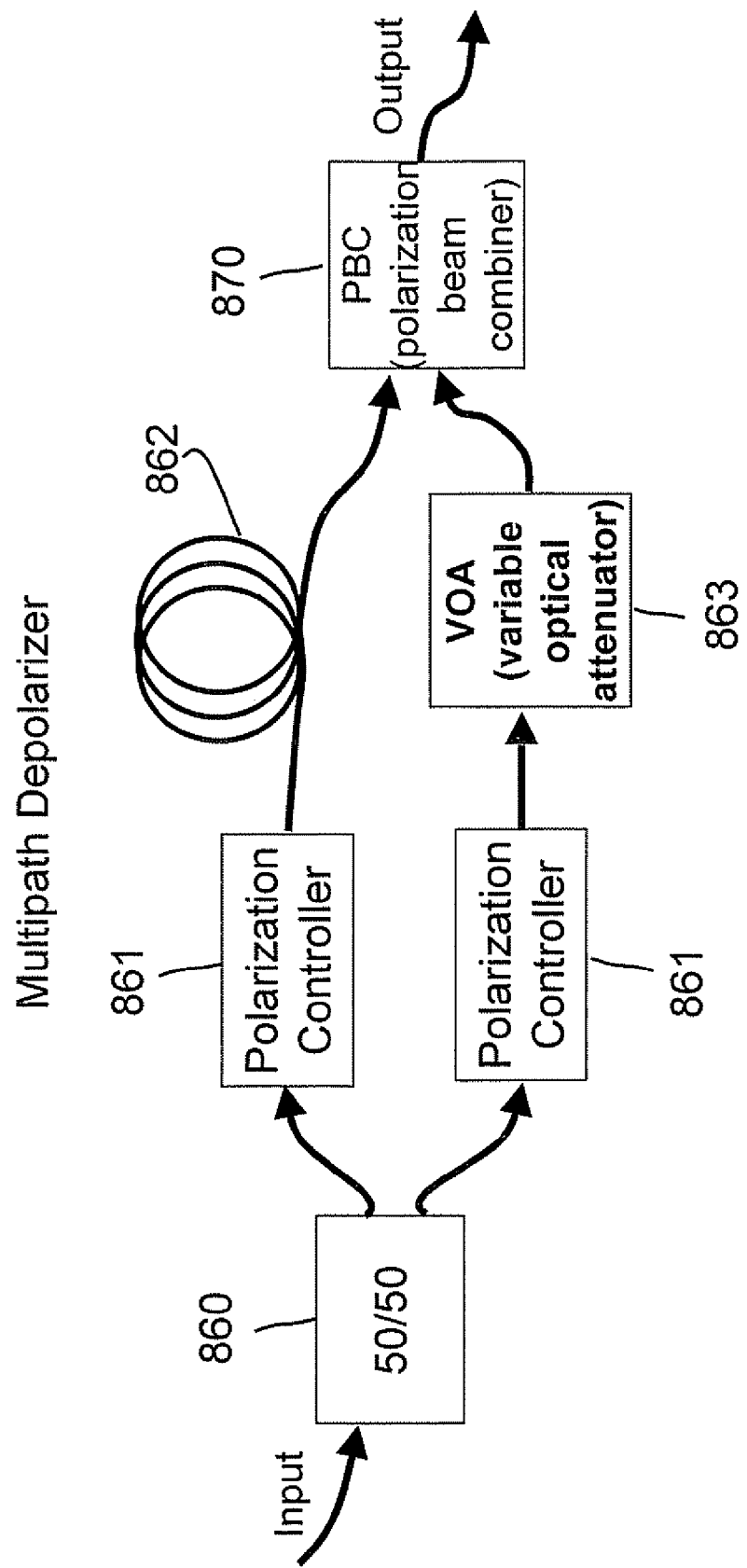
FIG. 8 is a schematic block diagram of a multipath optical depolarizer according to some embodiments of the present invention using polarization control, variable optical attenuator, and polarization beam combiner.

As a modification of the depolarizer architecture shown in FIG. 7, another architecture/design is illustrated in FIG. 8. As illustrated in FIG. 8, a polarization beam combiner (PBC) 870 is used instead of a 50%/50% power coupler. The PBC 870 may ensure that the polarizations on the two legs are orthogonal and the PBC typically has lower insertion loss that a power coupler. Two polarization controllers are used in this architecture because the polarization in each leg is matched with the transmitted polarization state for the respective inputs to the PBS. The polarization controllers can be used as VOAs in this configuration, eliminating the additional VOAs in each leg. It is still desirable that the paths through each leg vary in length by a distance longer than the coherence length of the light viewed by any single detector.

Figure 9:
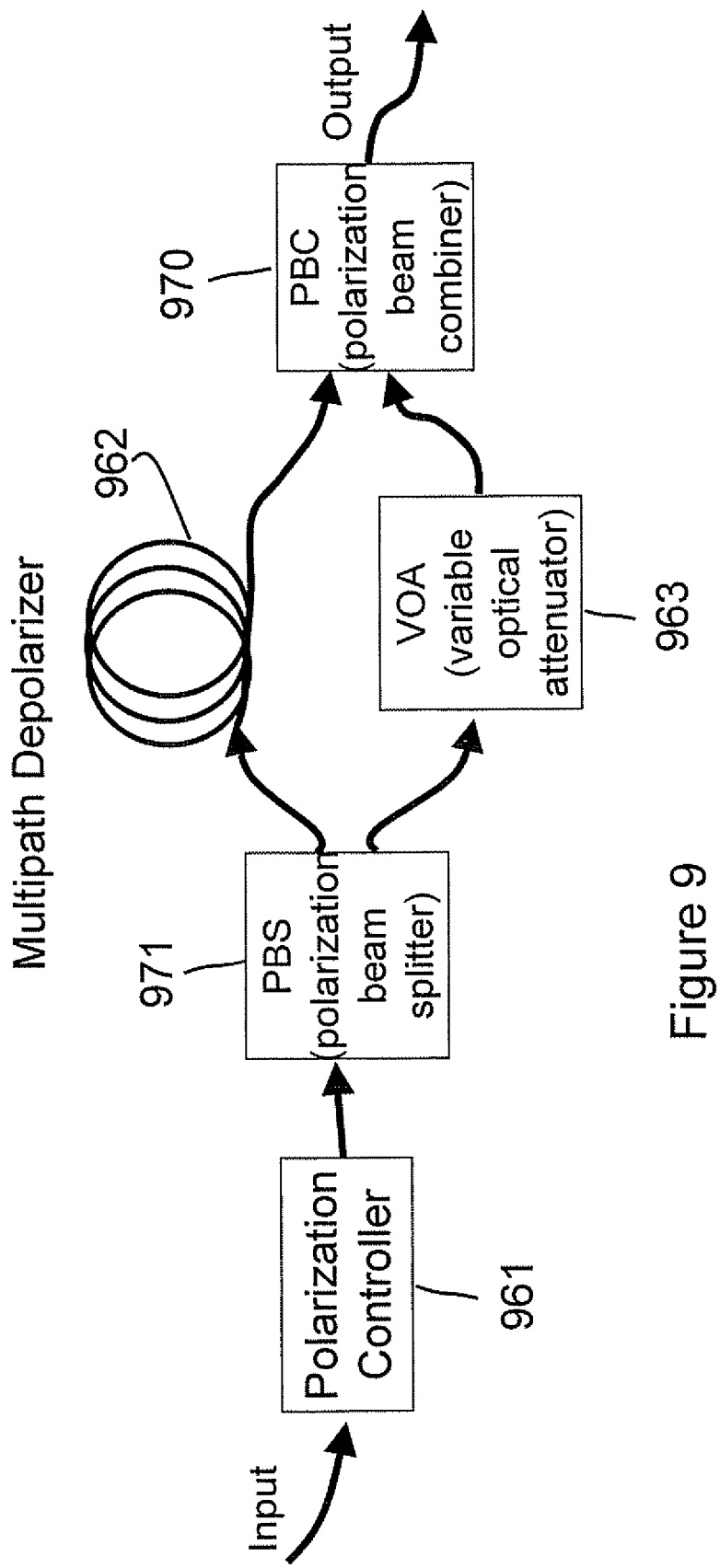
FIG. 9 is a schematic block diagram of a multipath optical depolarizer according to some embodiments of the present invention using a polarization beam splitter, variable optical attenuator, and polarization beam combiner.

Another modification of the depolarizer architecture shown in FIG. 7 is illustrated in FIG. 9. As illustrated in FIG. 9, both power couplers have been replaced, the first by a polarization beam splitter (PBS) 971 and the second by a polarization beam combiner (PBC) 970. A single polarization controller 961 is placed between the input and the PBS 971. This polarization controller 961 rotates the predominately linear polarization of the input source so that the power is split nearly 50%/50% by the PBS 971. The fiber loop 962 in the top leg provides a path length difference that may be selected to reduce or even destroy the coherence between the two paths. The VOA 963 in the bottom leg provides fine power control. The PBC 970 recombines the two orthogonal polarizations back onto one output fiber. The VOA 963 may not be included in some embodiments depending on the degree of depolarization desired and the performance of the other optical components in the depolarizer. This architecture should have even further reduced insertion loss, as both the PBS 971 and the PBC 970 should have lower insertion loss than the power couplers 760 (FIG. 7).

Figure 10:
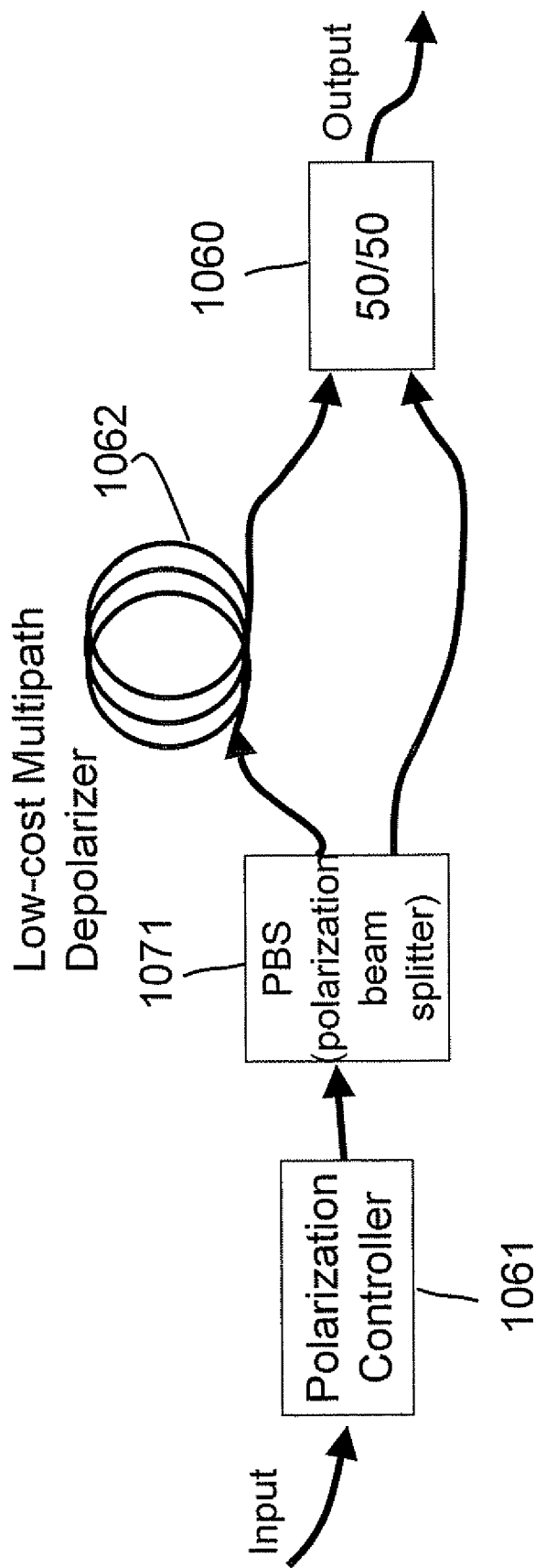
FIG. 10 is a schematic block diagram of a multipath optical depolarizer according to some embodiments of the present invention using a polarization controller, polarization beam splitter, and a fixed coupler.

A potentially lower cost version of a depolarizer is illustrated in FIG. 10. This architecture uses a single polarization controller 1061 and a PBS 1071. The polarization controller 1061 is used to rotate the linear polarization so that it is split nearly 50%/50% by the PBS 1071. The fiber loop 1062 provides a path length difference that may reduce or even destroy the coherence between the two paths. The light is recombined using a 50%/50% coupler 1060. The architecture of the embodiments of FIG. 10 may use fewer and cheaper parts than that of FIG. 9, but may not have the same degree of depolarization as the depolarizers described with reference to FIGS. 6 through 9.

Figure 11:
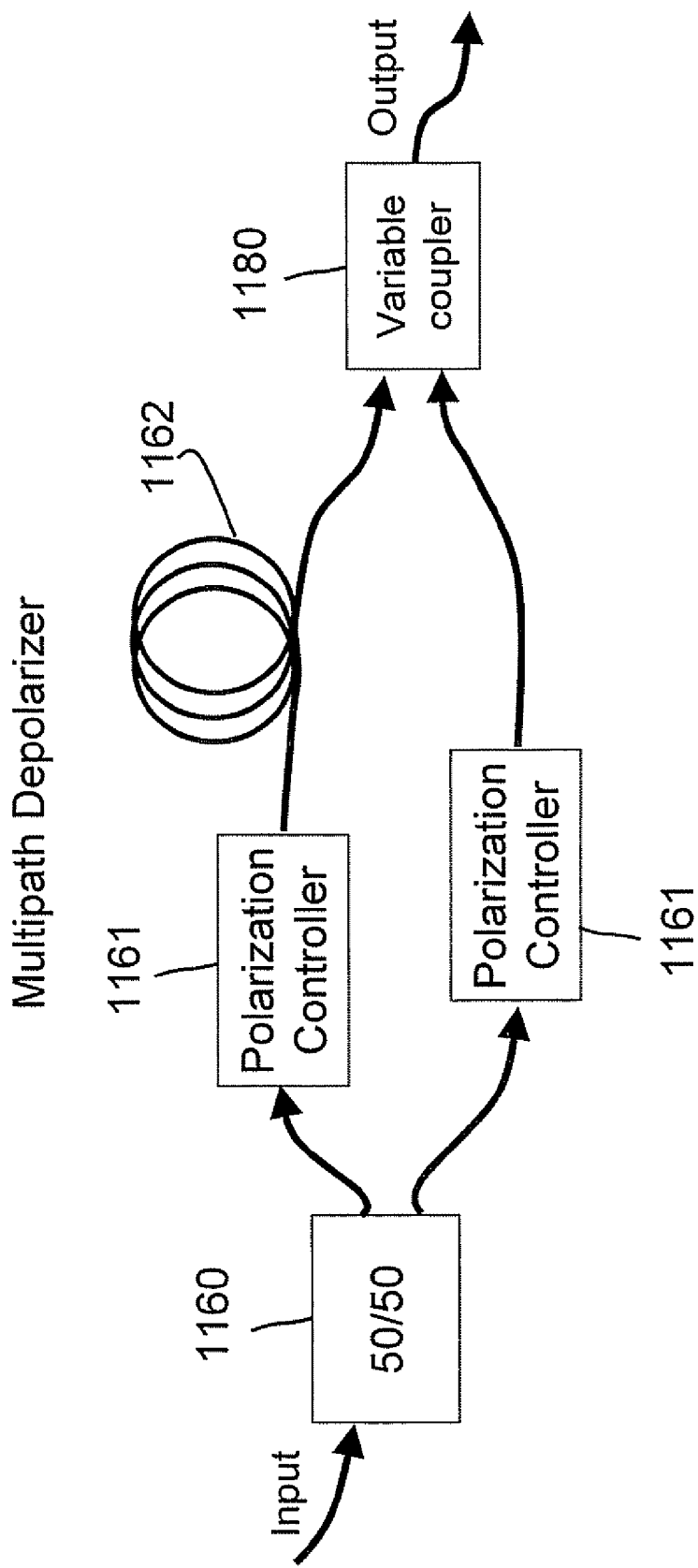
FIG. 11 is a schematic block diagram of a multipath optical depolarizer according to some embodiments of the present invention using a polarization control, and a variable coupler.

A depolarizer design according to further embodiments of the present invention is illustrated in FIG. 11. The optical input power is split by a 50%/50% power coupler 1160. One leg is connected to a polarization controller 1161, then to a length of fiber/coil 1162 and finally to a variable coupler 1180. The other leg is connected to a second polarization controller 1161 and then to the other leg of the variable coupler 1180. The polarization controllers 1161 may be set so that the light passing through each leg is rotated 90 degrees with respect to the light in the other leg. The fiber coil 1162 in the first leg may be longer than the coherence length observed by any individual detector in the system and may ensure that the light coming from each of the two legs is incoherent with respect to the other leg. The variable coupler 1180 may be used to match the amount of power coming from each leg. Note that it is possible to build this configuration in some embodiments of the present invention with just one polarization controller. The configuration of the embodiments of FIG. 11 may produce highly unpolarized light (low DOP).

Figure 12:
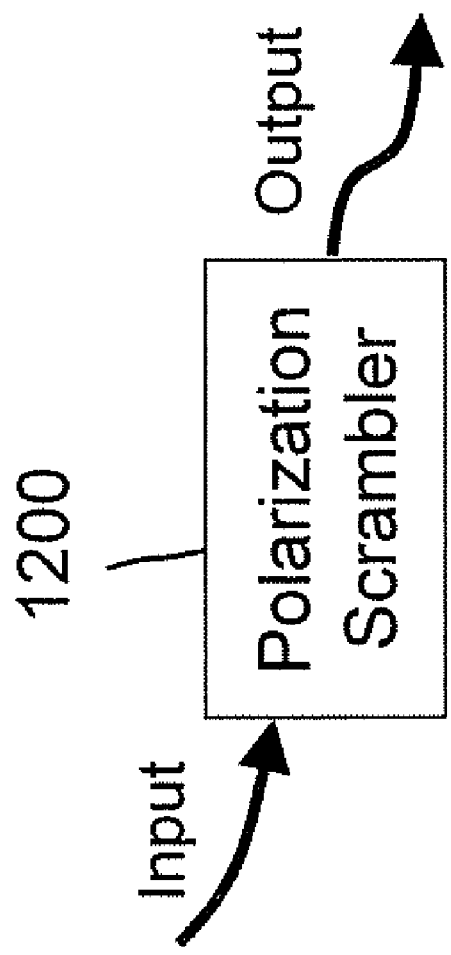
FIG. 12 is a schematic block diagram of an optical depolarizer according to some embodiments of the present invention using a polarization scrambler.

Another type of depolarizer is shown in FIG. 12, the depolarization is accomplished by using a polarization scrambler 1200 to vary the polarization over time. Provided that the time to cycle through the various polarization states is on the order of or less than the integration time of an photodiode in the system, then the light may appear depolarized to the photodiode. There are numerous implementations for polarization scramblers including, for example, ones with motorized moving waveplates, ones that squeeze the fiber to change the polarization properties, and ones that have integrated electrooptic devices that change the polarization properties of the device.

It will be understood that a variety of designs of the depolarizer may be utilized in various embodiments of the present invention and, therefore, depolarizers are not limited to the embodiments discussed herein. For example, in some embodiments the depolarizer is designed to provide unpolarized light to each detector.

Some embodiments of the present invention will now be discussed with respect to FIGS. 13A through 26. As used herein, the term "depolarized light" refers generally to substantially unpolarized (depolarized) light. The use of the word substantially indicates that the light may not be completely depolarized, i.e. some portion/percentage of the light may still be polarized without departing from the scope of the present invention. In other words, the degree of depolarization may vary from one embodiment to another. The term "depolarizer" refers to a device that creates substantially unpolarized light from substantially polarized light. The term "unpolarized light source" refers to a light source that provides substantially unpolarized light, i.e. the unpolarized light may vary in degree. In some embodiments of the present invention, the light may be from zero to about 30 percent polarized and still be considered "unpolarized" light in accordance with some embodiments of the present invention.

As further used herein, the term "birefringence" refers to an optical path length difference between polarization states. A birefringence controller according to some embodiments of the present invention may be configured to modify a polarization-dependent optical path length as will be discussed in detail below.

Figure 13A:
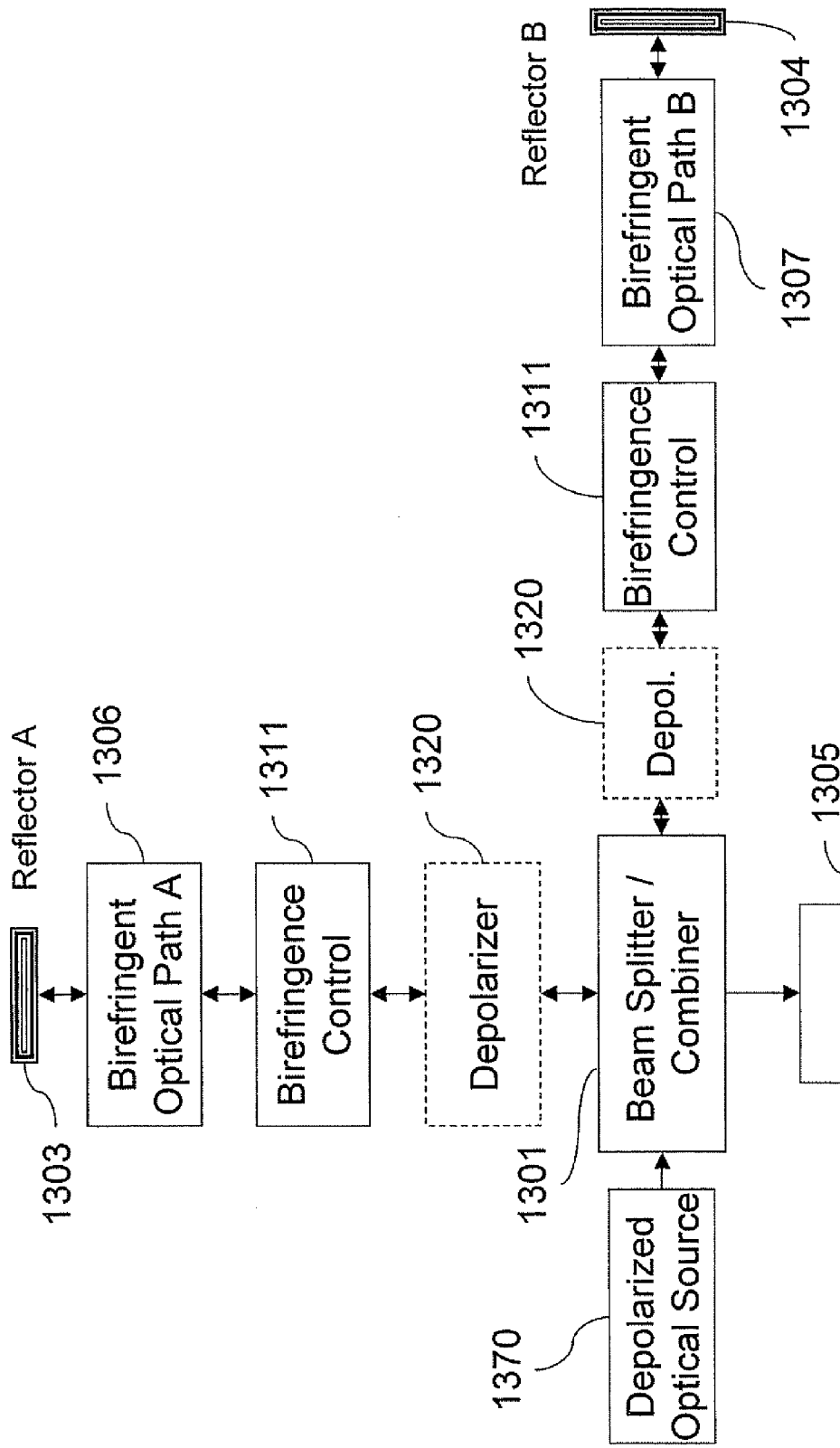
FIG. 13A is a schematic block diagram illustrating a Michelson interferometer having birefringent optical paths, using a depolarized source and birefringence control according to some embodiments of the present invention.

A general interferometer according to some embodiments of the present invention will now be described with reference to FIGS. 13A and 13B. Referring first to FIG. 13A, the interferometer consists of an unpolarized or depolarized source 1370, a beam splitter/combiner 1301, and birefringent paths A 1306 and B 1307. Because the light is depolarized, SOP control discussed with respect to conventional embodiments is neither required nor useful. Instead, birefringence control 1311 is used in one or both of paths A 1306 and B 1307. Birefringence control may be preferable to SOP control, because only one degree of freedom is required as discussed above. A depolarizer 1320 may be deployed in one or both the birefringent paths A 1306 and B 1307. The depolarizer 1320 in this circumstance may serve to compensate for an increased polarization that may have been induced by polarization dependent loss (or gain) in the system.

Figure 13B:
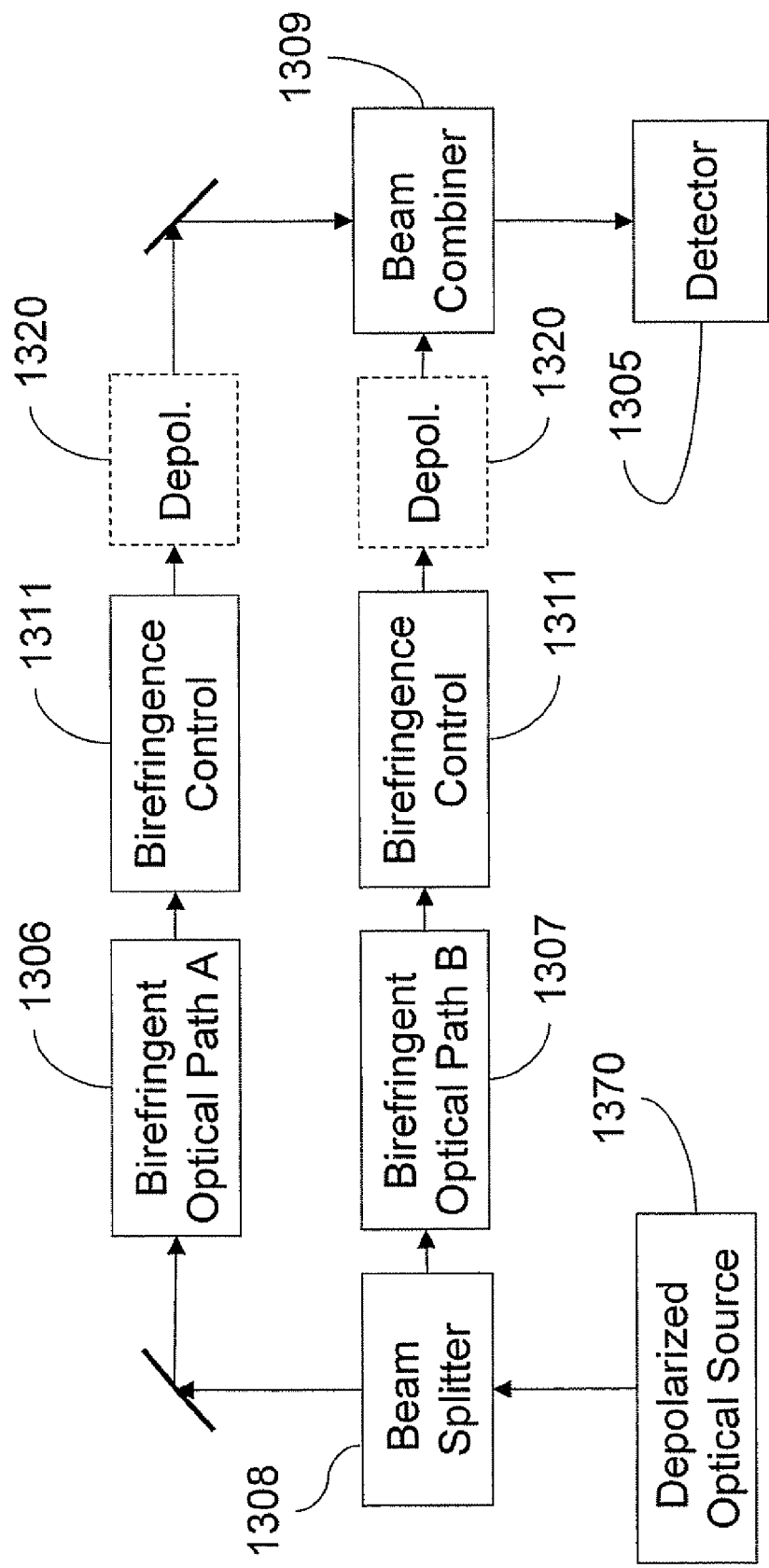
FIG. 13B is a schematic block diagram illustrating a Mach-Zehnder interferometer having birefringent optical paths, using a depolarized source and birefringence control according to some embodiments of the present invention.

Referring now to FIG. 13B, the interferometer consists of an unpolarized or depolarized source 1370, a beam splitter/combiner 1301, and birefringent paths A 1306 and B 1307. Because the light is depolarized, SOP control is neither required nor useful. Instead, birefringence control 1311 is used in one or both of paths A 1306 and B 1307 as discussed with respect to FIG. 13A.

Embodiments of the present invention illustrated in FIGS. 13A and 13B illustrate a Michelson configuration and a Mach-Zehnder configuration, respectively, including elements according to some embodiments of the present invention. Each configuration uses an unpolarized or depolarized source 1370, contains a birefringent optical path A 1306 that may be termed a reference path and a birefringent path B 1307 that may be termed a sample path. Birefringence control 1311 may be used in one or both birefringent paths to compensate for differential birefringence between the paths. Supplemental depolarization 1320 may be used in one or more paths to at least partially compensate for polarizing elements in the respective path.

In the Michelson configuration of FIG. 13A, light from the source arm is split by a power coupler 1301 and sent to the reference arm 1306 and the sample arm 1307. Reflected light from the reference reflector 1303 and sample detector 1304 is combined by the power coupler 1301 and at least some of the combined power appears at the detector 1305. The detector 1305 may include a single or multiple elements, and may include a wavelength-dispersed spectrometer.

In the Mach-Zehnder configuration of FIG. 13B, light from the source arm is split by a power splitter 1308 and sent to the reference arm 1306 and the sample arm 1307. Light from the reference and sample arms are combined by the power coupler 1309 and at least some of the combined power appears at the detector 1305. The detector 1305 may include a single or multiple elements, and may include a wavelength-dispersed spectrometer.

Figure 14A:
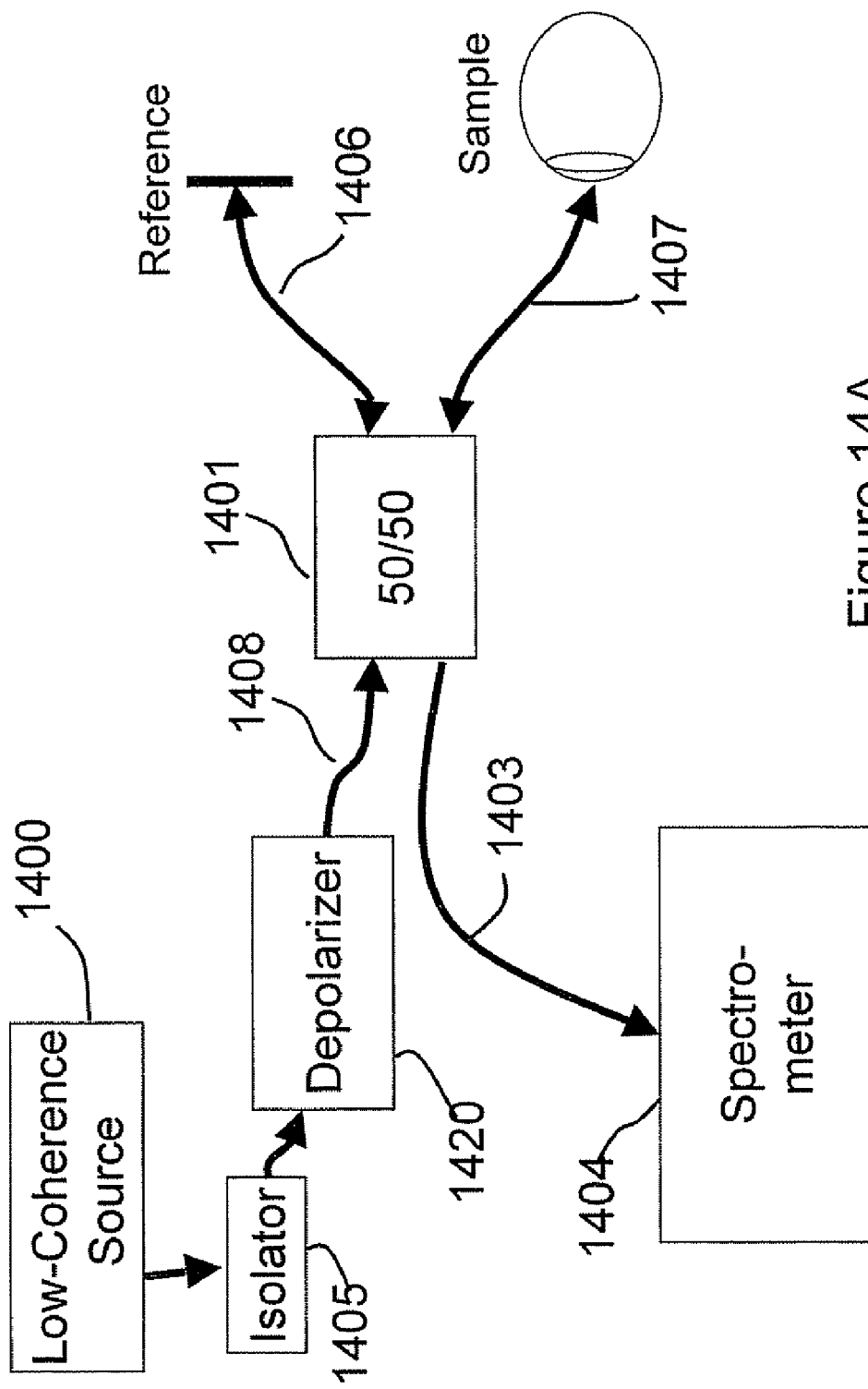
FIG. 14A is a schematic block diagram illustrating a Fourier-domain optical coherence tomography system according to some embodiments of the present invention using a low coherence source with a depolarizer.
Figure 14B:
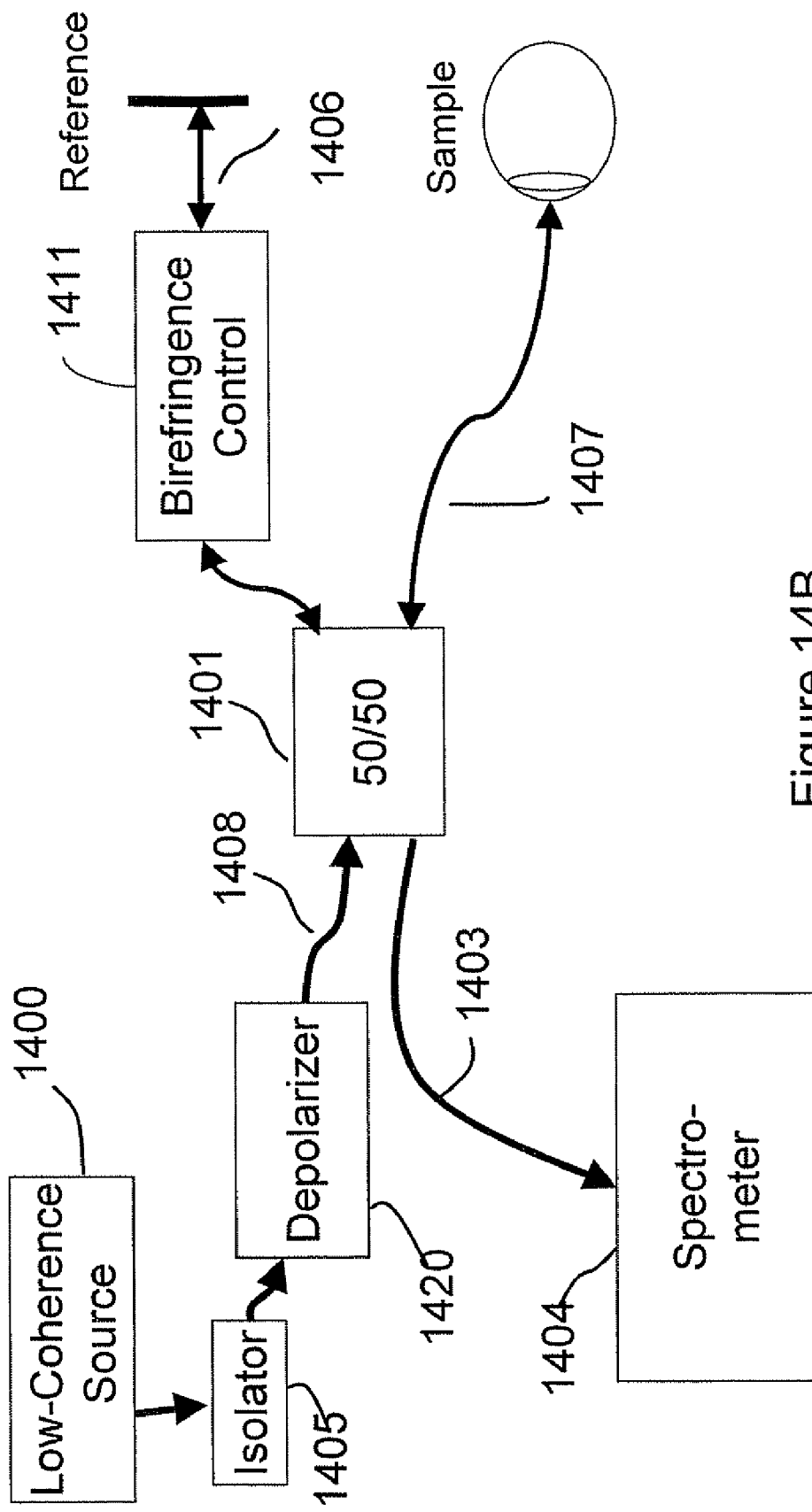
FIG. 14B is a schematic block diagram illustrating a Fourier-domain optical coherence tomography system according to some embodiments of the present invention using a low coherence source with a depolarizer and birefringence control.

Referring now to FIG. 14A, an optical imaging system according to some embodiments of the present invention will now be discussed. As illustrated in FIG. 14A, a depolarizer is used in a spectral-domain optical coherence tomography SD-OCT architecture. The depolarizer 1420 in the source arm 1408 depolarizes the light from the low-coherence or broadband source 1400 after it has passed through an isolator 1405. Light from the source arm is split by a power coupler 1401 and sent to the reference arm 1406 and the sample arm 1407. Reflected light from the reference and sample arms are combined by the power coupler 1401 and sent down both the source arm 1408 and the detector arm 1403. The isolator 1405 may limit or possibly prevent light from reentering the source 1400. In some embodiments of the present invention, a source that is insensitive to reflected light may be used and the isolator may be omitted.

Light in the detector arm 1403 enters the spectrometer 1404 where it is dispersed and falls upon a detector array. Each detector in the detector array measures the total power in some frequency band that is a subset of the total spectrum of the source 1400. In embodiments of the present invention illustrated in FIG. 14A, the depolarizer may be configured to depolarize over the bandwidth viewed by any single detector not just on average over the entire spectrum of the source.

Referring now to FIG. 1413, an optical imaging system according to some embodiments of the present invention will be discussed. As illustrated therein, a depolarizer is used in a birefringent spectral-domain optical coherence tomography SD-OCT architecture. The depolarizer 1420 in the source arm 1408 depolarizes the light from the low-coherence or broadband source 1400 after it has passed through an isolator 1405. Light from the source arm is split by a power coupler 1401 and sent to the reference arm 1406 and the sample arm 1407. Birefringence control 1411 may be applied to either the reference path 1406 or the sample path 1407 or both without departing from the scope of the present invention. Reflected light from the reference and sample arms are combined by the power coupler 1401 and sent down both the source arm 1408 and the detector arm 1403. The isolator 1405 may limit or possibly prevent light from reentering the source 1400. In some embodiments of the present invention, a source that is insensitive to reflected light may be used and the isolator may be omitted.

Figure 14C:
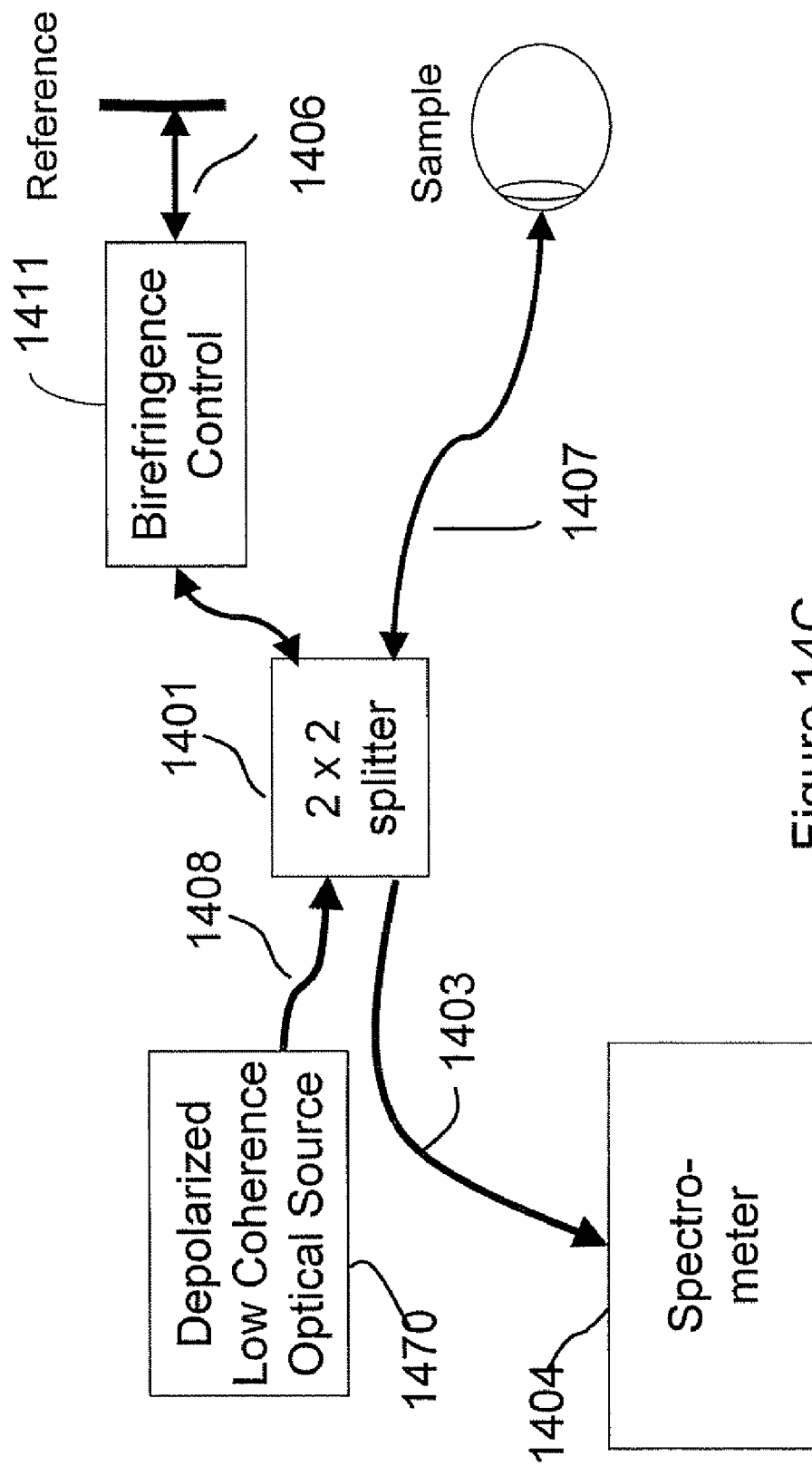
FIG. 14C is a schematic block diagram illustrating a Fourier-domain optical coherence tomography system according to some embodiments of the present invention using a depolarized low coherence source and birefringence control.

Referring now to FIG. 14C, an optical imaging system according to some embodiments of the present invention will be discussed. As illustrated in FIG. 14C, an unpolarized or depolarized source may be used in a birefringent spectral-domain optical coherence tomography SD-OCT architecture. Light from the source arm is split by a power coupler 1401 and sent to the reference arm 1406 and the sample arm 1407. Birefringence control 1411 is applied to either path in order balance the birefringence in each path. Reflected light from the reference and sample arms are combined by the power coupler 1401 and sent down both the source arm 108 and the detector arm 1403.

In some embodiments of the present invention, the birefringence control may be set during assembly of the instrument and may need only be adjusted occasionally or not at all during operation.

In further embodiments of the present invention, the birefringence control may be dynamically set based on a metric of the measured or image signal, the rate of active control being set by the demands of the individual application, but in general the rate of active control is substantially slower than the detector integration bandwidth.

Figure 15A:
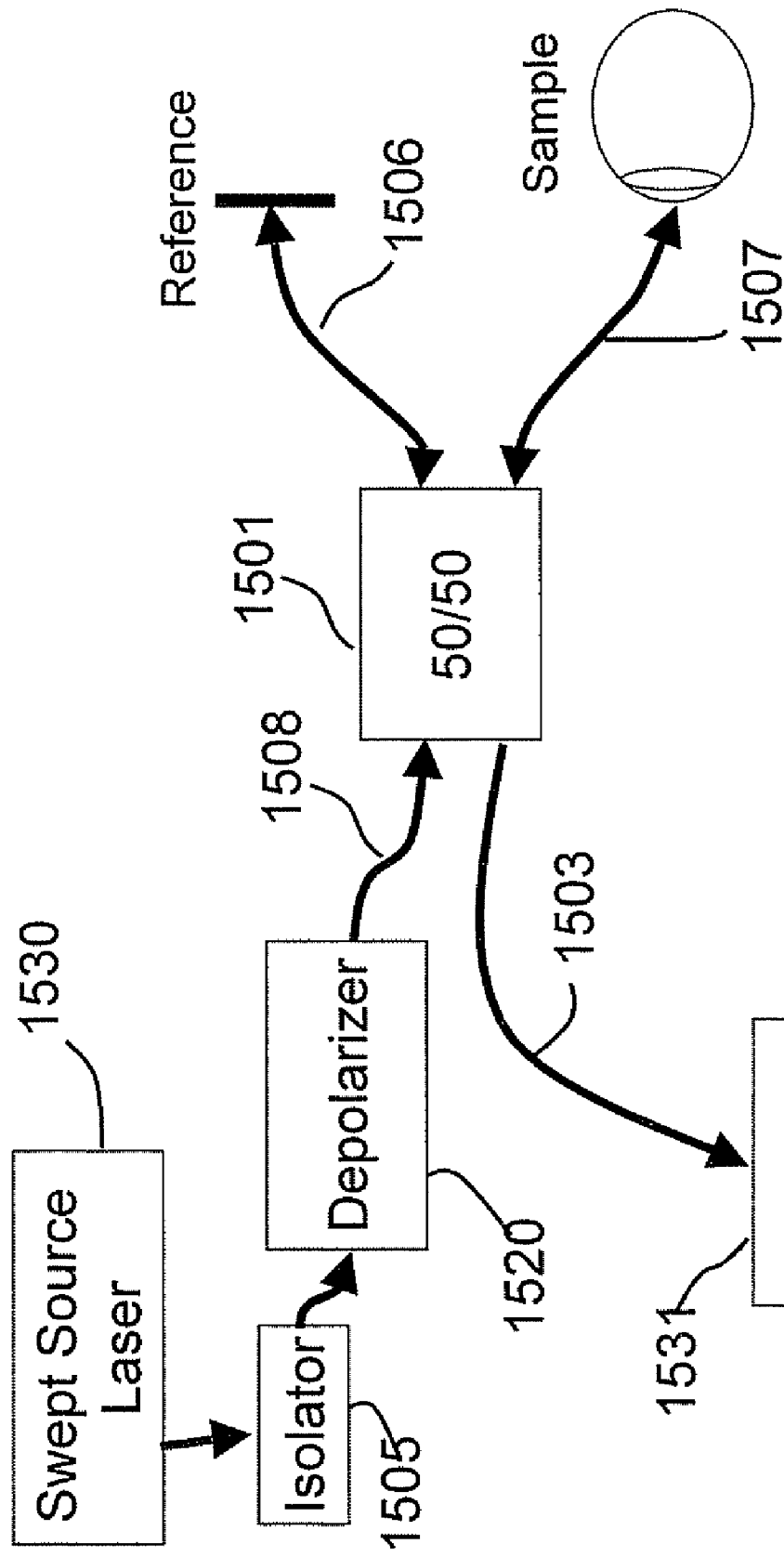
FIG. 15A is a schematic block diagram illustrating a Fourier-domain optical coherence tomography system according to some embodiments of the present invention using a swept source with a depolarizer.

Further embodiments of the present invention will now be discussed with respect to FIGS. 15A through 15C. As illustrated in FIG. 15A, a depolarizer is used in a swept-source optical coherence tomography SS-OCT architecture. The depolarizer 1520 in the source arm 1508 depolarizes the light from the swept-source laser 1530 after it has passed through an isolator 1505. Light from the source arm 1508 is split by a power coupler 1501 and sent to the reference arm 1506 and the sample arm 1507. Reflected light from the reference and sample arms are combined by the power coupler 1501 and sent down both the source arm 1508 and the detector arm 103. The isolator 1505 may limit or even prevent light from reentering the source 130. In some embodiments of the present invention, a source that is insensitive to reflected light may be used and the isolator may be omitted.

Figure 15B:
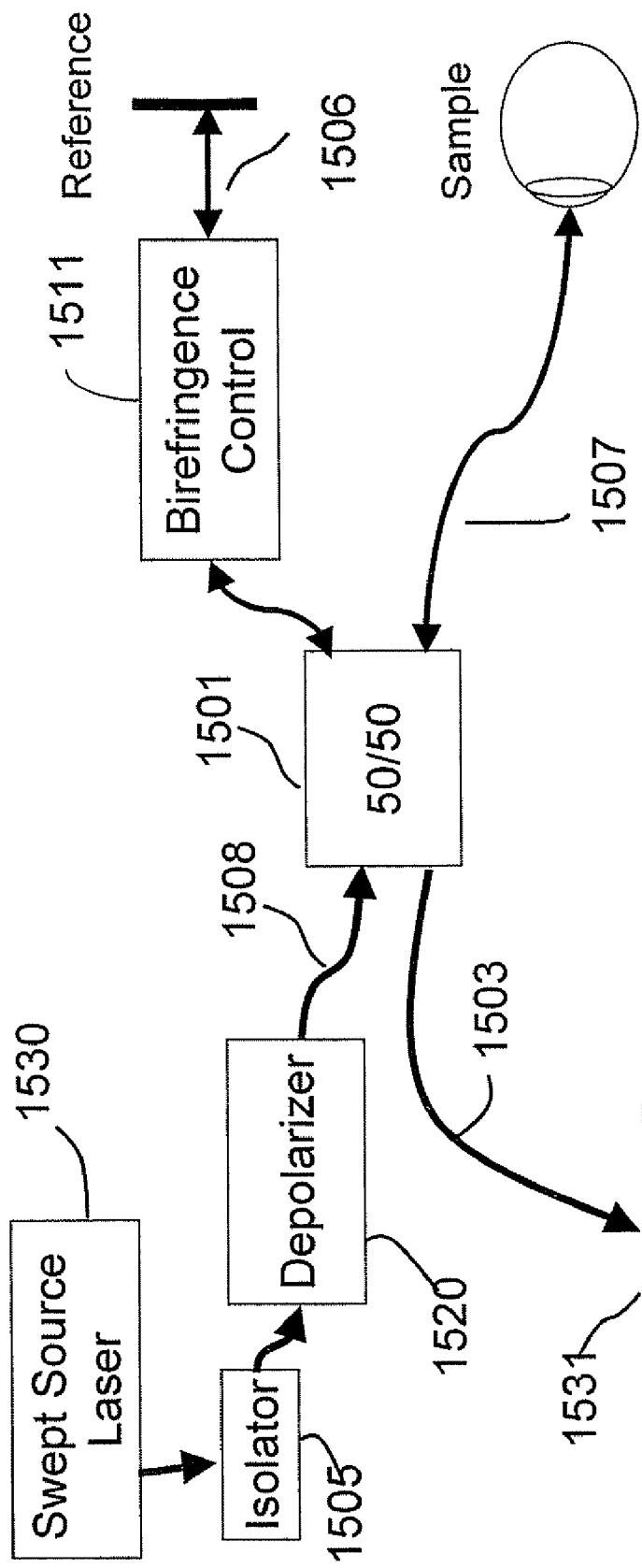
FIG. 15B is a schematic block diagram illustrating a Fourier-domain optical coherence tomography system according to some embodiments of the present invention using a swept source with a depolarizer and birefringence control.

Referring now to FIG. 15B, an optical imaging system according to some embodiments of the present invention will be discussed. As illustrated in FIG. 16B, a depolarizer may be used in a birefringent swept-source optical coherence tomography SS-OCT architecture. The depolarizer 1520 in the source arm 1508 depolarizes the light from the swept source laser 1500 after it has passed through an isolator 1505. A swept source laser can be generally referred to as a narrowband light source having an optical frequency that may vary with time. Thus, other equivalent light sources may also be used. Light from the source arm is split by a power coupler 1501 and sent to the reference arm 1506 and the sample arm 1507. Birefringence control 1511 may be applied to either path in order balance the birefringence in each path. Reflected light from the reference and sample arms are combined by the power coupler 1501 and sent down both the source arm 1508 and the detector arm 1503. The isolator 1505 may limit or possibly prevent light from reentering the source 1500. In some embodiments of the present invention, a source that is insensitive to reflected light may be used and the isolator may be omitted.

Figure 15C:
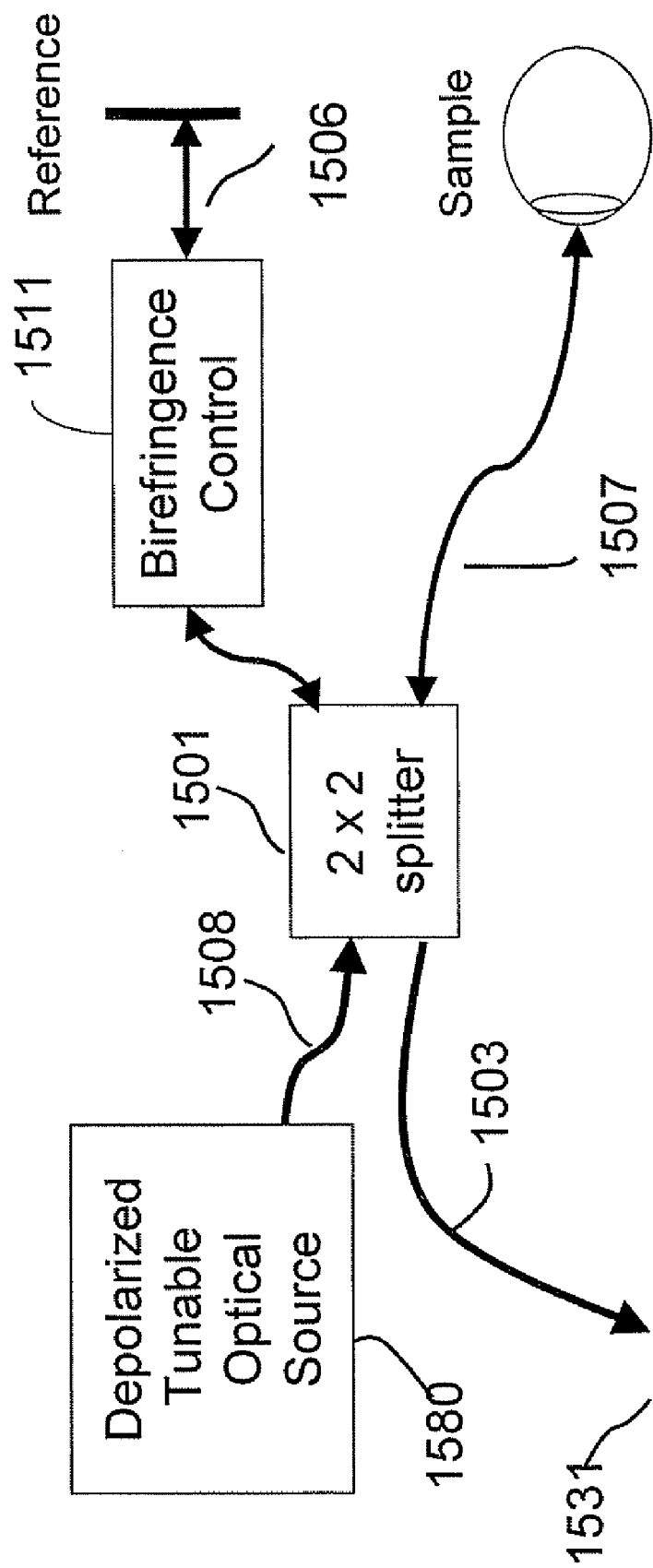
FIG. 15C is a schematic block diagram illustrating a Fourier-domain optical coherence tomography system according to some embodiments of the present invention using a depolarized swept source and birefringence control.

Referring now to FIG. 15C, an optical imaging system according to some embodiments of the present invention will be discussed. As illustrated in FIG. 15C, an unpolarized or depolarized source may be used in a birefringent swept-source optical coherence tomography SS-OCT architecture. Light from the source arm is split by a power coupler 1501 and sent to the reference arm 1506 and the sample arm 1507. Birefringence control 1511 may be applied to either path in order balance the birefringence in each path. Reflected light from the reference and sample arms are combined by the power coupler 1501 and sent down both the source arm 1508 and the detector arm 1503.

Light on the detector arm 1502 is incident on the single photodiode 1531. The photodiode 1531 acts as a detector that measures the total incident power over a given time interval. For the embodiments illustrated in FIG. 15C, the depolarizer depolarizes over the instantaneous line width of the swept laser source 1530, rather than just depolarizing the light on average over the entire spectrum of the swept source.

In some embodiments of the present invention, the birefringence control may be set during assembly of the instrument as discussed above. In further embodiments of the present invention, the birefringence control may be dynamic as discussed above.

Figure 16A:
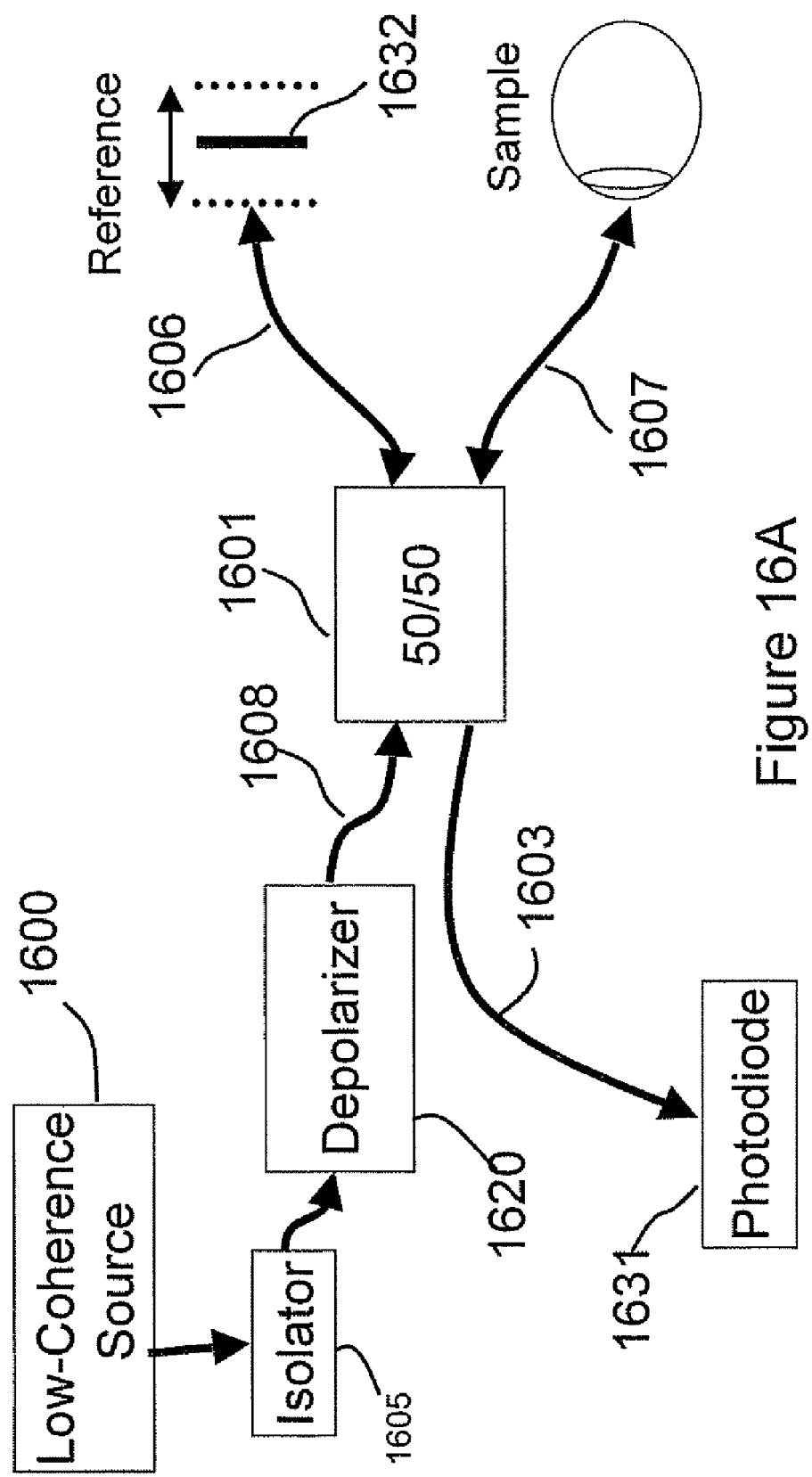
FIG. 16A is a schematic block diagram illustrating a time-domain optical coherence tomography system according to some embodiments of the present invention using a low coherence source with a depolarizer.
Figure 16B:
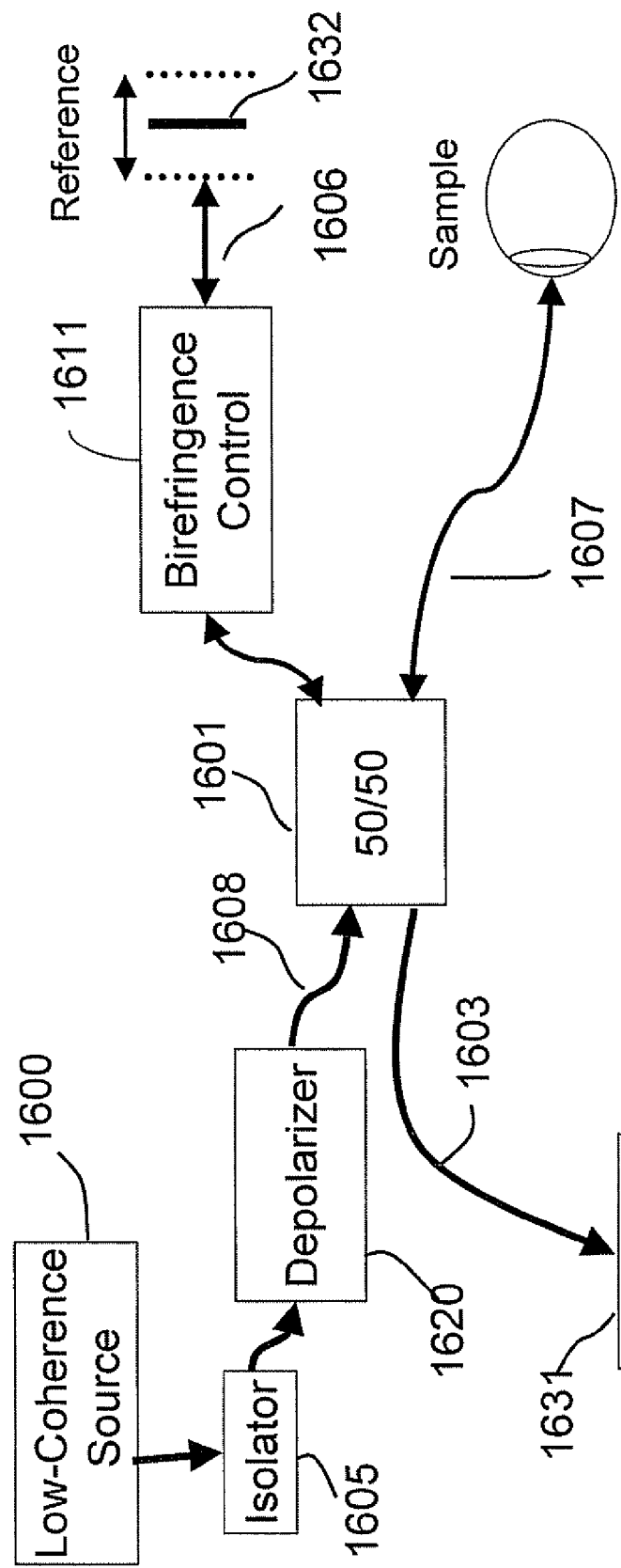
FIG. 16B is a schematic block diagram illustrating a time-domain optical coherence tomography system according to some embodiments of the present invention using a low coherence source with a depolarizer and birefringence control.

Referring now to FIG. 16A, a depolarizer used in a time-domain optical coherence tomography TD-OCT architecture will be discussed. The depolarizer 1620 in the source arm 1608 depolarizes the light from the low-coherence or broadband source 1600 after it has passed through an isolator 1605. Light from the source arm is split by a power coupler 1601 and sent to the reference arm 1606 and the sample arm 1607. In these embodiments, the length of the reference arm may be changed over time, here illustrated by a moving mirror 1632. Reflected light from the reference and sample arms are combined by the power coupler 1601 and sent down both the source arm 1608 and the detector arm 1603. The isolator 1605 may limit or possibly prevent light from reentering the source 1600. In some embodiments of the present invention, the source 1600 is insensitive to reflected light and the isolator 1605 may be omitted.

Referring now to FIG. 16B, an optical imaging system according to some embodiments of the present invention will be discussed. As illustrated therein, a depolarizer may be used in a birefringent time-domain optical coherence tomography TD-OCT architecture. The depolarizer 1620 in the source arm 1608 depolarizes the light from the low coherence source 1600 after it has passed through an isolator 1605. Light from the source arm is split by a power coupler 1601 and sent to the reference arm 1606 and the sample arm 1607. Birefringence control 1611 is to applied to either path in order balance the birefringence in each path. Reflected light from the reference and sample arms are combined by the power coupler 1601 and sent down both the source arm 1608 and the detector arm 1603. The isolator 1605 may limit or possibly prevent light from reentering the source 1600. In some embodiments of the present invention, a source that is insensitive to reflected light may be used and the isolator may be omitted.

Light on the detector arm 1603 is incident on the single photodiode detector 1631. The detector 1631 measures the total power over a given time interval. The depolarizer 1620 depolarizes over the total bandwidth of the low-coherence or broadband source 1600.

Figure 16C:
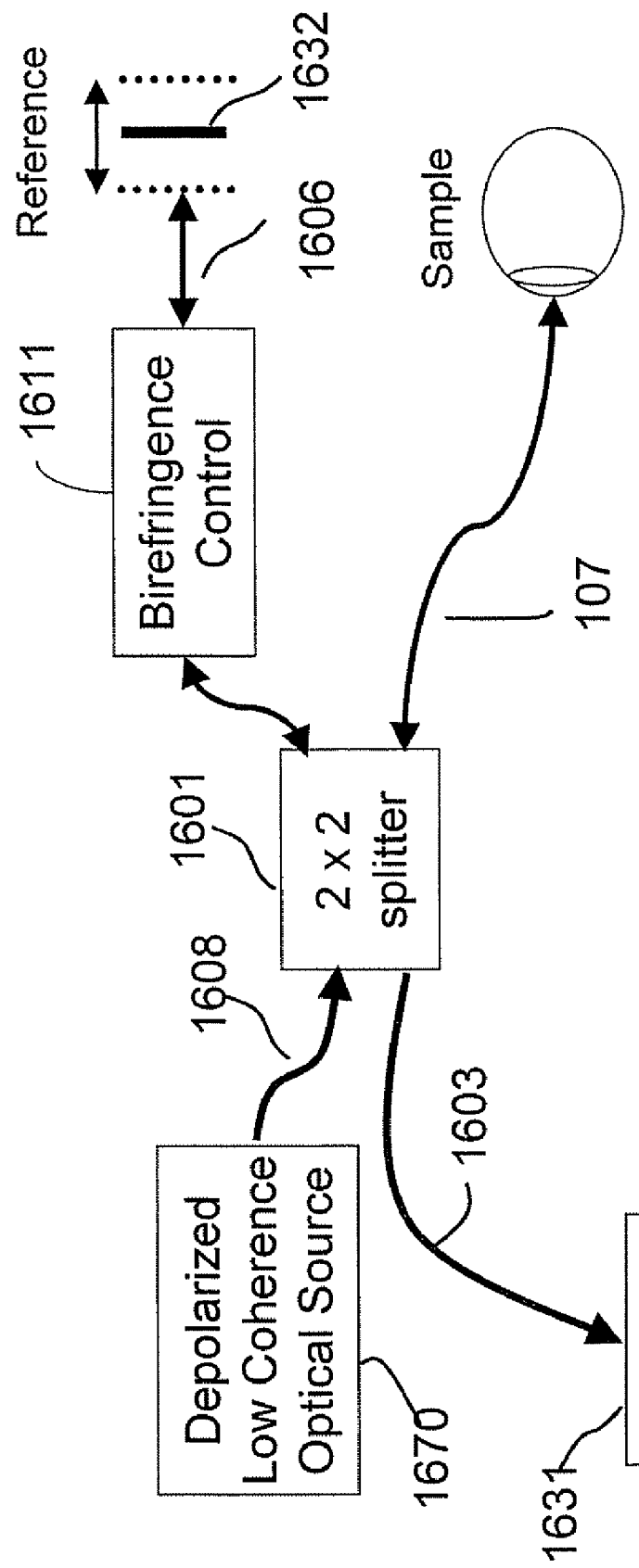
FIG. 16C is a schematic block diagram illustrating a time-domain optical coherence tomography system according to some embodiments of the present invention using a depolarized low coherence source and birefringence control.

Referring now to FIG. 16C, an optical imaging system according to some embodiments of the present invention will now be discussed. As illustrated in FIG. 16C, an unpolarized or depolarized source may be used in a birefringent time-domain optical coherence tomography TD-OCT architecture. Light from the source arm is split by a power coupler 1601 and sent to the reference arm 1606 and the sample arm 1607. Birefringence control 1611 is to applied to either path in order balance the birefringence in each path. Reflected light from the reference and sample arms are combined by the power coupler 1601 and sent down both the source arm 1608 and the detector arm 1603.

Light on the detector arm 1603 is incident on the single photodiode detector 1631. The detector 1631 measures the total power over a given time interval.

Figure 17A:
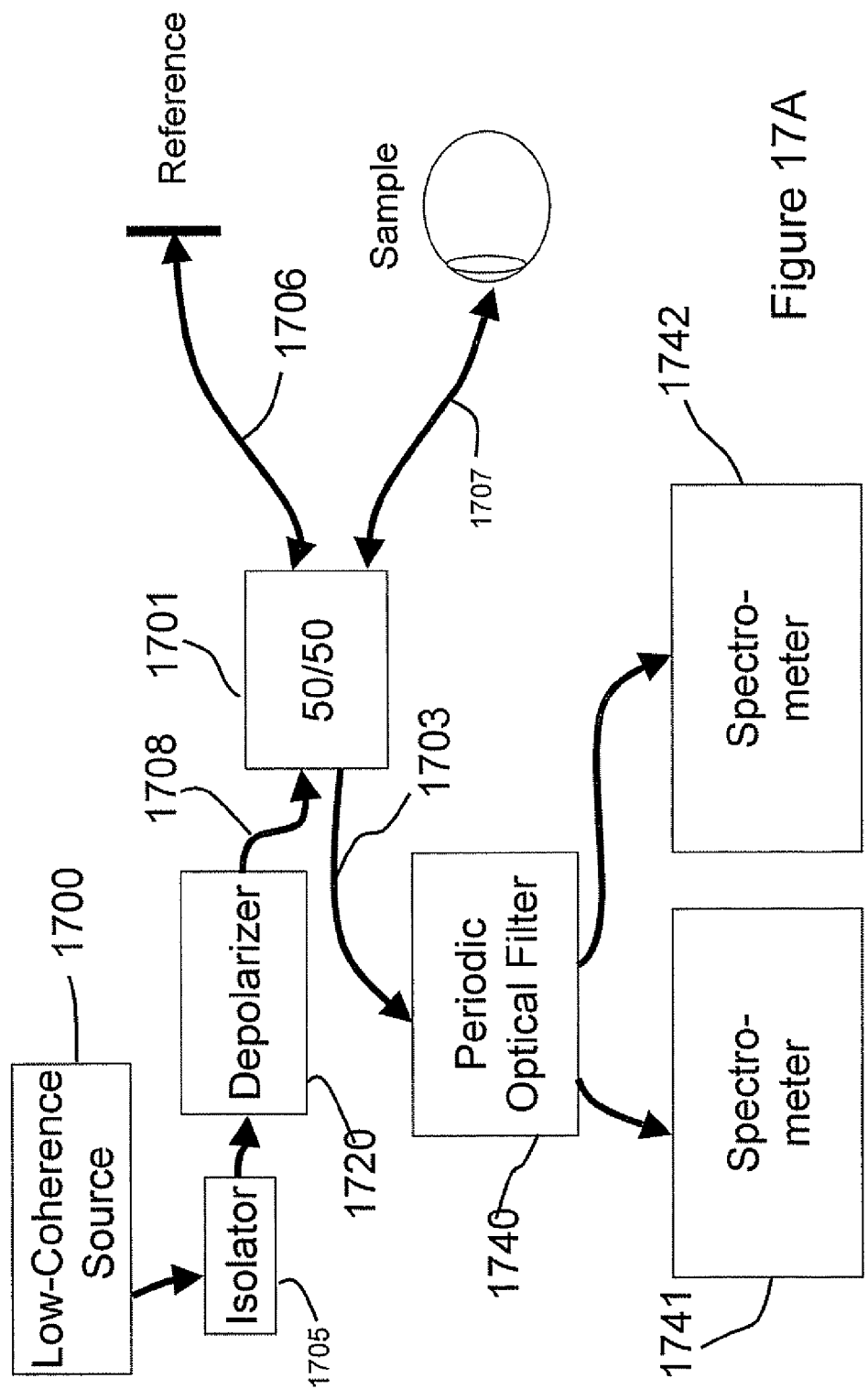
FIG. 17A is a schematic block diagram illustrating a Fourier-domain optical coherence tomography system according to some embodiments of the present invention using a depolarized source and periodic filters.

Referring now to FIG. 17A, a periodic optical filter (POF) 1740 added to the configuration illustrated in FIG. 14A will be discussed. The addition of the POF 1740 may provide additional benefits as discussed in U.S. patent application Ser. No. 11/495,226, filed Jul. 28, 2006, entitled "OPTICAL COHERENCE IMAGING SYSTEMS HAVING A REDUCED EFFECTIVE LINEWIDTH AND METHODS OF USING THE SAME," the content of which is hereby incorporated by reference as if set forth in its entirety. As discussed therein, the POF 1740 could be an interleaver and/or a Fabry Perot cavity and/or other POF and may be tunable by various means including mechanical, electrical, and/or optical. The added depolarizer in each of the described embodiments may be beneficially a depolarizer that works within the bandwidth viewed by any single detector in the system, including individual detectors inside one or more spectrometers.

Referring again to FIG. 17A, the depolarizer 1720 in the source arm 1708 depolarizes the light from the low-coherence or broadband source 1700 after it has passed through an isolator 1705. Light from the source arm is split by a power coupler 1701 and sent to the reference arm 1706 and the sample arm 1707. Reflected light from the reference and sample arms are combined by the power coupler 1701 and sent down both the source arm 1708 and the detector arm 1703. The isolator 1705 may limit or possibly prevent light from reentering the source. In some embodiments of the present invention, the source 1700 may be insensitive to reflected light and the isolator may be omitted. Light in the detector arm 1703 passes through a periodic optical filter 1740 and then passes either to spectrometer 1741 or spectrometer 1772. In each case, the light enters the spectrometer 1741, 1742 where it is dispersed and falls upon a detector array. Each detector in a detector array measures the total power in some band that is a subset of the total spectrum of the source. In embodiments of the present invention illustrated in FIG. 17A, the depolarizer depolarizes over the bandwidth viewed by any single detector rather than simply depolarizing on average over the entire spectrum of the source.

Figure 17B:
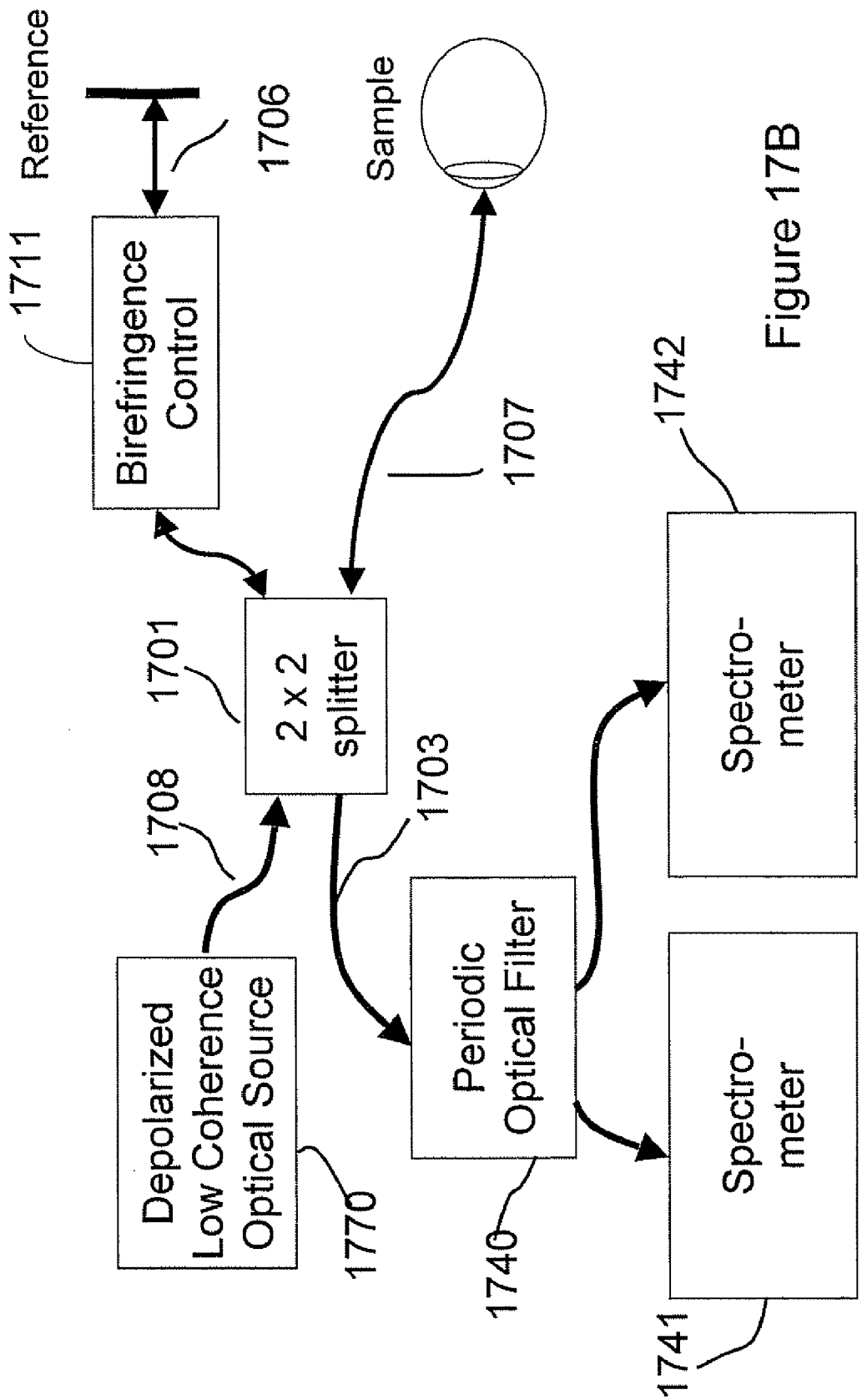
FIG. 17B is a schematic block diagram illustrating a Fourier-domain optical coherence tomography system according to some embodiments of the present invention using a depolarized source, birefringence control and periodic filters.

Referring now to FIG. 17B, embodiments of the present invention including birefringence control 1711 will be discussed. Birefringence control 1711 is added in order to modify birefringence in the reference and sample paths. The birefringence control may, as for other embodiments, be set once or only infrequently, or may be part of an active control system without departing from the scope of the present invention.

In some embodiments of the present invention, optical engines may include an optical source, a plurality of optical spectrometers, a plurality of interferometers and one or more optical depolarizers. One or more of the depolarizers may be a Lyot depolarizer and/or a multi-path depolarizer. In other embodiments of the present invention, optical engines may include a tunable optical source, a plurality of optical detectors, a plurality of interferometers and one or more optical depolarizers. One or more of the depolarizers may be a Lyot depolarizer and/or a multi-path depolarizer.

In further embodiments of the present invention, optical engines may include an optical source, a reference arm that changes effective optical path length, a plurality of optical detectors, a plurality of interferometers and one or more optical depolarizers. One or more of the depolarizers may be a Lyot depolarizer and/or a multi-path depolarizer and/or a polarization scrambler.

In further embodiments of the present invention, optical engines include an optical source, a plurality of optical detectors, a plurality of interferometers, a plurality of periodic optical filters, and one or more optical depolarizers. One or more of the depolarizers may be a Lyot depolarizer and/or a multi-path depolarizer and/or a polarization scrambler.

Figure 18A:
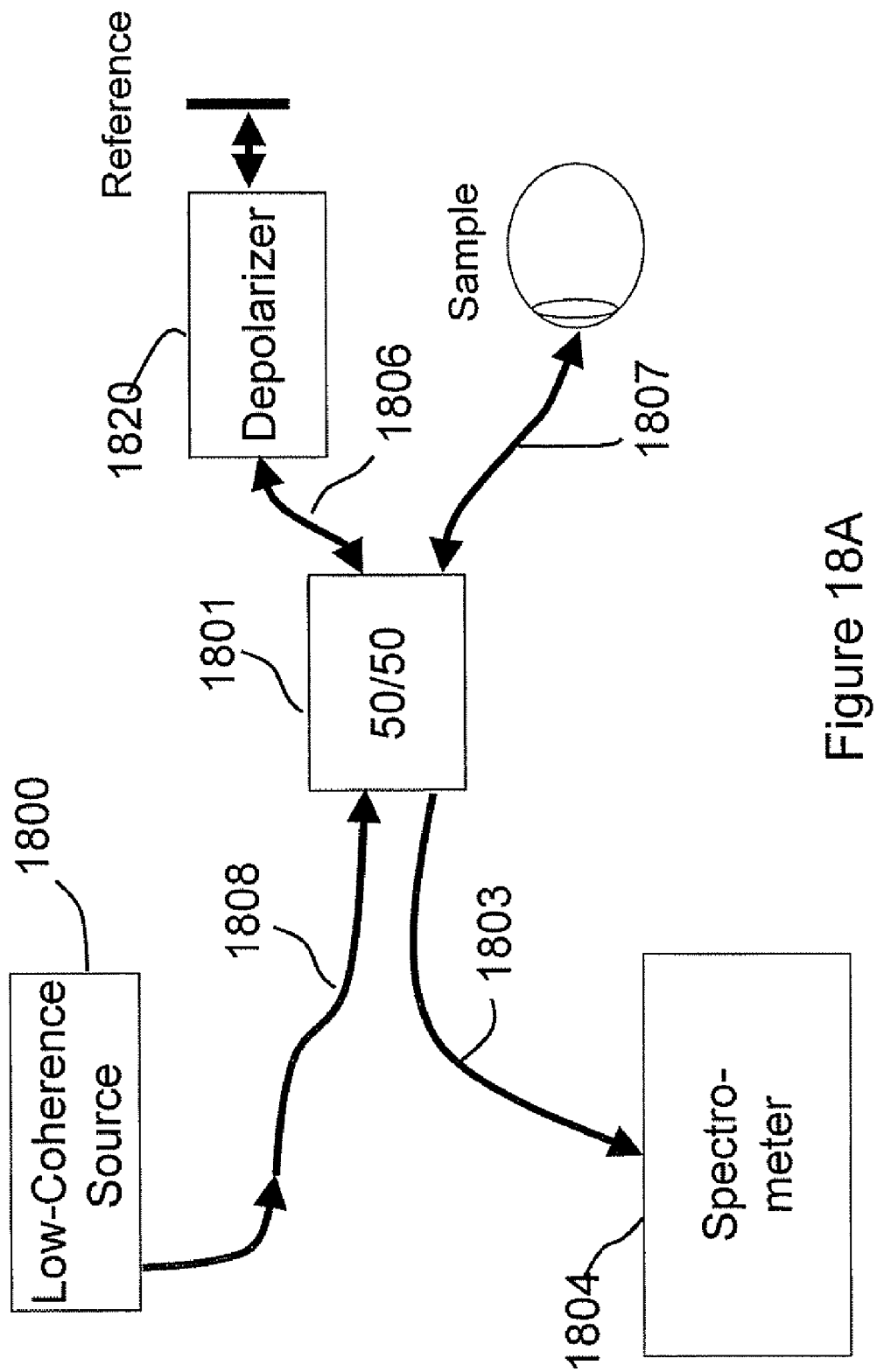
FIG. 18A is a schematic block diagram illustrating a Fourier-domain optical coherence tomography system according to some embodiments of the present invention using a low coherence source with a depolarizer in the reference arm.

Referring now to FIG. 18A, an optical engine according to some embodiments of the present invention will be discussed. As illustrated in FIG. 18A, a depolarizer 1820 is placed in the reference arm 1806 of the OCT engine. In this configuration only the light returning from the reference arm may be depolarized. When interfered with the light from the sample arm 1807, which is polarized or partially polarized, there will typically be an interference signal regardless of the specific polarization properties of the sample. Typically this architecture will result in a 3.0 dB decrease in OSNR relative to the maximum possible OSNR, but there will generally be minimal change in the signal strength regardless of the polarization properties of the sample or changes in the polarization properties of the system.

Typically, in order for this configuration to work, the path length through the depolarizer 1820 will need to be essentially constant as a function of wavelength. This is the case for depolarizers, such as the Lyot depolarizer illustrated in FIG. 6 and the depolarizer based on a polarization scrambler in FIG. 12.

Figure 18B:
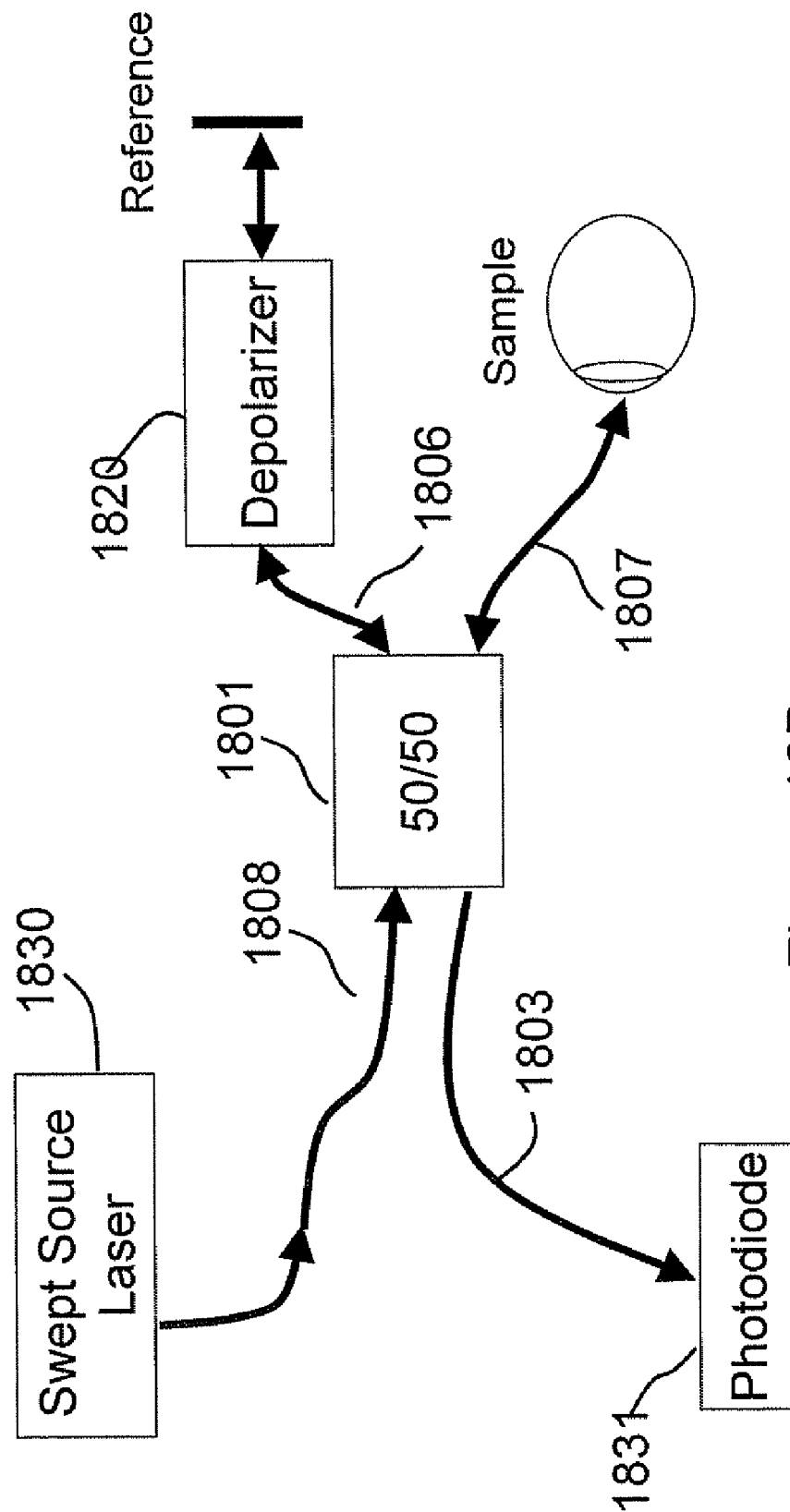
FIG. 18B is a schematic block diagram illustrating a Fourier-domain optical coherence tomography system according to some embodiments of the present invention using a swept source with a depolarizer in the reference arm.

Referring now to FIG. 18B, an optical engine according to further embodiments of the present invention will be discussed. As illustrated in FIG. 18B, a depolarizer 1820 is placed in the reference arm of an OCT engine based on a swept laser source 1830. In this configuration the light returning from the reference arm may be depolarized. When interfered with the light from the sample arm 1807, which is polarized or partially polarized, there will typically be an interference signal regardless of the specific polarization properties of the sample. Typically this architecture will result in a 3.0 dB decrease in OSNR relative to the maximum possible OSNR, but there generally will be minimal change in the signal strength regardless of the polarization properties of the sample or changes in the polarization properties of the system.

Figure 18C:
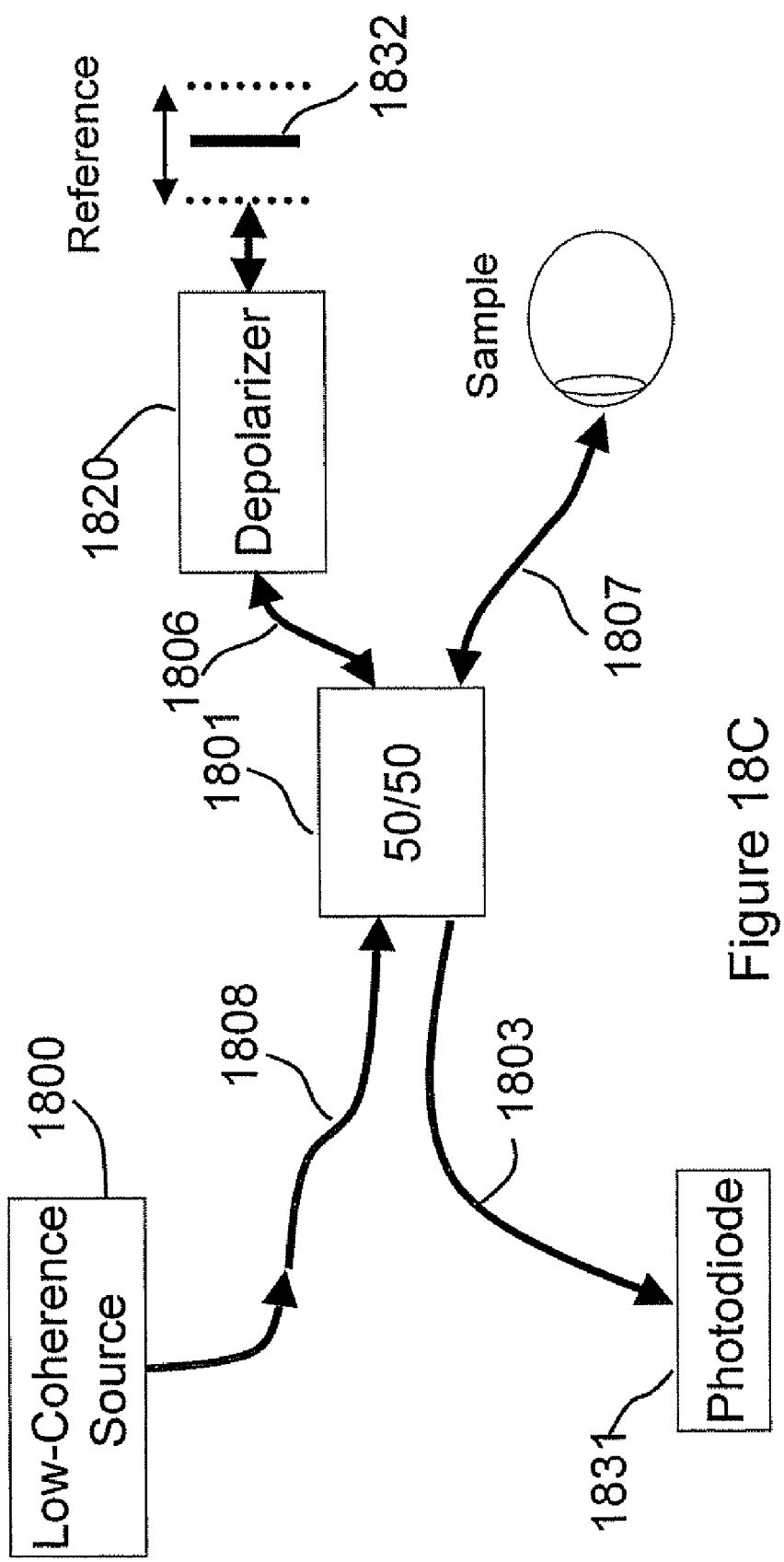
FIG. 18C is a schematic block diagram illustrating a time-domain optical coherence tomography system according to some embodiments of the present invention using a low coherence source with a depolarizer in the reference arm.

Referring now to FIG. 18C, an optical engine according to other embodiments of the present invention will be discussed. As illustrated in FIG. 18C, a depolarizer 1820 is placed in the reference arm of a time domain OCT engine that uses a broad band source 1800 and a scanning reference arm 1832. In this configuration the light returning from the reference arm is typically depolarized. When interfered with the light from the sample arm 1807, which is polarized or partially polarized, there will typically be an interference signal regardless of the specific polarization properties of the sample. Typically this architecture will result in a 3.0 dB decrease in OSNR relative to the maximum possible OSNR, but there will generally be minimal change in the signal strength regardless of the polarization properties of the sample or changes in the polarization properties of the system.

Figure 19A:
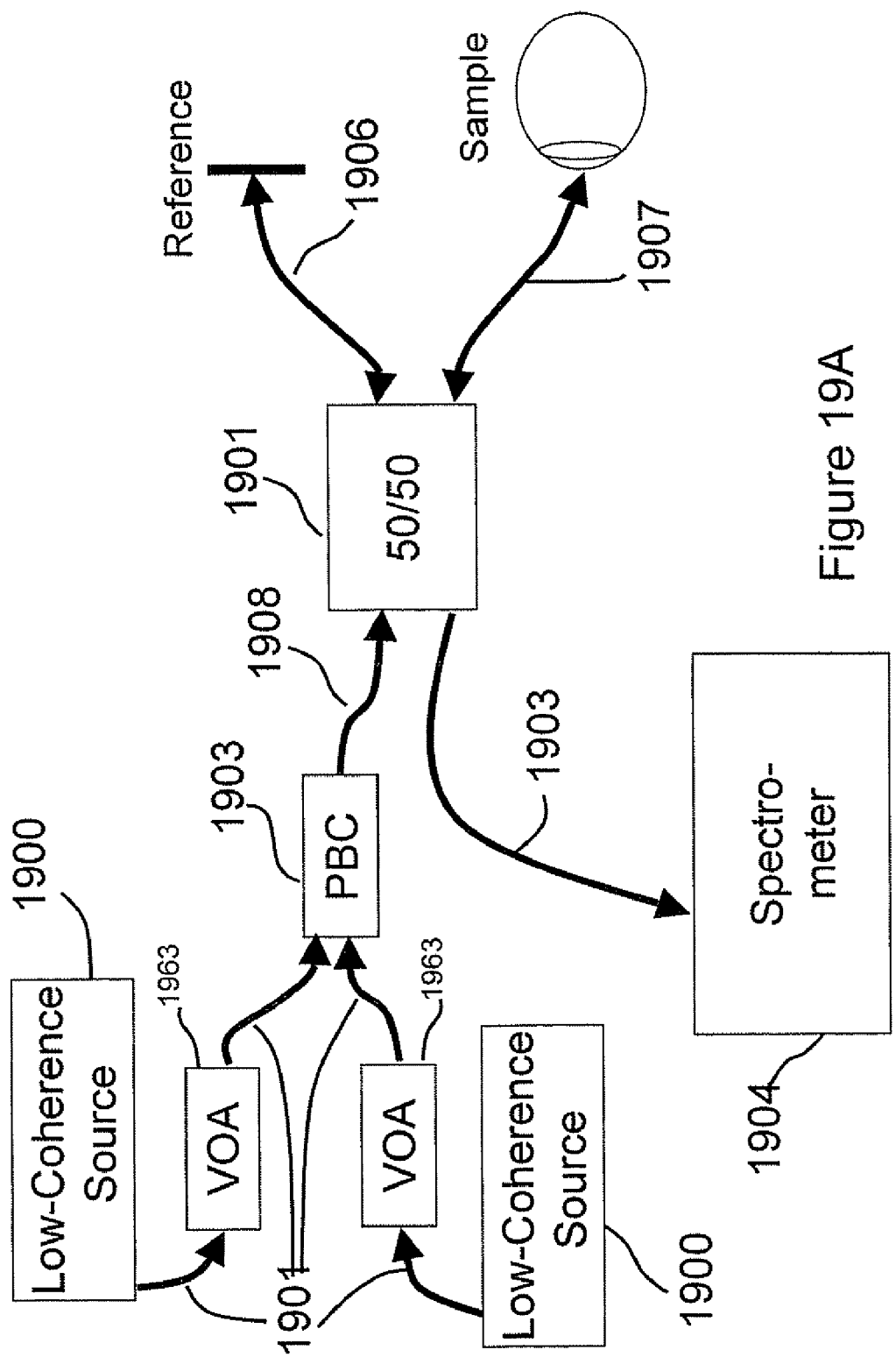
FIG. 19A is a schematic block diagram illustrating a Fourier-domain optical coherence tomography system according to some embodiments of the present invention using a polarization-multiplexed low coherence sources with power balancing using variable optical attenuators.

Referring now to FIG. 19A, an optical engine according to further embodiments of the present invention will be discussed. As illustrated in FIG. 19A, there are two or more low coherence sources 1900 that are connected to a polarization beam combiner (PBC) 1903. Between the sources 1900 and the PBC are optional variable optical attenuators 1963 which can be used to control the power level from each source. The fiber 1901 between the sources and the PBC may be polarization maintaining. In embodiments of the present invention illustrated in FIG. 19A, a source 1900 is coupled into each input of a polarization beam combiner so that the output of the PBC 1903 has power in each of the orthogonal polarizations and is depolarized. The rest of the engine is similar in design to FIG. 14A. Embodiments of the present invention illustrated in FIG. 19A may have the advantage that more optical power may be available to the engine and may not require polarization controllers to align polarization with various components.

Figure 19B:
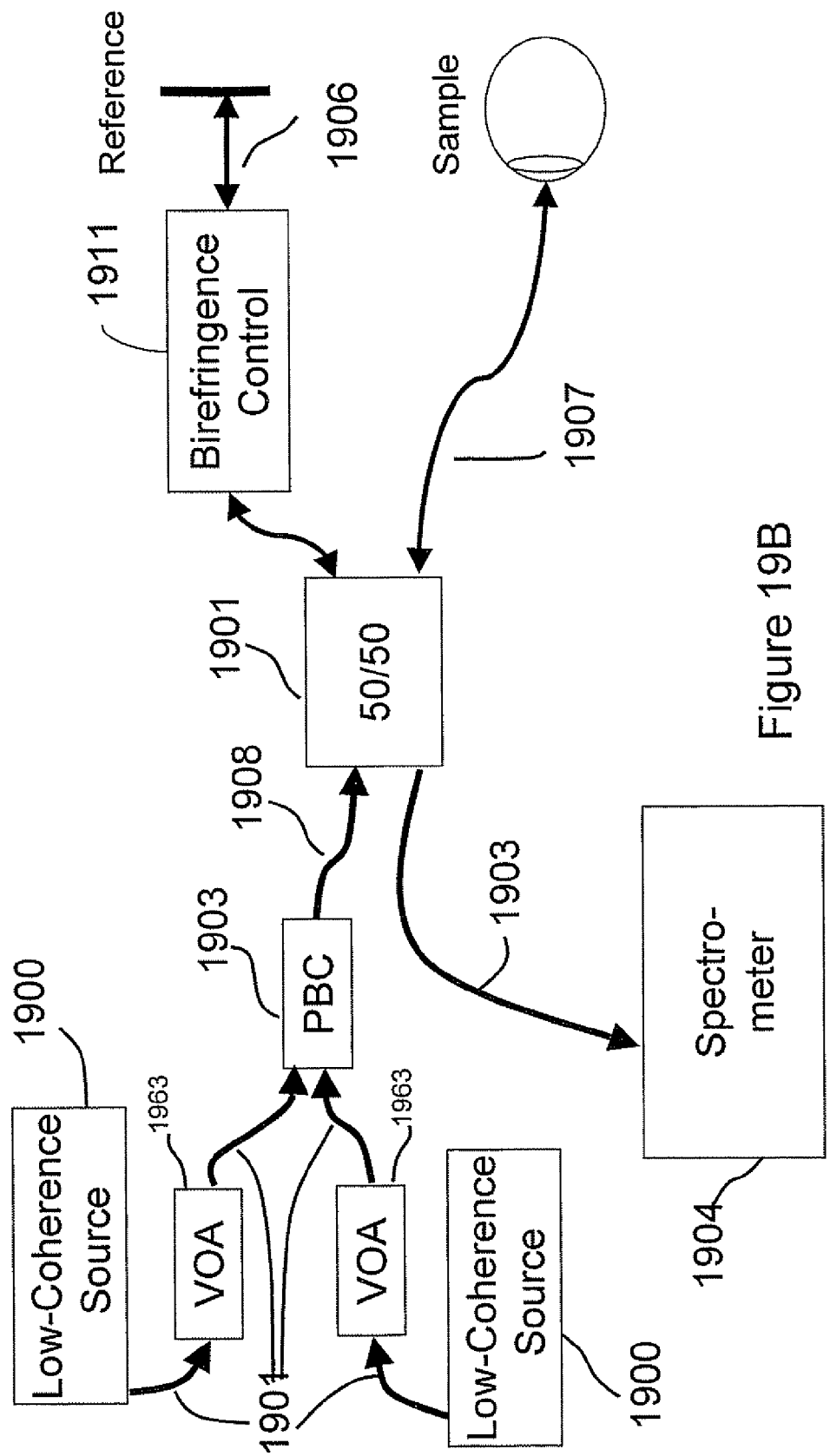
FIG. 19B is a schematic block diagram illustrating a Fourier-domain optical coherence tomography system according to some embodiments of the present invention using polarization-multiplexed low coherence sources with power balancing using variable optical attenuators and using birefringence control.
Figure 19C:
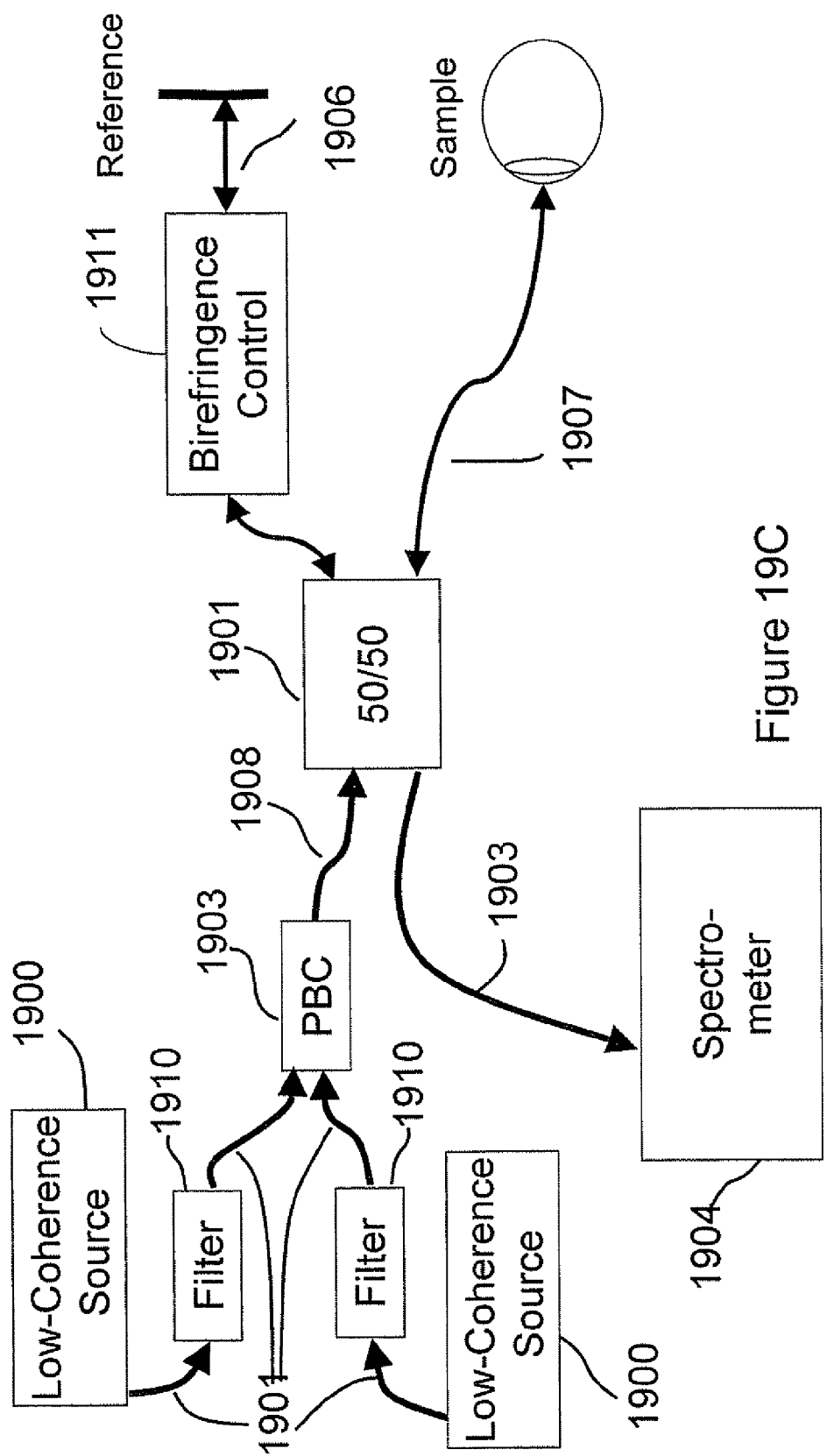
FIG. 19C is a schematic block diagram illustrating a Fourier-domain optical coherence tomography system according to some embodiments of the present invention using polarization-multiplexed low coherence sources with spectral equalization and using birefringence control.

Further embodiments of the present invention will now be discussed with respect to FIGS. 19B and 19C. In embodiments of the present invention illustrated in FIGS. 19B and 19C, birefringence control 1911 is applied as discussed above with respect to other embodiments of the present invention. As illustrated in FIG. 19C, one or more active or passive filters 1910 is added to increase the likelihood that power is equalized across the applicable spectrum for both multiplexed polarizations.

Figure 20A:
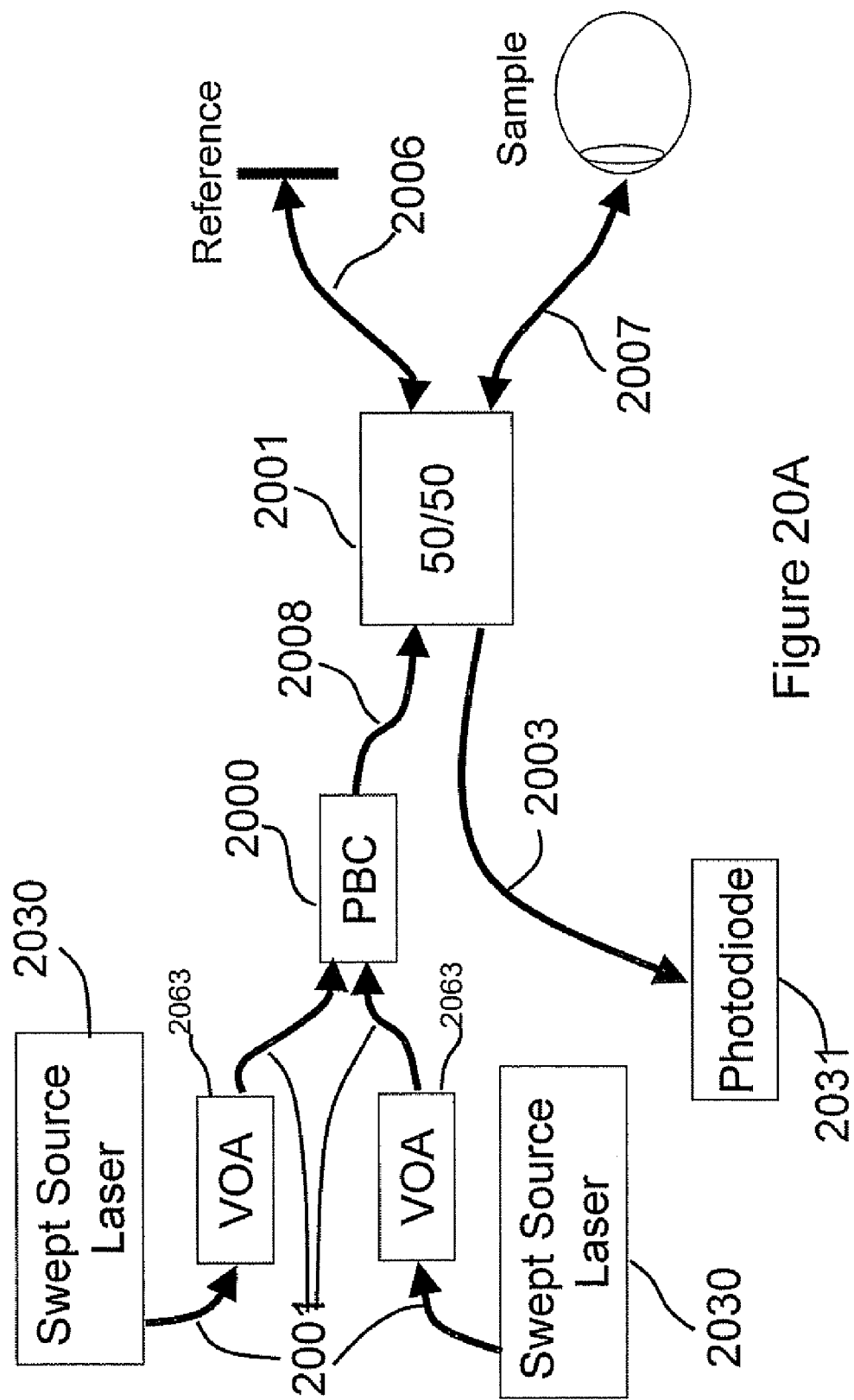
FIG. 20A is a schematic block diagram illustrating a Fourier-domain optical coherence tomography system according to some embodiments of the present invention using a polarization-multiplexed swept sources with power balancing using variable optical attenuators.

Referring now to FIG. 20A, there are two or more swept laser sources 2030 that are connected to a polarization beam combiner 2000. Between the sources 2030 and the PBC are optional variable optical attenuators 2063 which can be used to control the power level from each source. The fiber 2001 between the sources and the PBC may be polarization maintaining. In embodiments of the present invention illustrated in FIG. 20A a source 2030 is coupled into each input of a polarization beam combiner so that the output of the PBC 2000 has power in each of the orthogonal polarizations and is depolarized. Embodiments of the present invention illustrated in FIG. 20A may have an advantage that more optical power may be available to the engine and may not require polarization controllers to align polarization with various components.

Figure 20B:
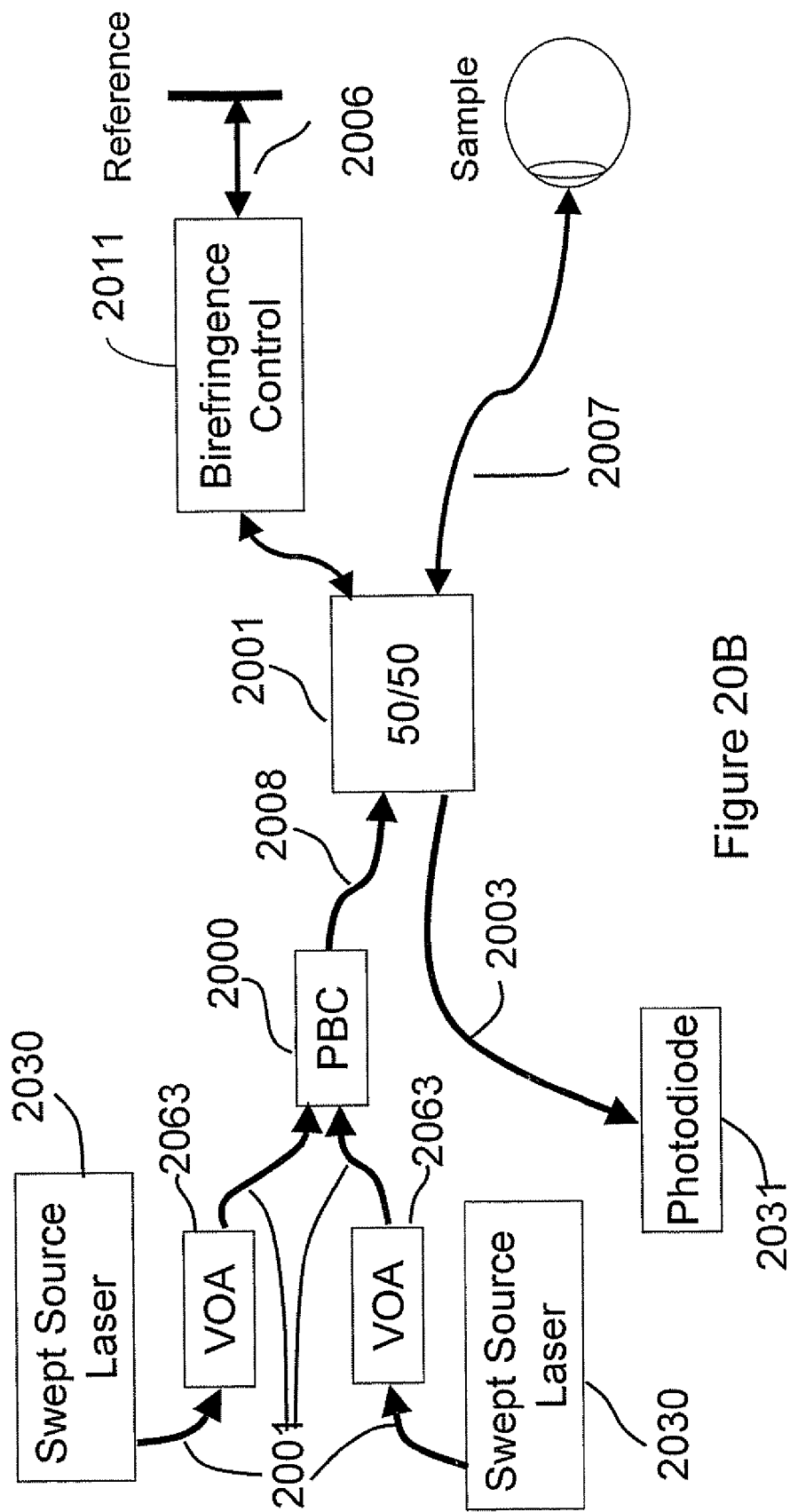
FIG. 20B is a schematic block diagram illustrating a Fourier-domain optical coherence tomography system according to some embodiments of the present invention using polarization-multiplexed swept sources with power balancing using variable optical attenuators and using birefringence control.
Figure 20C:
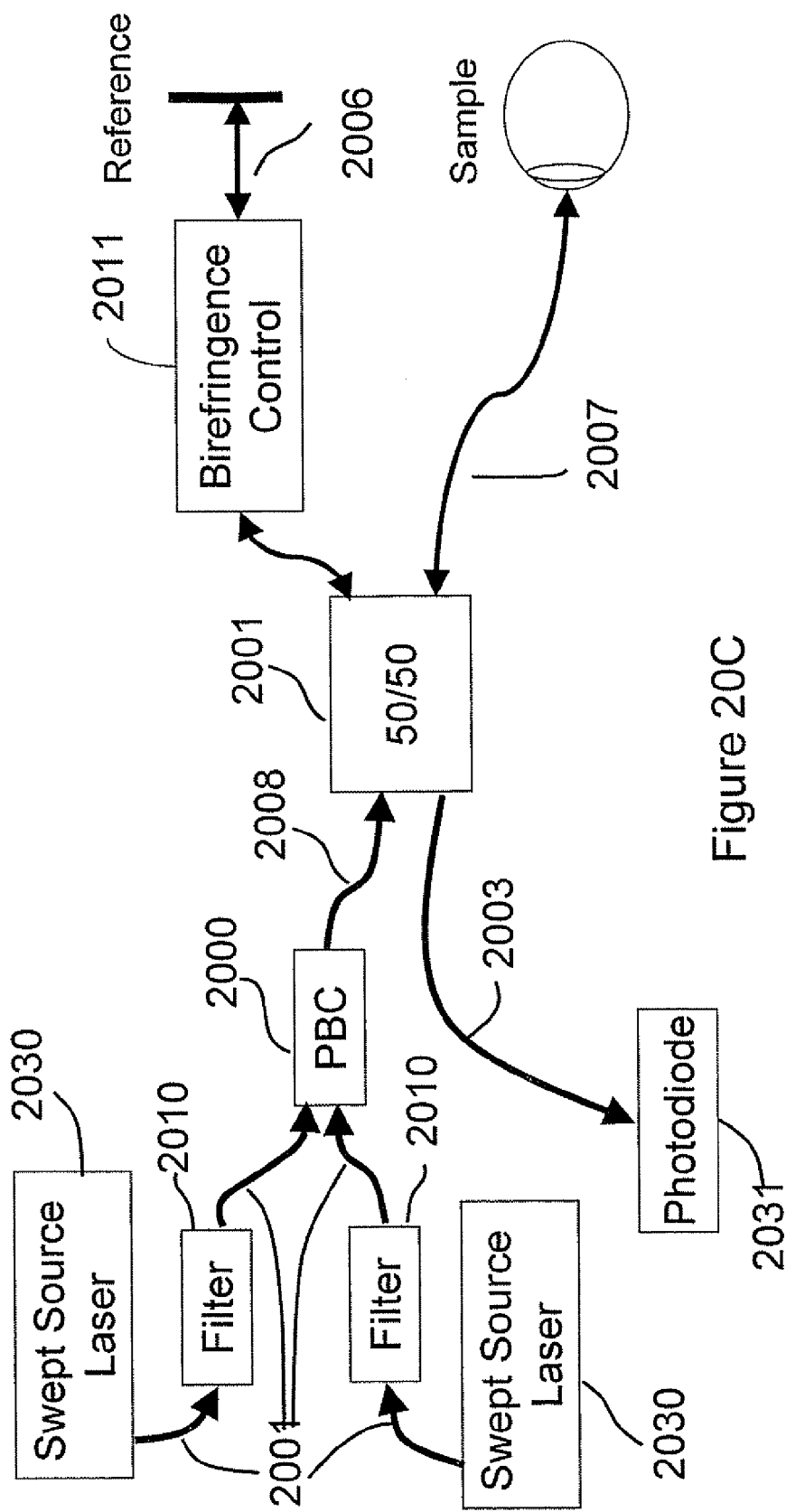
FIG. 20C is a schematic block diagram illustrating a Fourier-domain optical coherence tomography system according to some embodiments of the present invention using polarization-multiplexed swept sources with spectral equalization and using birefringence control.

Referring now to FIGS. 20B and 20C, birefringence control 2011 is applied as discussed in these embodiments as discussed in detail above. As illustrated in FIG. 20C, one or more active or passive filters 2010 may be added to increase the likelihood that power is equalized across the applicable spectrum for both multiplexed polarizations.

Figure 21A:
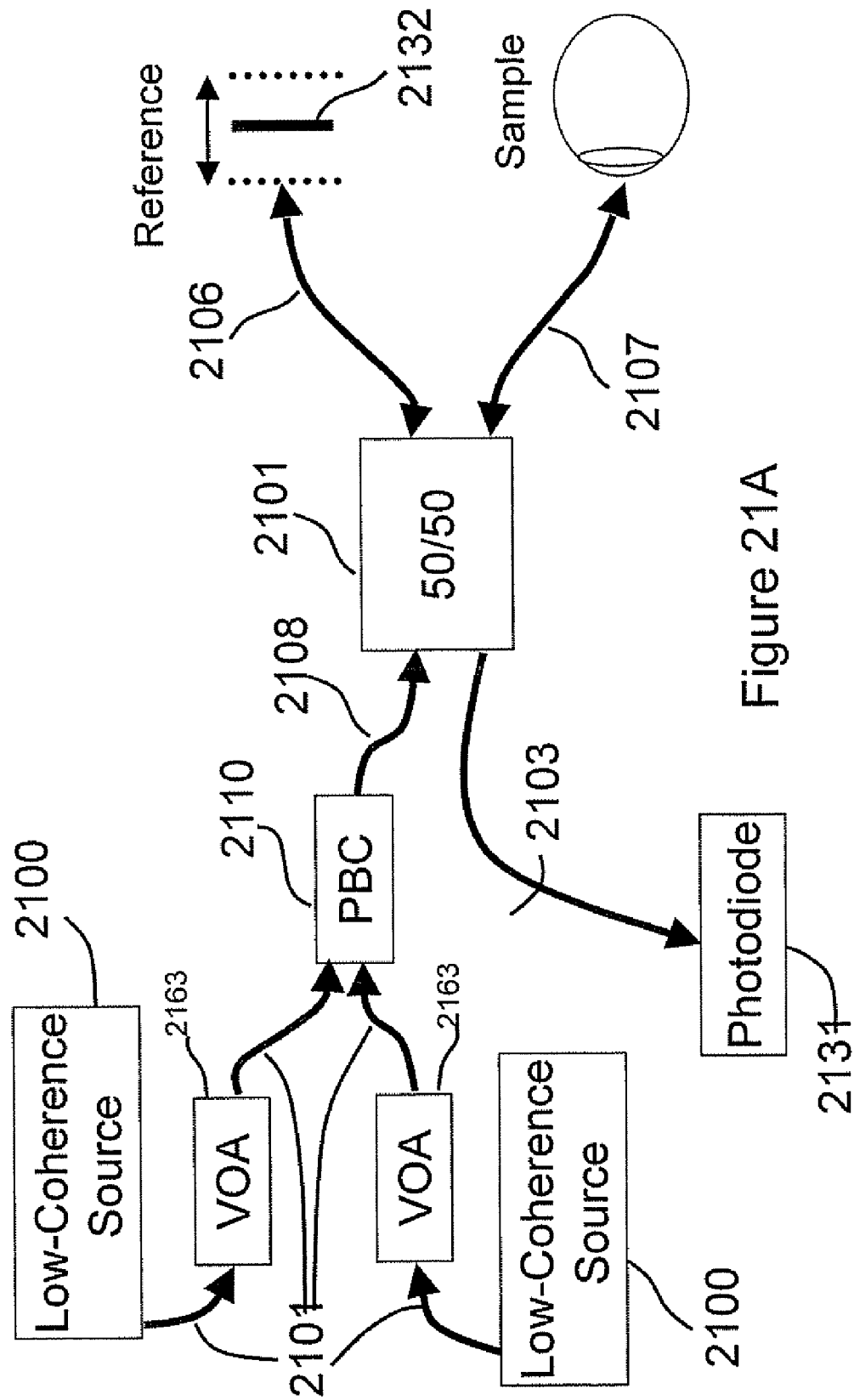
FIG. 21A is a schematic block diagram illustrating a time-domain optical coherence tomography system according to some embodiments of the present invention using a polarization-multiplexed low coherence sources with power balancing using variable optical attenuators.
Figure 21B:
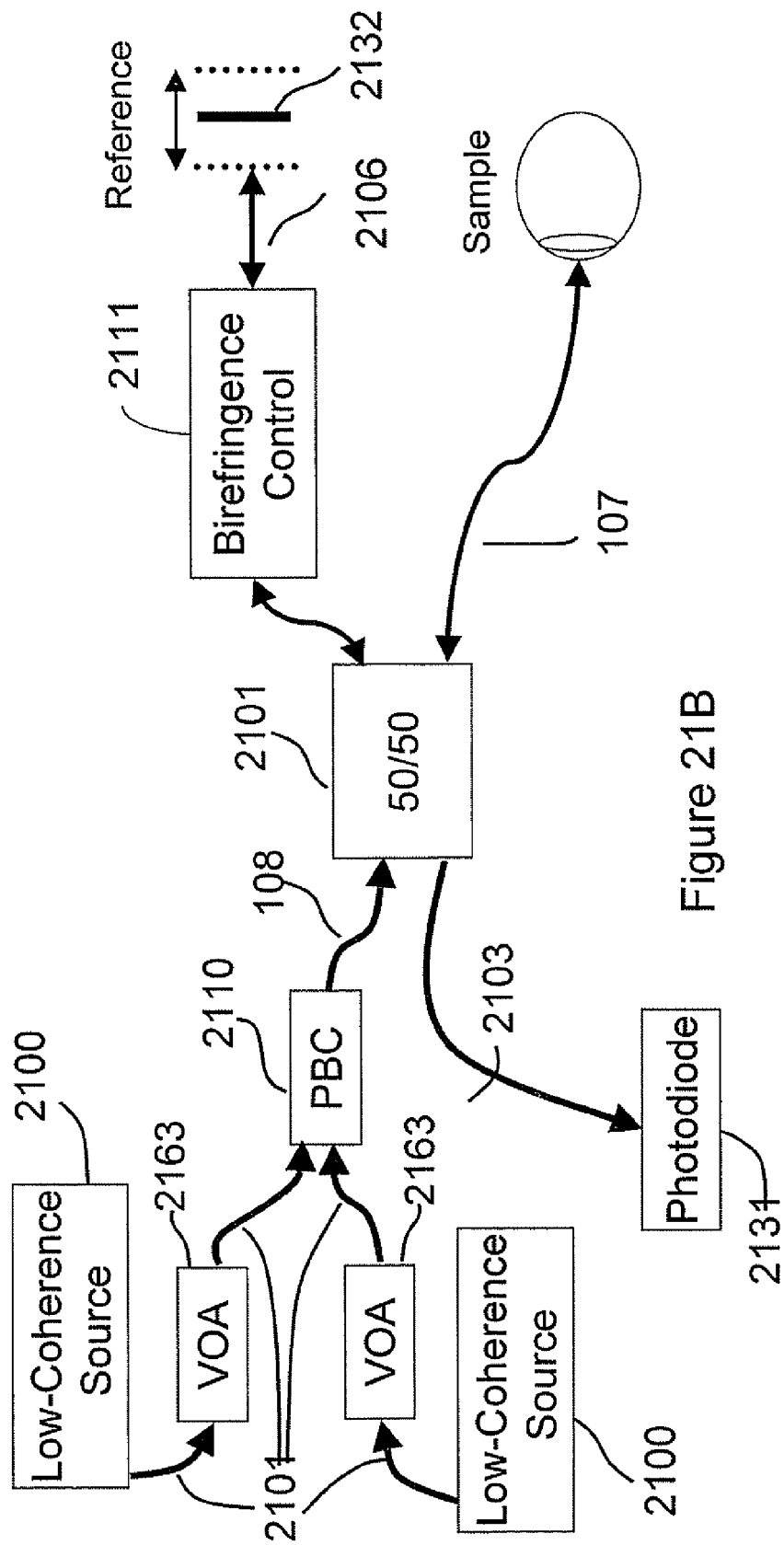
FIG. 21B is a schematic block diagram illustrating a time-domain optical coherence tomography system according to some embodiments of the present invention using polarization-multiplexed low coherence sources with power balancing using variable optical attenuators and using birefringence control.
Figure 21C:
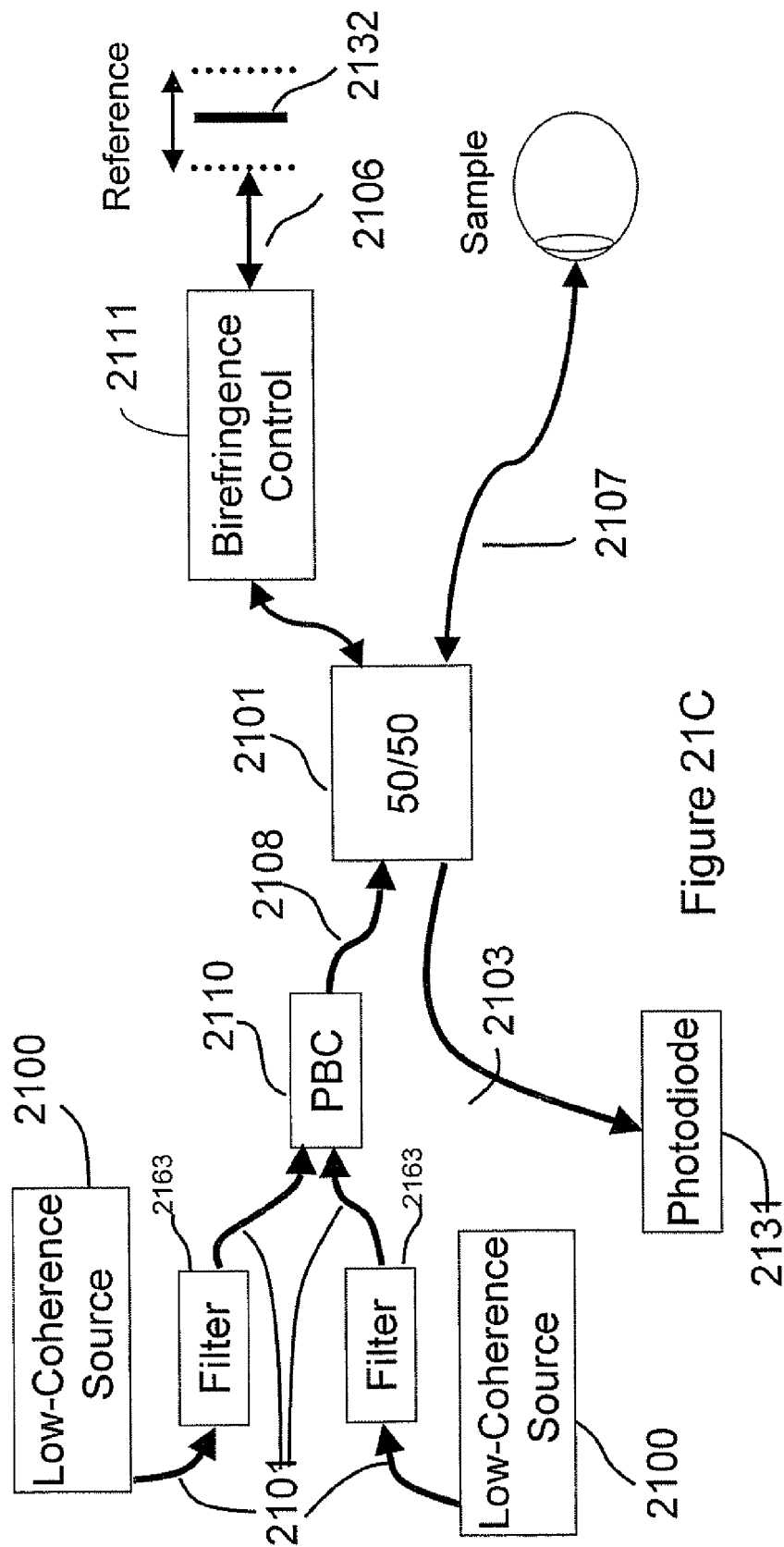
FIG. 21C is a schematic block diagram illustrating a time-domain optical coherence tomography system according to some embodiments of the present invention using polarization-multiplexed low coherence sources with spectral equalization and using birefringence control.

Referring now to FIG. 21A, there are two or more low coherence sources 2100 that are connected to a polarization beam combiner 2110. Between the sources 2100 and the PBC are optional variable optical attenuators 2163 which can be used to control the power level from each source. The fiber 2101 between the sources and the PBC may be polarization maintaining. In embodiments of the present invention illustrated in FIG. 21A, a source 2130 is coupled into each input of a polarization beam combiner so that the output of the PBC 2110 has power in each of the orthogonal polarizations and is depolarized. Embodiments of the present invention illustrated in FIG. 21A may have an advantage that more optical power may be available to the engine and may not require polarization controllers to align polarization with various components Referring now to FIGS. 21B and 21C, birefringence control 2111 is applied as discussed for previous embodiments. As further illustrated in FIG. 21C, one or more active or passive filters 2101 is added to increase the likelihood that power is equalized across the applicable spectrum for both multiplexed polarizations.

According to some embodiments of the present invention, birefringence control is specified to modify birefringence in each of two interferometric paths. According to Equation 27, polarization fading is modulated cosinusoidally according to a sum of the birefringence in each of the two interferometric paths. Birefringence as described herein may be the polarization-dependence of optical path length. Various methods of controlling the path birefringence are known to those having skill in the art.

Due to the cyclicality of the polarization fading described in Equation 27, birefringence control may be of high order, whereby the total change in birefringence may be over a distance equal to many wavelengths, or even greater than the coherence length of the light source. In some embodiments of the present invention, the birefringence control may be over a fraction of a wavelength for monochromatic interferometers, and over a fraction of a coherence length, for broadband, or low-coherence, interferometers.

Figure 22:
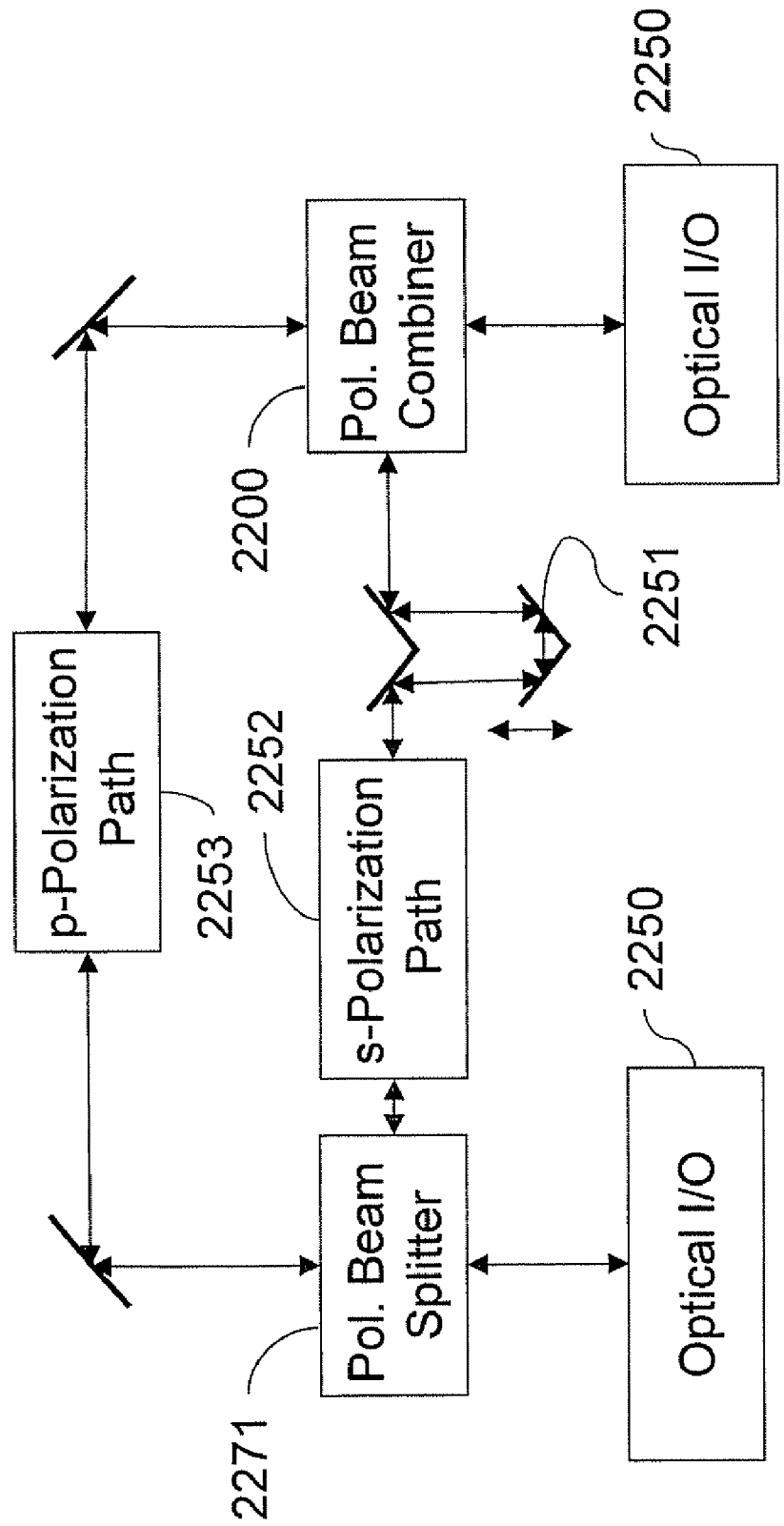
FIG. 22 is a schematic block diagram illustrating a two-path birefringence controller using polarization beam splitter and combiner with a variable delay line according to some embodiments of the present invention.

Referring now to FIG. 22, a variable path length interferometer according to some embodiments of the present invention will be discussed. In embodiments of the present invention illustrated in FIG. 22, input signal 2250 impinges on a polarization beam splitter 2271. The nominally unpolarized source is separated into two polarized components that travel a polarization path p 2253 along one direction and a polarization path s 2252 along a second direction. One or both paths include an independent path delay 2251 that has control of the optical path on the order of a small fraction, for example, about 10% or less, of the wavelength of light, with enough range to cover a path length change equal to at least one to at least a few optical wavelengths. Such control can be provided, for example, by a piezo-electric controller. The light is recombined into the polarization beam combiner 2200 and reintroduced into the optical path of the interferometer 2250.

Figure 23:
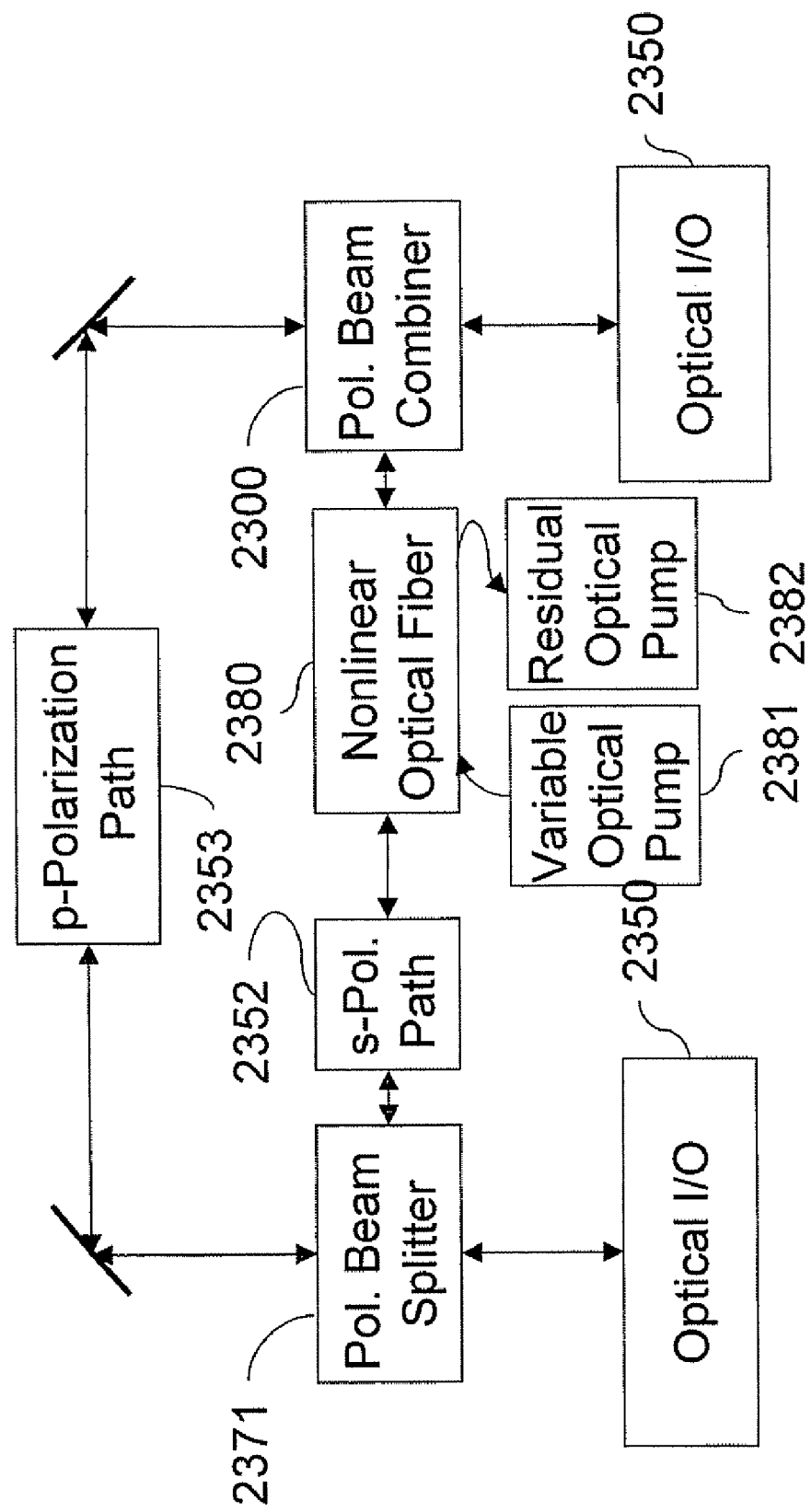
FIG. 23 is a schematic block diagram illustrating a two-path birefringence controller using polarization beam splitter and combiner with nonlinear optical phase delay according to some embodiments of the present invention.

Referring now to FIG. 23, an interferometer according to some embodiments of the present invention will be discussed. As illustrated in FIG. 23, nonlinear optical phase modulation in a nonlinear optical fiber 2380 may be used to finely control the effective optical path length on one or both of paths 2353 and/or 2352. In embodiments of the present invention illustrated in FIG. 23, pump light 2381 in a wavelength band disjoint from the interferometer source wavelength band is introduced into the nonlinear fiber 2380. The induced phase delay is in direct proportion to the intensity of the pump light 2381 and the nonlinear refractive index of the optical fiber 2380. Residual pump 2382 is removed from the path at the output to reduce the likelihood that it will contribute to the detected interferometric signal.

The tensor, or polarization, properties of intensity dependent nonlinear interactions are known to those having skill in the art. Embodiments of the present invention illustrated in FIG. 23 may also include a single optical fiber path with s- and p- input polarizations 2353 and 2352, and a pump 2381 with polarization control to modify the relative phase delay imparted on the two orthogonal signal polarizations.

Figure 24:
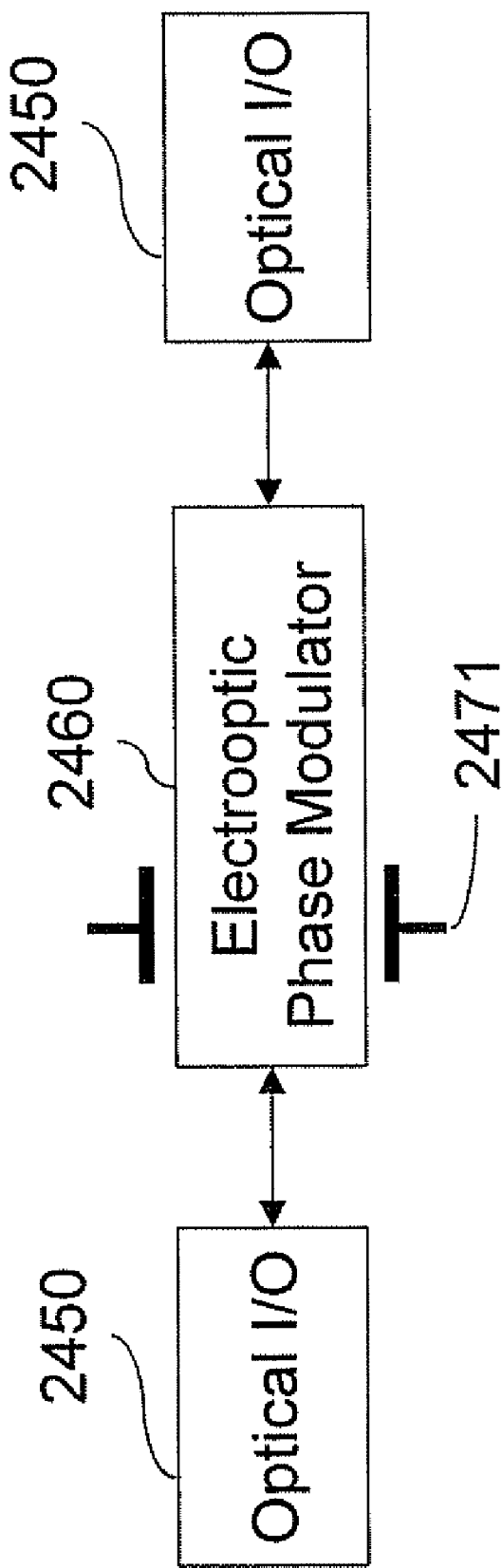
FIG. 24 is a schematic block diagram illustrating a birefringence controller using polarization beam splitter and combiner with an electro optic phase modulator according to some embodiments of the present invention.

Referring now to FIG. 24, interferometers according to further embodiments of the present invention will be discussed. As illustrated in FIG. 24, electro optic phase modulation 2460 is used to finely control the effective optical path length differential between orthogonal polarizations. Generally, voltage control 2471 is used to control the effective birefringence of an electro optic crystal 2460.

Figure 25:
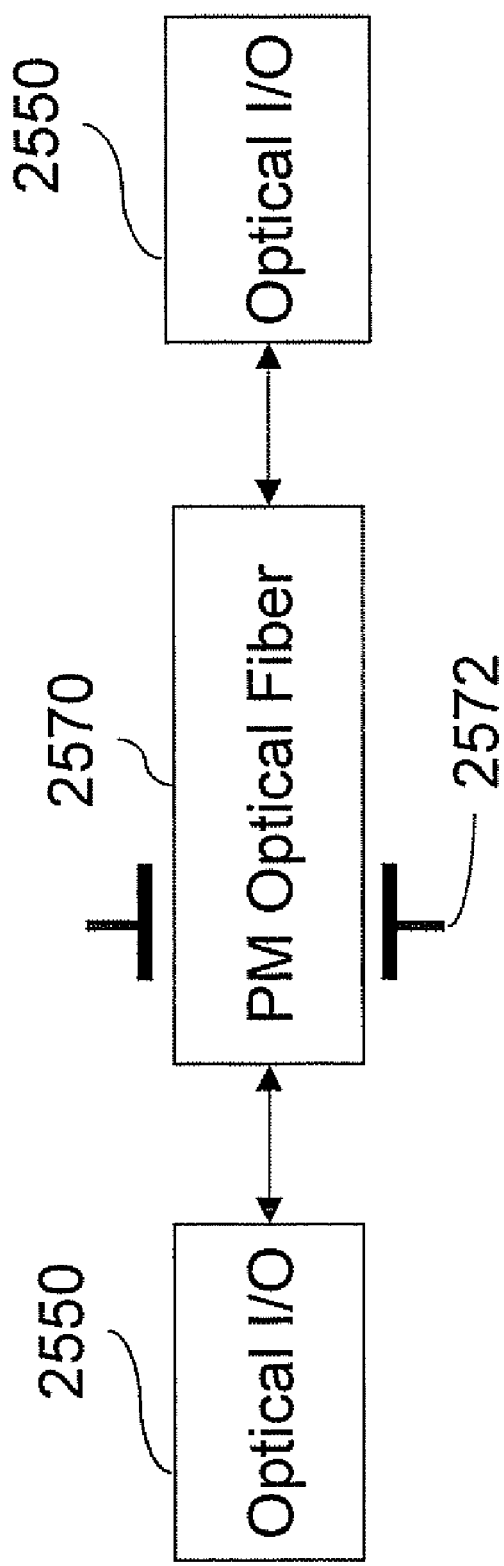
FIG. 25 is a schematic block diagram illustrating a birefringence controller using polarization beam splitter and combiner with an polarization-maintaining fiber phase modulator according to some embodiments of the present invention.

Referring now to FIG. 25, interferometers according to further embodiments of the present invention will be discussed. As illustrated in FIG. 25, phase modulation between orthogonal polarization components is created in polarization-maintaining optical fiber (PMF) 2570. Mechanically stretching 2572 a PMF over one beat length, typically on the order of one or a few millimeters, is sufficient to provide the level or birefringence control required in the present invention.

Figure 26:
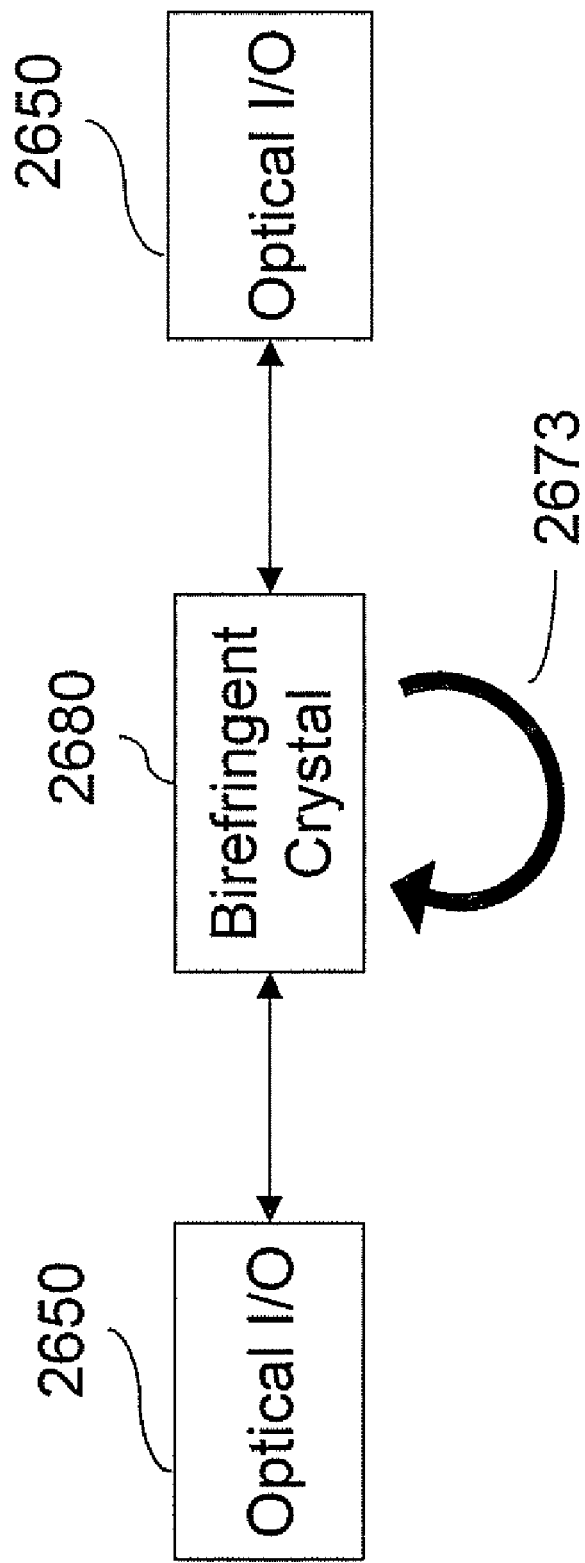
FIG. 26 is a schematic block diagram illustrating a birefringence controller using a birefringent crystal according to some embodiments of the present invention.

Referring now to FIG. 26, interferometers according to further embodiments of the present invention will be discussed. As illustrated in FIG. 26, the magnitude of accumulated birefringence is controlled by rotating a birefringent crystal 2680, such as a multi-order optical waveplate. Rotating 2673 a crystal with a fixed refractive index difference for orthogonal polarizations in order to increase the total path length through the crystal is sufficient to provide the level or birefringence control required in the present invention.

According to some embodiments of the invention, birefringence control is achieved with the use of active feedback, by maximizing a metric of the interferometric signal. The metric may include, for example, peak interferometric signal power, average signal power, or a ratio that involves the maximum signal power, minimum signal power, and/or average signal powers, derived over some operating range.

In the drawings and specification, there have been disclosed typical illustrative embodiments of the invention and, although specific terms are employed, they are used in a generic and descriptive sense only and not for purposes of limitation, the scope of the invention being set forth in the following claims.

That which is claimed is:

1. An optical imaging system comprising:
  a light source in a source arm of the optical imaging system;
  a depolarizer coupled to the light source in the source arm of the optical imaging system configured to substantially depolarize the light from the light source; and
  a birefringence controller in at least one of a first path and a second path of the system, the birefringence controller being configured to modify a polarization-dependent optical path length in the at least one of the first and second paths.

2. The system of claim 1, wherein control settings of the birefringence controller are set during manufacture and configured to be adjusted infrequently.

3. The system of claim 1, wherein control settings of the birefringence controller are dynamic and configured to be set based on a metric of a measured or imaged signal and/or a rate of active control associated with demands of an application.

4. The system of claim 1, further comprising a power coupler coupled to the depolarizer and the first and second paths, the power coupler being configured to provide light to and combine light from the first and second paths.

5. The system of claim 1, further comprising an isolator coupled between the light source and the depolarizer and configured to inhibit light from reentering the light source.

6. The system of claim 1, further comprising a spectrometer in a detector arm of the optical imaging system, the spectrometer being configured to receive light from the light source and disperse the received light onto at least one detector.

7. The system of claim 6, wherein the detector comprises a detector array including a plurality of detectors, ones of the plurality of detectors being configured to measure a power in a frequency band that is a subset of a total spectrum of the light source.

8. The system of claim 7, wherein the depolarizer is further configured to substantially depolarize over the frequency band viewed by a single detector.

9. The system of claim 1, further comprising a photodiode in a detector arm of the optical imaging system, the photodiode being configured to measure incident power over a time interval.

10. The system of claim 1, wherein the depolarizer comprises a Lyot depolarizer, a multi-path depolarizer or a polarization scrambler.

11. The system of claim 1, wherein the optical imaging system comprises a spectral domain optical coherence tomography (OCT) imaging system and wherein the light source comprises a broadband light source.

12. The system of claim 1, wherein the optical imaging system comprises a frequency domain optical coherence tomography (OCT) imaging system and wherein the light source comprises a narrowband light source having an optical frequency that varies with time.

13. The system of claim 1, wherein the optical imaging system comprises a time domain optical coherence tomography (OCT) imaging system and wherein the light source comprises a broadband light source.

14. An optical imaging system comprising:
a light source in a source arm of the optical imaging system;
a depolarizer in a reference arm of the optical imaging system, the depolarizer being configured to substantially depolarize light returning from the reference arm; and
a birefringence controller in at least one of a first path and a second path of the system, the birefringence controller being configured to modify a polarization-dependent optical path length in the at least one of the first and second paths.

15. An optical interferometry system comprising:
a light source configured to provide substantially unpolarized light to first and second paths; and
a birefringence controller in at least one of the first and second paths and configured to modify a polarization-dependent optical path length in the at least one of the first and second paths.

16. The system of claim 15, further comprising a depolarizer in the at least one of the first and second paths including the birefringence controller, the depolarizer being configured to compensate for polarizing elements present in the at least one of the first and second paths.

17. The system of claim 15, wherein the system further comprises a power coupler coupled to the unpolarized light source and the first and second paths, the power coupler being configured to provide a portion of light produced by the unpolarized light source to the first path and a remaining portion of the light produced by the unpolarized source to the second path.

18. The system of claim 17, further comprising:
a first reflector in the first path that reflects at least a portion of the light provided to the first path; and
a second reflector in the second path that reflects at least a portion of the light provided to the second path.

19. The system of claim 18, wherein the power coupler is further configured to combine the reflected light from the first and second paths, the system further comprising a detector configured to receive the combined reflected light.

20. The system of claim 15, wherein the system further comprises a power splitter coupled to the unpolarized light source and the first and second paths, the power splitter being configured to provide a portion of light produced by the unpolarized source to the first path and a remaining portion of the light produced by the unpolarized source to the second path.

21. The system of claim 20, a power coupler coupled to the first and second paths and configured to combine at least a portion of the light provided to the first path and at least some portion of the light provided to the second path.

22. The system of claim 21, further comprising a detector configured to receive the combined light from the first and second paths.

23. A method of imaging in an interferometric imaging system, the method comprising:
providing substantially unpolarized light to first and second optical paths of the interferometric imaging system; and
modifying a polarization-dependent optical path length in at least one of the first and second paths of the interferometric imaging system using a birefringence controller in at least one of the first and second paths.

24. The method of claim 23, further comprising measuring an optical power in a frequency band that is a subset of a total spectrum of the light source.

25. The method of claim 23, further comprising measuring incident power over a time interval.

26. The method of claim 23, wherein providing substantially unpolarized light comprises receiving substantially unpolarized light from a substantially unpolarized light source to provide the substantially unpolarized light.

27. The method of claim 23, wherein providing substantially unpolarized light comprises:
receiving polarized light from a polarized light source; and
substantially depolarizing the received polarized light to provide the substantially unpolarized light.

28. The method of claim 27, wherein depolarizing the received polarized light further comprises substantially depolarizing the light for all wavelengths and times, depolarizing the light using a wavelength and/or depolarizing the light using a time-average.

29. The method of claim 23, wherein the optical imaging system comprises an optical coherence tomography (OCT) imaging system.

30. An interferometric imaging system comprising:
a substantially depolarized light that is transmitted over a reference and/or sample path of the imaging system, the reference and/or sample path having birefringence;
a birefringence controller in at least one of the reference and/or sample paths configured to control a difference in birefringence between the sample and reference paths; and
a detector configured to detect an interfered signal of the substantially depolarized light, wherein the birefringence controller is further configured to adjust interferometric fringe visibility.

* * * * *

UNITED STATES PATENT AND TRADEMARK OFFICE
CERTIFICATE OF CORRECTION

PATENT NO. : 7,545,504 B2 Page 1 of 1
APPLICATION NO. : 11/539275
DATED : June 9, 2009
INVENTOR(S) : Buckland et al.

It is certified that error appears in the above-identified patent and that said Letters Patent is hereby corrected as shown below:

On the Title Page:
Item 73, Assignee: Please correct "Biotigen, Inc.," to read -- Bioptigen, Inc., --

Signed and Sealed this

Eighteenth Day of August, 2009

David J. Kappos
*Director of the United States Patent and Trademark Office*